(12) United States Patent
Mohan et al.

(10) Patent No.: US 11,780,842 B2
(45) Date of Patent: Oct. 10, 2023

(54) TYK2 PSEUDOKINASE LIGANDS

(71) Applicant: Ventyx Biosciences, Inc., Encinitas, CA (US)

(72) Inventors: Raju Mohan, Encinitas, CA (US); John Nuss, Encinitas, CA (US); Jason Harris, Encinitas, CA (US); Shendong Yuan, Encinitas, CA (US)

(73) Assignee: VENTYX BIOSCIENCES, INC., Encinitas, CA (US)

( * ) Notice: Subject to any disclaimer, the term of this patent is extended or adjusted under 35 U.S.C. 154(b) by 186 days.

(21) Appl. No.: 17/441,788

(22) PCT Filed: Mar. 25, 2020

(86) PCT No.: PCT/US2020/024746
§ 371 (c)(1),
(2) Date: Sep. 22, 2021

(87) PCT Pub. No.: WO2020/198379
PCT Pub. Date: Oct. 1, 2020

(65) Prior Publication Data
US 2022/0169651 A1 Jun. 2, 2022

Related U.S. Application Data

(60) Provisional application No. 62/824,144, filed on Mar. 26, 2019.

(51) Int. Cl.
| | | |
|---|---|---|
| *C07D 498/18* | (2006.01) | |
| *C07D 498/22* | (2006.01) | |
| *A61P 19/02* | (2006.01) | |
| *A61P 25/28* | (2006.01) | |
| *A61P 37/06* | (2006.01) | |
| *A61P 17/06* | (2006.01) | |
| *C07D 471/22* | (2006.01) | |
| *C07D 491/22* | (2006.01) | |
| *C07D 513/22* | (2006.01) | |

(52) U.S. Cl.
CPC ............ *C07D 471/22* (2013.01); *A61P 17/06* (2018.01); *A61P 19/02* (2018.01); *A61P 25/28* (2018.01); *A61P 37/06* (2018.01); *C07D 491/22* (2013.01); *C07D 498/18* (2013.01); *C07D 498/22* (2013.01); *C07D 513/22* (2013.01); *C07B 2200/05* (2013.01)

(58) Field of Classification Search
CPC ............................. C07D 498/18; C07D 498/22
See application file for complete search history.

(56) References Cited

U.S. PATENT DOCUMENTS

| | | | |
|---|---|---|---|
| 7,119,200 B2 | 10/2006 | Guzi et al. | |
| 7,161,003 B1 | 1/2007 | Guzi et al. | |
| 7,196,078 B2 | 3/2007 | Guzi et al. | |
| 8,580,782 B2 | 11/2013 | Guzi et al. | |
| 8,586,576 B2 | 11/2013 | Guzi et al. | |
| 2006/0189632 A1 | 8/2006 | Kataoka et al. | |
| 2007/0082900 A1 | 4/2007 | Guzi et al. | |
| 2010/0125068 A1 | 5/2010 | Guzi et al. | |
| 2012/0114739 A1 | 5/2012 | Deng et al. | |
| 2017/0129899 A1 | 5/2017 | Shvartsbart et al. | |
| 2017/0283435 A1 | 10/2017 | Andrews et al. | |
| 2018/0258086 A1 | 9/2018 | Greenwood et al. | |
| 2019/0031664 A1 | 1/2019 | Masse et al. | |
| 2019/0076436 A1 | 3/2019 | Andrews et al. | |
| 2020/0131201 A1 | 4/2020 | Masse et al. | |
| 2021/0139486 A1 | 5/2021 | Mohan et al. | |
| 2022/0135567 A1 | 5/2022 | Mohan et al. | |

FOREIGN PATENT DOCUMENTS

| | | |
|---|---|---|
| WO | WO-2004076458 A1 | 9/2004 |
| WO | WO-2008130569 A1 | 10/2008 |
| WO | WO-2018081488 A1 | 5/2018 |
| WO | WO-2018213365 A1 | 11/2018 |
| WO | WO-2019023468 A1 | 1/2019 |
| WO | WO-2020055636 A1 | 3/2020 |
| WO | WO-2020081508 A1 | 4/2020 |
| WO | WO-2020123225 A1 | 6/2020 |
| WO | WO-2020163778 A1 | 8/2020 |
| WO | WO-2020185755 A1 | 9/2020 |
| WO | WO-2020198379 A1 | 10/2020 |
| WO | WO-2021092246 A1 | 5/2021 |

OTHER PUBLICATIONS

Berge et al. Pharmaceutical Salts. Journal of Pharmaceutical Sciences 66(1):1-19 (Jan. 1977).
Moslin et al. Identification of imidazo[1,2-b]pyridazine TYK2 pseudokinase ligands as potent and selective allosteric inhibitors of TYK2 signalling. MedChemCommun. 8:700-712 (2017).
PCT/US2020/024746 Invitation to Pay Additional Fees dated May 21, 2020.
PCT/US2020/024746 International Search Report and Written Opinion dated Jul. 23, 2020.
Dorwald. Side Reactions in Organic Synthesis: A Guid to Successful Synthesis Design. Weinheim: WILEY-VCH Verlag GmbH & Co. KGaA. 2005. Preface.
Hackam, et al. Translation of research evidence from animals to humans. JAMA 296(14):1731-2 (2006).
Jordan. Tamoxifen: A most unlikely pioneering medicine. Nature Reviews: Drug Discovery 2:205-213 (2003).
Vippagunta et al. Crystalline Solids. Advanced Drug Delivery Reviews 48:3-26 (2001).

*Primary Examiner* — Susanna Moore

(74) *Attorney, Agent, or Firm* — WILSON SONSINI GOODRICH & ROSATI

(57) ABSTRACT

Described herein are TYK2 pseudokinase ligands and methods of utilizing TYK2 pseudokinase ligands in the treatment of diseases, disorders or conditions. Also described herein are pharmaceutical compositions containing such compounds.

19 Claims, No Drawings

TYK2 PSEUDOKINASE LIGANDS

CROSS-REFERENCE

This application is a U.S. National Stage entry of PCT application PCT/US2020/024746 filed Mar. 25, 2020, which claims benefit of U.S. Provisional Application No. 62/824,144, filed on Mar. 26, 2019, each of which is herein incorporated by reference in its entirety.

BACKGROUND OF THE INVENTION

Janus kinase (JAK) is a family of intracellular, non-receptor tyrosine kinases that transduce cytokine-mediated signals via the JAK-STAT pathway. The four JAK family members are Janus kinase 1 (JAK1), Janus kinase 2 (JAK2), Janus kinase 3 (JAK3), and Tyrosine kinase 2 (TYK2) and have been shown to be key components of cytokine-mediated effects. Unlike JAK1 deficient mice, TYK2 deficient mice are viable and the TYK2 deficiency has been shown to be protective in various models of autoimmunity.

SUMMARY OF THE INVENTION

In one aspect, provided herein are compounds of Formula (I) or Formula (II):

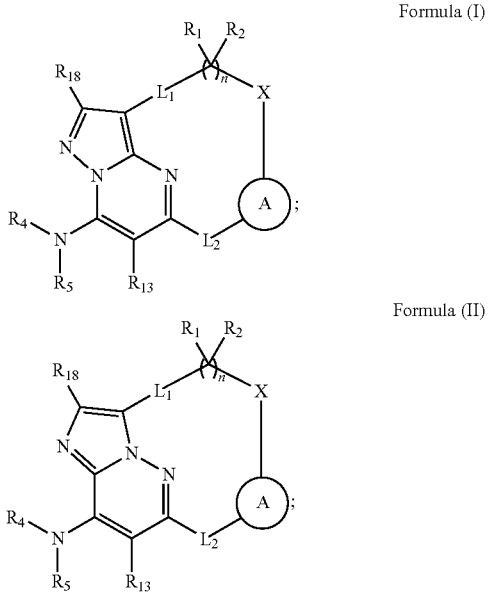

wherein:

$\bigcirc\!\!\!\!A$ is $C_3$-$C_6$cycloalkyl, $C_6$-$C_{10}$aryl, $C_2$-$C_9$heterocycloalkyl, or $C_2$-$C_9$heteroaryl, wherein $C_3$-$C_6$cycloalkyl, $C_6$-$C_{10}$aryl, $C_2$-$C_9$heterocycloalkyl, or $C_2$-$C_9$heteroaryl is optionally substituted with 1, 2, 3, or 4 $R_7$;

X is —O—, —C($R_9$)($R_{10}$)—, —C($R_9$)($R_{10}$)—O—, —O—C($R_9$)($R_{10}$), —C(O)—, —C(O)N($R_3$)—, —N($R_3$)C(O)—, or —N($R_{17}$)—;

$L_1$ is —C(O)N($R_3$)—, —N($R_3$)C(O)—, —C($R_9$)($R_{10}$)—O—, or —O—C($R_9$)($R_{10}$)—;

$L_2$ is —N($R_6$)—, —N($R_6$)CH$_2$—, or —CH$_2$N($R_6$)—;

each $R_1$ is independently selected from hydrogen, deuterium, $C_1$-$C_6$alkyl, and $C_1$-$C_6$deuteroalkyl;

each $R_2$ is independently selected from hydrogen, deuterium, $C_1$-$C_6$alkyl, and $C_1$-$C_6$deuteroalkyl; or $R_1$ and $R_2$ are combined to form a 3-, 4-, 5-, or 6-membered cycloalkyl ring or a 4-, 5-, or 6-membered heterocycloalkyl ring;

each $R_3$ is independently hydrogen or $C_1$-$C_6$alkyl; or $R_2$ and $R_3$ together with the atoms to which they are attached are combined to form a 5- or 6-membered heterocycloalkyl ring optionally substituted 1, 2, or 3 with groups selected from halogen, —OH, $C_1$-$C_6$alkyl, and —$C_1$-$C_6$alkyl-OH;

$R_4$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

$R_5$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

$R_{13}$ is hydrogen, deuterium, $C_1$-$C_6$alkyl, or $C_1$-$C_6$deuteroalkyl; or $R_5$ and $R_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_6$ is hydrogen or $C_1$-$C_6$alkyl;

each $R_7$ is independently selected from deuterium, halogen, $C_1$-$C_6$alkyl, $C_1$-$C_6$deuteroalkyl, $C_1$-$C_6$haloalkyl, $C_1$-$C_6$alkoxy, $C_1$-$C_6$heteroalkyl, oxo, —OR$_{11}$, —N($R_{11}$)$_2$, —CN, —C(=O)R$_{12}$, —C(=O)OR$_{11}$, —C(=O)N($R_{11}$)$_2$, —NR$_{11}$C(=O)R$_{12}$, —NR$_{11}$S(=O)$_2$R$_{12}$, —S(=O)$_2$R$_{12}$, and —S(=O)$_2$N($R_{11}$)$_2$;

each $R_9$ and each $R_{10}$ are independently selected from hydrogen, deuterium, $C_1$-$C_6$alkyl, and $C_1$-$C_6$deuteroalkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —OR$_{14}$, —N($R_{14}$)$_2$, —C(=O)OR$_{14}$, and —C(=O)N($R_{14}$)$_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{17}$ is hydrogen or $C_1$-$C_6$alkyl;

$R_{18}$ is hydrogen, deuterium, halogen, $C_1$-$C_6$alkyl, or $C_1$-$C_6$deuteroalkyl; and n is 1, 2, 3, or 4;

or a pharmaceutically acceptable salt or solvate thereof.

In some embodiments is a compound of Formula (I), or a pharmaceutically acceptable salt or solvate thereof:

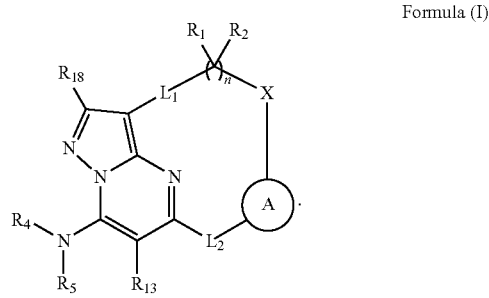

In some embodiments is a compound of Formula (II), or a pharmaceutically acceptable salt or solvate thereof:

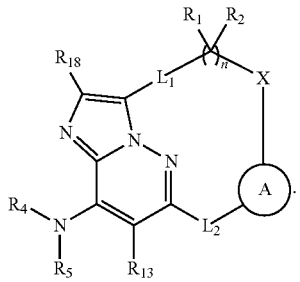

Formula (II)

In some embodiments is a compound of Formula (I) or (II), or a pharmaceutically acceptable salt or solvate thereof, wherein (A) is $C_6$-$C_{10}$aryl optionally substituted with 1, 2, or 3 $R_7$. In some embodiments is a compound of Formula (I) or (II), or a pharmaceutically acceptable salt or solvate thereof, wherein (A) is phenyl optionally substituted with 1, 2, or 3 $R_7$. In some embodiments is a compound of Formula (I) or (II), or a pharmaceutically acceptable salt or solvate thereof, wherein (A) is $C_2$-$C_9$heteroaryl optionally substituted with 1, 2, or 3 $R_7$. In some embodiments is a compound of Formula (I) or (II), or a pharmaceutically acceptable salt or solvate thereof, wherein (A) is $C_2$-$C_9$heteroaryl selected from oxazolyl, thiazolyl, pyrazolyl, furanyl, thienyl, pyrrolyl, imidazolyl, triazolyl, isoxazolyl, isothiazolyl, pyridinyl, pyrimidinyl, pyrazinyl, and pyridazinyl, wherein oxazolyl, thiazolyl, pyrazolyl, furanyl, thienyl, pyrrolyl, imidazolyl, triazolyl, isoxazolyl, isothiazolyl, pyridinyl, pyrimidinyl, pyrazinyl, and pyridazinyl are optionally substituted with 1, 2, or 3 $R_7$. In some embodiments is a compound of Formula (I) or (II), or a pharmaceutically acceptable salt or solvate thereof, wherein $R_7$ is selected from halogen, $C_1$-$C_6$alkyl, $C_1$-$C_6$haloalkyl, $C_1$-$C_6$alkoxy, and —CN. In some embodiments is a compound of Formula (I) or (II), or a pharmaceutically acceptable salt or solvate thereof, wherein (A) is $C_2$-$C_9$heteroaryl selected from:

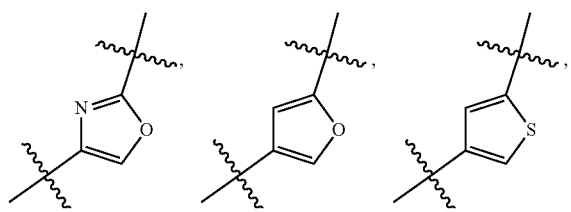

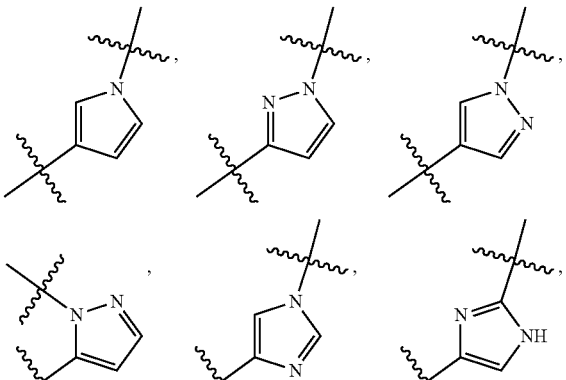

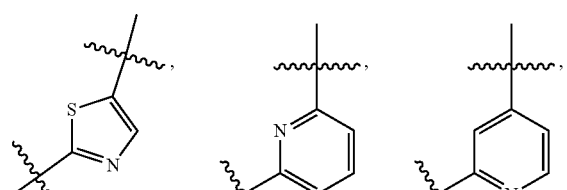

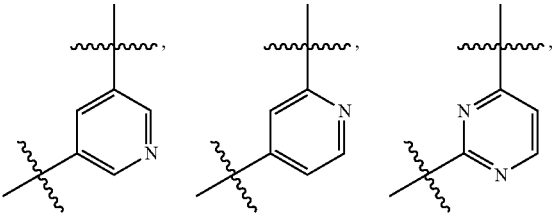

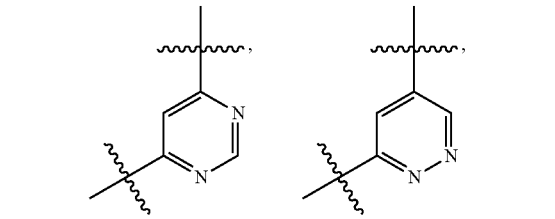

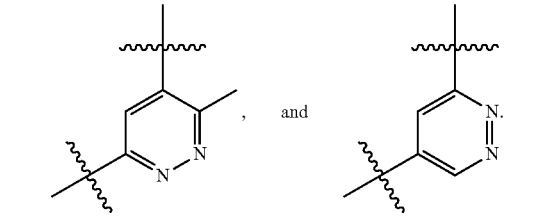

and

In some embodiments is a compound of Formula (I) or (II), or a pharmaceutically acceptable salt or solvate thereof, wherein (A) is $C_2$-$C_9$heterocycloalkyl optionally substituted with 1, 2, or 3 $R_7$. In some embodiments is a compound of Formula (I) or (II), or a pharmaceutically acceptable salt or solvate thereof, wherein Ⓐ is $C_3$-$C_6$cycloalkyl optionally substituted with 1, 2, 3, or 4 $R_7$. In some embodiments is a compound of Formula (I) or (II), or a pharmaceutically acceptable salt or solvate thereof, wherein $R_7$ is selected from halogen, $C_1$-$C_6$alkyl, $C_1$-$C_6$haloalkyl, $C_1$-$C_6$alkoxy, and oxo. In some embodiments is a compound of Formula (I) or (II), or a pharmaceutically acceptable salt or solvate thereof, wherein Ⓐ is $C_2$-$C_9$heterocycloalkyl selected from:

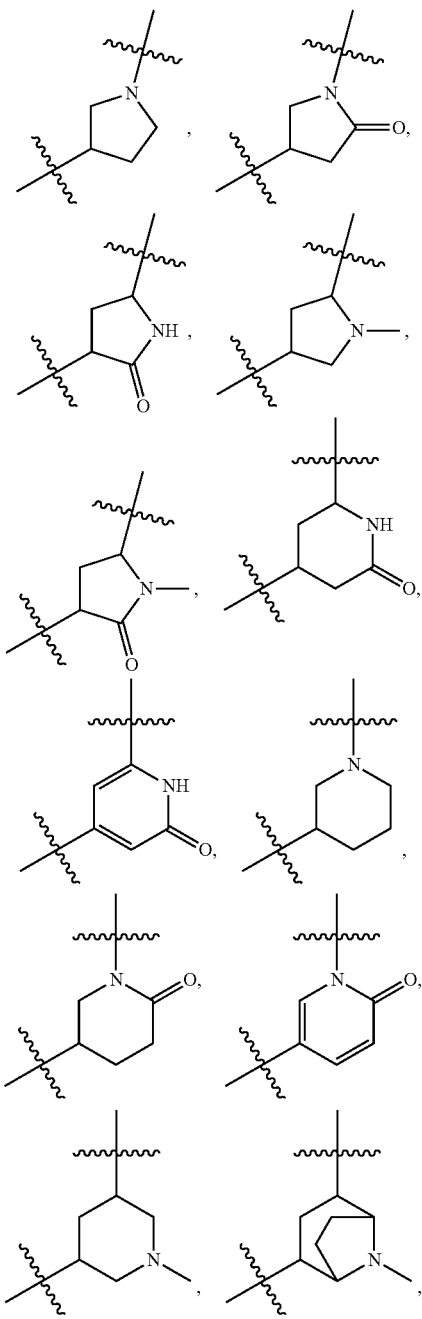

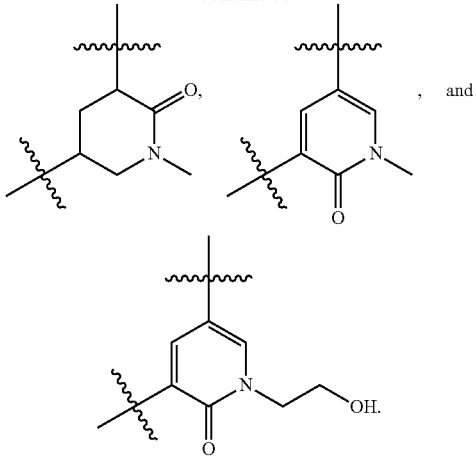

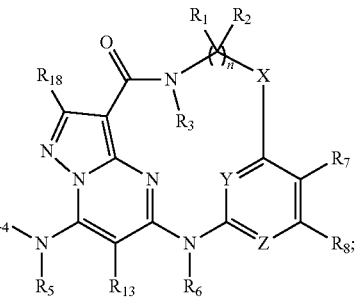

In some embodiments is a compound of Formula (I) or (II), or a pharmaceutically acceptable salt or solvate thereof, wherein $L_1$ is —C(O)N($R_3$)—. In some embodiments is a compound of Formula (I) or (II), or a pharmaceutically acceptable salt or solvate thereof, wherein $L_2$ is —N($R_6$)—.

In another aspect, provided herein are compounds of Formula (III) or Formula (IV):

Formula (III)

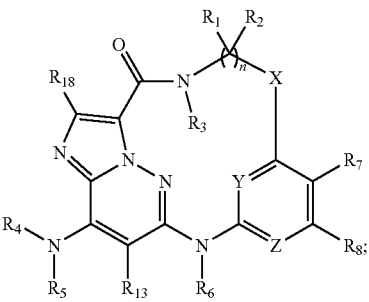

Formula (IV)

wherein:
X is —O— or —C($R_9$)($R_{10}$)—;
Y is =N— or =C($R_{15}$)—;
Z is =N— or =C($R_{16}$)—;
each $R_1$ is independently selected from hydrogen, deuterium, $C_1$-$C_6$alkyl, and $C_1$-$C_6$deuteroalkyl;
each $R_2$ is independently selected from hydrogen, deuterium, $C_1$-$C_6$alkyl, and $C_1$-$C_6$deuteroalkyl;
$R_3$ is hydrogen or $C_1$-$C_6$alkyl;
$R_4$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

R₅ is selected from hydrogen, deuterium, C₁-C₆alkyl, C₁-C₆deuteroalkyl, C₁-C₆heteroalkyl, C₃-C₆cycloalkyl, and C₂-C₉heterocycloalkyl;

R₁₃ is hydrogen, deuterium, C₁-C₆alkyl, or C₁-C₆deuteroalkyl; or R₅ and R₁₃ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, C₁-C₆alkyl, C₁-C₆haloalkyl, C₁-C₆alkoxy, and C₁-C₆haloalkoxy;

R₆ is hydrogen or C₁-C₆alkyl;

R₇ and R₈ are independently selected from hydrogen, deuterium, halogen, C₁-C₆alkyl, C₁-C₆deuteroalkyl, —C₁-C₆alkyl-OH, C₁-C₆haloalkyl, C₁-C₆alkoxy, C₃-C₆cycloalkyl, C₂-C₉heterocycloalkyl, C₂-C₉heteroaryl, C₆-C₁₀aryl, —OR₁₁, —N(R₁₁)₂, —CN, —C(=O)R₁₂, —C(=O)OR₁₁, —C(=O)N(R₁₁)₂, —NR₁₁C(=O)R₁₂, —NR₁₁S(=O)₂R₁₂, —S(=O)₂R₁₂, and —S(=O)₂N(R₁₁)₂, wherein C₃-C₆cycloalkyl, C₂-C₉heterocycloalkyl, C₂-C₉heteroaryl, or C₆-C₁₀aryl are optionally substituted with 1, 2, or 3 groups selected from halogen, C₁-C₆alkyl, C₁-C₆haloalkyl, C₁-C₆alkoxy, and C₁-C₆haloalkoxy;

R₉ and R₁₀ are independently selected from hydrogen, deuterium, C₁-C₆alkyl, and C₁-C₆deuteroalkyl;

each R₁₁ is independently selected from hydrogen, C₁-C₆alkyl, C₁-C₆haloalkyl, C₁-C₆heteroalkyl, and phenyl, wherein phenyl is optionally substituted with 1, 2, or 3 groups selected from halogen, C₁-C₆alkyl, C₁-C₆haloalkyl, C₁-C₆alkoxy, C₁-C₆haloalkoxy, C₂-C₉heterocycloalkyl, C₂-C₉heteroaryl, —OR₁₄, —N(R₁₄)₂, —C(=O)OR₁₄, and —C(=O)N(R₁₄)₂;

each R₁₂ is independently selected from C₁-C₆alkyl and C₁-C₆heteroalkyl;

each R₁₄ is independently selected from hydrogen, C₁-C₆alkyl, and C₁-C₆haloalkyl;

R₁₅ and R₁₆ are independently selected from hydrogen, deuterium, halogen, C₁-C₆alkyl, C₁-C₆deuteroalkyl, C₁-C₆haloalkyl, C₁-C₆alkoxy, C₁-C₆heteroalkyl, —OR₁₁, —N(R₁₁)₂, —CN, —C(=O)R₁₂, —C(=O)OR₁₁, —C(=O)N(R₁₁)₂, —NR₁₁C(=O)R₁₂, —NR₁₁S(=O)₂R₁₂, —S(=O)₂R₁₂, and —S(=O)₂N(R₁₁)₂;

R₁₈ is hydrogen, deuterium, halogen, C₁-C₆alkyl, or C₁-C₆deuteroalkyl; and n is 1, 2, 3, or 4;

or a pharmaceutically acceptable salt or solvate thereof.

In some embodiments is a compound of Formula (III), or a pharmaceutically acceptable salt or solvate thereof:

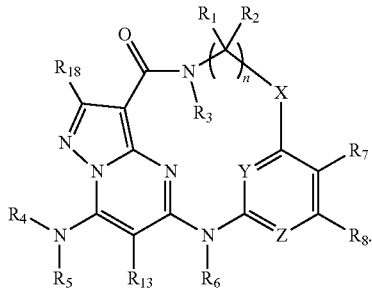

Formula (III)

In some embodiments is a compound of Formula (IV), or a pharmaceutically acceptable salt or solvate thereof:

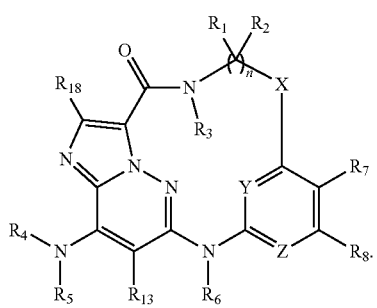

Formula (IV)

In some embodiments is a compound of Formula (III) or (IV), or a pharmaceutically acceptable salt or solvate thereof, wherein Y is =C(R₁₅)— and Z is =C(R₁₆)—. In some embodiments is a compound of Formula (III) or (IV), or a pharmaceutically acceptable salt or solvate thereof, wherein Y is =N— and Z is =C(R₁₆)—. In some embodiments is a compound of Formula (III) or (IV), or a pharmaceutically acceptable salt or solvate thereof, wherein R₁₆ is selected from hydrogen, halogen, C₁-C₆alkyl, C₁-C₆haloalkyl, C₁-C₆alkoxy, and —CN. In some embodiments is a compound of Formula (III) or (IV), or a pharmaceutically acceptable salt or solvate thereof, wherein R₁₆ is selected from hydrogen, halogen, or C₁-C₆alkyl. In some embodiments is a compound of Formula (III) or (IV), or a pharmaceutically acceptable salt or solvate thereof, wherein Y is =C(R₁₅)— and Z is =N—. In some embodiments is a compound of Formula (III) or (IV), or a pharmaceutically acceptable salt or solvate thereof, wherein R₁₅ is selected from hydrogen, halogen, C₁-C₆alkyl, C₁-C₆haloalkyl, C₁-C₆alkoxy, and —CN. In some embodiments is a compound of Formula (III) or (IV), or a pharmaceutically acceptable salt or solvate thereof, wherein R₁₅ is selected from hydrogen, halogen, or C₁-C₆alkyl. In some embodiments is a compound of Formula (III) or (IV), or a pharmaceutically acceptable salt or solvate thereof, wherein Y is =N— and Z is =N—.

In some embodiments is a compound of Formula (I), (II), (III), or (IV), or a pharmaceutically acceptable salt or solvate thereof, wherein X is —O—. In some embodiments is a compound of Formula (I), (II), (III), or (IV), or a pharmaceutically acceptable salt or solvate thereof, wherein X is —C(R₉)(R₁₀)—. In some embodiments is a compound of Formula (I), (II), (III), or (IV), or a pharmaceutically acceptable salt or solvate thereof, wherein R₉ and R₁₀ are hydrogen. In some embodiments is a compound of Formula (I), (II), (III), or (IV), or a pharmaceutically acceptable salt or solvate thereof, wherein R₇ and R₈ are independently selected from hydrogen, halogen, C₁-C₆alkyl, —C₁-C₆haloalkyl, C₁-C₆alkoxy, C₂-C₉heteroaryl, —OR₁₁, —N(R₁₁)₂, —CN, —C(=O)OR₁₁, —C(=O)N(R₁₁)₂, —NR₁₁C(=O)R₁₂, —NR₁₁S(=O)₂R₁₂, —S(=O)₂R₁₂, and —S(=O)₂N(R₁₁)₂, wherein C₂-C₉heteroaryl is optionally substituted with 1, 2, or 3 groups selected from halogen, C₁-C₆alkyl, C₁-C₆haloalkyl, C₁-C₆alkoxy, and C₁-C₆haloalkoxy. In some embodiments is a compound of Formula (I), (II), (III), or (IV), or a pharmaceutically acceptable salt or solvate thereof, wherein R₇ and R₈ are independently selected from hydrogen, halogen, C₁-C₆alkyl, —C₁-C₆haloalkyl, C₂-C₉heteroaryl, —OR₁₁, —CN, —C(=O)N(R₁₁)₂, —NR₁₁S(=O)₂R₁₂, wherein C₂-C₉heteroaryl is optionally substituted with 1 or 2 groups selected from halogen or C₁-C₆alkyl. In some embodiments is a compound of Formula (I), (II), (III), or (IV), or a pharmaceutically acceptable salt or solvate thereof, wherein $R_7$ and $R_8$ are independently selected from hydrogen, halogen, and $C_1$-$C_6$alkyl. In some embodiments is a compound of Formula (I), (II), (III), or (IV), or a pharmaceutically acceptable salt or solvate thereof, wherein $R_4$ and $R_5$ are independently selected from hydrogen and $C_1$-$C_6$alkyl. In some embodiments is a compound of Formula (I), (II), (III), or (IV), or a pharmaceutically acceptable salt or solvate thereof, wherein $R_4$ is hydrogen and $R_5$ is $C_1$-$C_6$alkyl. In some embodiments is a compound of Formula (I), (II), (III), or (IV), or a pharmaceutically acceptable salt or solvate thereof, wherein $R_3$ is hydrogen. In some embodiments is a compound of Formula (I), (II), (III), or (IV), or a pharmaceutically acceptable salt or solvate thereof, wherein $R_6$ is hydrogen. In some embodiments is a compound of Formula (I), (II), (III), or (IV), or a pharmaceutically acceptable salt or solvate thereof, wherein n is 1. In some embodiments is a compound of Formula (I), (II), (III), or (IV), or a pharmaceutically acceptable salt or solvate thereof, wherein n is 2. In some embodiments is a compound of Formula (I), (II), (III), or (IV), or a pharmaceutically acceptable salt or solvate thereof, wherein n is 3. In some embodiments is a compound of Formula (I), (II), (III), or (IV), or a pharmaceutically acceptable salt or solvate thereof, wherein $R_1$ is hydrogen. In some embodiments is a compound of Formula (I), (II), (III), or (IV), or a pharmaceutically acceptable salt or solvate thereof, wherein $R_2$ is hydrogen. In some embodiments is a compound of Formula (I), (II), (III), or (IV), or a pharmaceutically acceptable salt or solvate thereof, wherein $R_{18}$ is hydrogen.

In another aspect described herein is a pharmaceutical composition comprising a compound of Formula (I), (II), (III) or (IV), or a pharmaceutically acceptable salt or solvate thereof, and a pharmaceutically acceptable excipient.

In another aspect described herein is a method of treating an inflammatory or autoimmune disease in a patient in need thereof, comprising administering to the patient a therapeutically effective amount of a compound of Formula (I), (II), (III) or (IV), or a pharmaceutically acceptable salt or solvate thereof. In some embodiments is a method of treating an inflammatory or autoimmune disease in a patient in need thereof, comprising administering to the patient a therapeutically effective amount of a compound of Formula (I), (II), (III) or (IV), or a pharmaceutically acceptable salt or solvate thereof, wherein the disease is selected from rheumatoid arthritis, multiple sclerosis, psoriasis, lupus, intestinal bowel disease, Crohn's disease, ulcerative colitis, ankylosing spondylitis, vitiligo, and atopic dermatitis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl"

group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

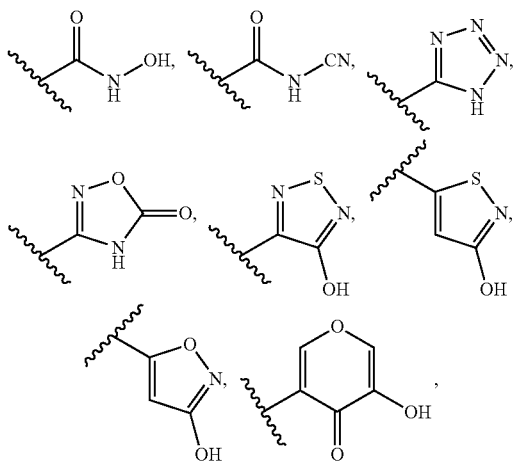

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "deuteroalkyl" refers to an alkyl group that is substituted with one or more deuteriums.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$O—$CH_3$, —$CH_2$—$CH_2$O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2$H, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each R is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

As used herein, the term "about" or "approximately" means within 20%, preferably within 10%, and more preferably within 5% of a given value or range.

The term a "therapeutically effective amount" as used herein refers to the amount of a TYK2 pseudokinase ligand that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "patient" or "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

The term "soft-drug" as used herein, refers to drug substance and/or a chemical compound that is biologically active in the desired target tissue and that is metabolized, after exerting its effect in the target tissue, to a compound that is inactive against the biological target. In some embodiments, the soft-drug has no target biological activity in systemic circulation.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

TYK2 Pseudokinase Ligands

As a member of the JAK family of tyrosine kinases, TYK2 mediates the signaling of pro-inflammatory cytokines and therefore represents a target for treating various inflammatory and autoimmune diseases. The hallmark structural feature of the JAK family is the pseudokinase (JH2) domain immediately N-terminal to the catalytic domain (JH1). Although the JH2 domain shares the overall fold of a typical catalytic domain, a series of individual residue and conformational differences between the TYK2 JH1 and JH2 domains points to the lack of catalytic activity of the JH2 domain. The JH2 domains of the JAK family have been shown to regulate the function of the JH1 domains. The overall body of evidence is consistent with the TYK2 pseudokinase domain being auto-inhibitory, stabilizing the inactivated state of the kinase domain and that small molecule ligands can stabilize this auto-inhibitory conformation thereby preventing protein function in an allosteric manner (Moslin et al., Med. Chem. Commun., 2017, 700-712).

The compounds of Formula (I), (II), (III), (IIIa), (IIIb), (IIIc), (IIId), (IV), (IVa), (IVb), (IVc), or (IVd) described herein are TYK2 pseudokinase ligands. The compounds of Formula (I), (II), (III), (IIIa), (IIIb), (IIIc), (IIId), (IV), (IVa), (IVb), (IVc), or (IVd) described herein, and compositions comprising these compounds, are useful for the treatment of an inflammatory or autoimmune disease.

In some embodiments, provided herein is a compound of Formula (I), or a pharmaceutically acceptable salt or solvate thereof:

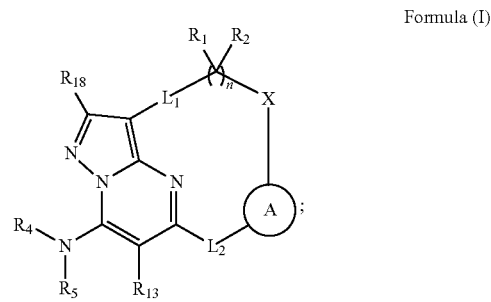

Formula (I)

wherein:

$\bigcirc\!\!\!\!A$ is $C_3$-$C_6$cycloalkyl, $C_6$-$C_{10}$aryl, $C_2$-$C_9$heterocycloalkyl, or $C_2$-$C_9$heteroaryl, wherein $C_3$-$C_6$cycloalkyl, $C_6$-$C_{10}$aryl, $C_2$-$C_9$heterocycloalkyl, or $C_2$-$C_9$heteroaryl is optionally substituted with 1, 2, 3, or 4 $R_7$;

X is —O—, —C($R_9$)($R_{10}$)—, —C($R_9$)($R_{10}$)—O—, —O—C($R_9$)($R_{10}$), —C(O)—, —C(O)N($R_3$)—, —N($R_3$)C(O)—, or —N($R_{17}$)—;

$L_1$ is —C(O)N($R_3$)—, —N($R_3$)C(O)—, —C($R_9$)($R_{10}$)—O—, or —O—C($R_9$)($R_{10}$)—;

$L_2$ is —N($R_6$)—, —N($R_6$)CH$_2$—, or —CH$_2$N($R_6$)—;

each $R_1$ is independently selected from hydrogen, deuterium, $C_1$-$C_6$alkyl, and $C_1$-$C_6$deuteroalkyl;

each $R_2$ is independently selected from hydrogen, deuterium, $C_1$-$C_6$alkyl, and $C_1$-$C_6$deuteroalkyl; or $R_1$ and $R_2$ are combined to form a 3-, 4-, 5-, or 6-membered cycloalkyl ring or a 4-, 5-, or 6-membered heterocycloalkyl ring;

each $R_3$ is independently hydrogen or $C_1$-$C_6$alkyl; or $R_2$ and $R_3$ together with the atoms to which they are attached are combined to form a 5- or 6-membered heterocycloalkyl ring optionally substituted 1, 2, or 3 with groups selected from halogen, —OH, $C_1$-$C_6$alkyl, and —$C_1$-$C_6$alkyl-OH;

R₄ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

R₅ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

R₁₃ is hydrogen, deuterium, $C_1$-$C_6$alkyl, or $C_1$-$C_6$deuteroalkyl; or R₅ and R₁₃ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

R₆ is hydrogen or $C_1$-$C_6$alkyl;

each R₇ is independently selected from deuterium, halogen, $C_1$-$C_6$alkyl, $C_1$-$C_6$deuteroalkyl, $C_1$-$C_6$haloalkyl, $C_1$-$C_6$alkoxy, $C_1$-$C_6$heteroalkyl, oxo, —OR₁₁, —N(R₁₁)₂, —CN, —C(=O)R₁₂, —C(=O)OR₁₁, —C(=O)N(R₁₁)₂, —NR₁₁C(=O)R₁₂, —NR₁₁S(=O)₂R₁₂, —S(=O)₂R₁₂, and —S(=O)₂N(R₁₁)₂;

each R₉ and each R₁₀ are independently selected from hydrogen, deuterium, $C_1$-$C_6$alkyl, and $C_1$-$C_6$deuteroalkyl;

each R₁₁ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —OR₁₄, —N(R₁₄)₂, —C(=O)OR₁₄, and —C(=O)N(R₁₄)₂;

each R₁₂ is independently selected from $C_1$-$C_6$alkyl and $C_1$-$C_6$heteroalkyl;

each R₁₄ is independently selected from hydrogen, $C_1$-$C_6$alkyl, and $C_1$-$C_6$haloalkyl;

R₁₇ is hydrogen or $C_1$-$C_6$alkyl;

R₁₈ is hydrogen, deuterium, halogen, $C_1$-$C_6$alkyl, or $C_1$-$C_6$deuteroalkyl; and n is 1, 2, 3, or 4.

In some embodiments is a compound of Formula (I), or a pharmaceutically acceptable salt or solvate thereof, wherein (A) is $C_6$-$C_{10}$aryl optionally substituted with 1, 2, or 3 R₇. In some embodiments is a compound of Formula (I), or a pharmaceutically acceptable salt or solvate thereof, wherein (A) is phenyl optionally substituted with 1, 2, or 3 R₇. In some embodiments is a compound of Formula (I), or a pharmaceutically acceptable salt or solvate thereof, wherein (A) is $C_2$-$C_9$heteroaryl optionally substituted with 1, 2, or 3 R₇. In some embodiments is a compound of Formula (I), or a pharmaceutically acceptable salt or solvate thereof, wherein (A) is $C_2$-$C_9$heteroaryl selected from oxazolyl, thiazolyl, pyrazolyl, furanyl, thienyl, pyrrolyl, imidazolyl, triazolyl, isoxazolyl, isothiazolyl, pyridinyl, pyrimidinyl, pyrazinyl, and pyridazinyl, wherein oxazolyl, thiazolyl, pyrazolyl, furanyl, thienyl, pyrrolyl, imidazolyl, triazolyl, isoxazolyl, isothiazolyl, pyridinyl, pyrimidinyl, pyrazinyl, and pyridazinyl are optionally substituted with 1, 2, or 3 R₇, wherein R₇ is selected from halogen, $C_1$-$C_6$alkyl, $C_1$-$C_6$haloalkyl, $C_1$-$C_6$alkoxy, and —CN. In some embodiments is a compound of Formula (I), or a pharmaceutically acceptable salt or solvate thereof, wherein (A) is $C_2$-$C_9$heteroaryl selected from:

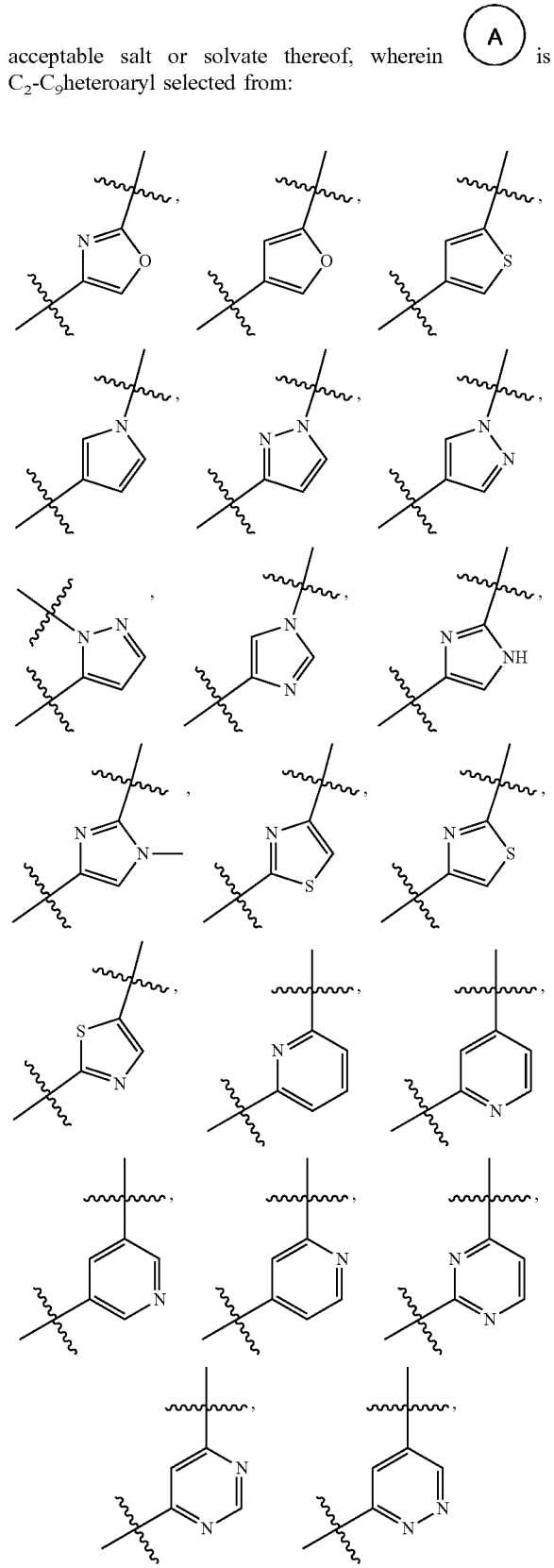

-continued

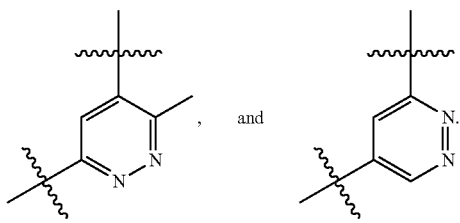

In some embodiments is a compound of Formula (I), or a pharmaceutically acceptable salt or solvate thereof, wherein (A) is $C_2$-$C_9$heterocycloalkyl optionally substituted with 1, 2, or 3 $R_7$. In some embodiments is a compound of Formula (I), or a pharmaceutically acceptable salt or solvate thereof, wherein (A) is $C_3$-$C_6$cycloalkyl optionally substituted with 1, 2, 3, or 4 $R_7$. In some embodiments is a compound of Formula (I), or a pharmaceutically acceptable salt or solvate thereof, wherein $R_7$ is selected from halogen, $C_1$-$C_6$alkyl, $C_1$-$C_6$haloalkyl, $C_1$-$C_6$alkoxy, and oxo. In some embodiments is a compound of Formula (I), or a pharmaceutically acceptable salt or solvate thereof, wherein (A) is $C_2$-$C_9$heterocycloalkyl selected from:

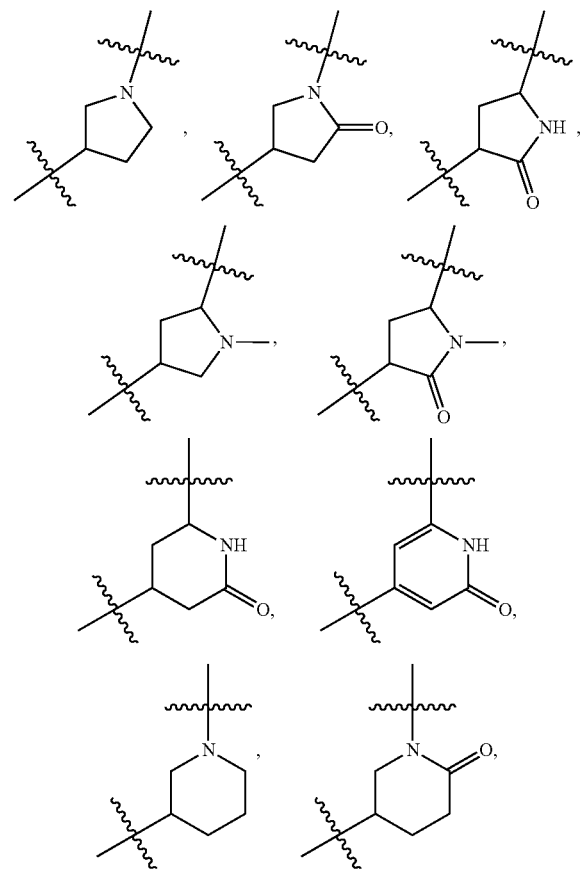

-continued

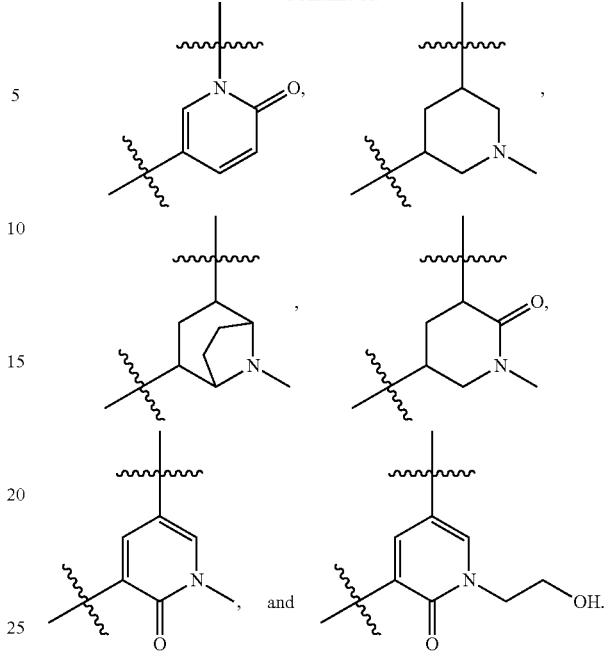

In some embodiments is a compound of Formula (I), or a pharmaceutically acceptable salt or solvate thereof, wherein $L_1$ is —C(O)N($R_3$)—. In some embodiments is a compound of Formula (I), or a pharmaceutically acceptable salt or solvate thereof, wherein $L_1$ is —N($R_3$)C(O)—. In some embodiments is a compound of Formula (I), or a pharmaceutically acceptable salt or solvate thereof, wherein $L_1$ is —C($R_9$)($R_{10}$)—O—. In some embodiments is a compound of Formula (I), or a pharmaceutically acceptable salt or solvate thereof, wherein $L_1$ is —O—C($R_9$)($R_{10}$)—.

In some embodiments is a compound of Formula (I), or a pharmaceutically acceptable salt or solvate thereof, wherein $L_2$ is —N($R_6$)—. In some embodiments is a compound of Formula (I), or a pharmaceutically acceptable salt or solvate thereof, wherein $L_2$ is —N(H)—. In some embodiments is a compound of Formula (I), or a pharmaceutically acceptable salt or solvate thereof, wherein $L_2$ is —N($R_6$)$CH_2$—. In some embodiments is a compound of Formula (I), or a pharmaceutically acceptable salt or solvate thereof, wherein $L_2$ is —N(H)$CH_2$—. In some embodiments is a compound of Formula (I), or a pharmaceutically acceptable salt or solvate thereof, wherein $L_2$ is —$CH_2$N($R_6$)—. In some embodiments is a compound of Formula (I), or a pharmaceutically acceptable salt or solvate thereof, wherein $L_2$ is —$CH_2$N(H)—.

In some embodiments is a compound of Formula (I), or a pharmaceutically acceptable salt or solvate thereof, wherein X is —O—. In some embodiments is a compound of Formula (I), or a pharmaceutically acceptable salt or solvate thereof, wherein X is —O— and n is 2. In some embodiments is a compound of Formula (I), or a pharmaceutically acceptable salt or solvate thereof, wherein X is —O—, n is 2, and each $R_1$ and each $R_2$ are hydrogen. In some embodiments is a compound of Formula (I), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (I), or a pharmaceutically acceptable salt or solvate thereof, wherein X is —O— and n is 3. In some embodiments is a compound of Formula (I), or a pharmaceutically acceptable salt or solvate thereof, wherein X is —O—, n is 3, and each $R_1$ and each $R_2$ are hydrogen. In some embodiments is a compound of Formula (I), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (I), or a pharmaceutically acceptable salt or solvate thereof, wherein X is —C($R_9$)($R_{10}$)—. In some embodiments is a compound of Formula (I), or a pharmaceutically acceptable salt or solvate thereof, wherein X is —$CH_2$—. In some embodiments is a compound of Formula (I), or a pharmaceutically acceptable salt or solvate thereof, wherein X is —$CH_2$— and n is 1. In some embodiments is a compound of Formula (I), or a pharmaceutically acceptable salt or solvate thereof, wherein X is —$CH_2$—, n is 1, and $R_1$ and $R_2$ are hydrogen. In some embodiments is a compound of Formula (I), or a pharmaceutically acceptable salt or solvate thereof, wherein X is —$CH_2$— and n is 2. In some embodiments is a compound of Formula (I), or a pharmaceutically acceptable salt or solvate thereof, wherein X is —$CH_2$—, n is 2, and each $R_1$ and each $R_2$ are hydrogen. In some embodiments is a compound of Formula (I), or a pharmaceutically acceptable salt or solvate thereof, wherein X is —$CH_2$— and n is 3. In some embodiments is a compound of Formula (I), or a pharmaceutically acceptable salt or solvate thereof, wherein X is —$CH_2$—, n is 3, and each $R_1$ and each $R_2$ are hydrogen.

In some embodiments is a compound of Formula (I), or a pharmaceutically acceptable salt or solvate thereof, wherein X is —N($R_{17}$)—. In some embodiments is a compound of Formula (I), or a pharmaceutically acceptable salt or solvate thereof, wherein X is —N(H)—. In some embodiments is a compound of Formula (I), or a pharmaceutically acceptable salt or solvate thereof, wherein X is —N(H)— and n is 1. In some embodiments is a compound of Formula (I), or a pharmaceutically acceptable salt or solvate thereof, wherein X is —N(H)—, n is 1, and $R_1$ and $R_2$ are hydrogen. In some embodiments is a compound of Formula (I), or a pharmaceutically acceptable salt or solvate thereof, wherein X is —N(H)— and n is 2. In some embodiments is a compound of Formula (I), or a pharmaceutically acceptable salt or solvate thereof, wherein X is —N(H)—, n is 2, and each $R_1$ and each $R_2$ are hydrogen. In some embodiments is a compound of Formula (I), or a pharmaceutically acceptable salt or solvate thereof, wherein X is —N(H)— and n is 3. In some embodiments is a compound of Formula (I), or a pharmaceutically acceptable salt or solvate thereof, wherein X is —N(H)—, n is 3, and each $R_1$ and each $R_2$ are hydrogen.

In some embodiments is a compound of Formula (I), or a pharmaceutically acceptable salt or solvate thereof, wherein X is —C($R_9$)($R_{10}$)—O—. In some embodiments is a compound of Formula (I), or a pharmaceutically acceptable salt or solvate thereof, wherein X is —$CH_2$O— and n is 1. In some embodiments is a compound of Formula (I), or a pharmaceutically acceptable salt or solvate thereof, wherein X is —$CH_2$O—, n is 1, and $R_1$ and $R_2$ are hydrogen. In some embodiments is a compound of Formula (I), or a pharmaceutically acceptable salt or solvate thereof, wherein X is —$CH_2$O— and n is 2. In some embodiments is a compound of Formula (I), or a pharmaceutically acceptable salt or solvate thereof, wherein X is —$CH_2$O—, n is 2, and each $R_1$ and each $R_2$ are hydrogen. In some embodiments is a compound of Formula (I), or a pharmaceutically acceptable salt or solvate thereof, wherein X is —$CH_2$O— and n is 3.

In some embodiments is a compound of Formula (I), or a pharmaceutically acceptable salt or solvate thereof, wherein X is —$CH_2$O—, n is 3, and each $R_1$ and each $R_2$ are hydrogen.

In some embodiments is a compound of Formula (I), or a pharmaceutically acceptable salt or solvate thereof, wherein $R_4$ is selected from hydrogen and $C_1$-$C_6$alkyl. In some embodiments is a compound of Formula (I), or a pharmaceutically acceptable salt or solvate thereof, wherein $R_4$ is hydrogen. In some embodiments is a compound of Formula (I), or a pharmaceutically acceptable salt or solvate thereof, wherein $R_4$ is $C_1$-$C_6$alkyl.

In some embodiments is a compound of Formula (I), or a pharmaceutically acceptable salt or solvate thereof, wherein $R_5$ is selected from hydrogen and $C_1$-$C_6$alkyl. In some embodiments is a compound of Formula (I), or a pharmaceutically acceptable salt or solvate thereof, wherein $R_5$ is hydrogen. In some embodiments is a compound of Formula (I), or a pharmaceutically acceptable salt or solvate thereof, wherein $R_5$ is $C_1$-$C_6$alkyl.

In some embodiments is a compound of Formula (I), or a pharmaceutically acceptable salt or solvate thereof, wherein $R_{13}$ is hydrogen. In some embodiments is a compound of Formula (I), or a pharmaceutically acceptable salt or solvate thereof, wherein $R_5$ and $R_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy. In some embodiments is a compound of Formula (I), or a pharmaceutically acceptable salt or solvate thereof, wherein $R_5$ and $R_{13}$ together with the atoms to which they are attached are combined to form a 5- or 6-membered heterocycloalkyl ring, wherein the 5- or 6-membered heterocycloalkyl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy. In some embodiments is a compound of Formula (I), or a pharmaceutically acceptable salt or solvate thereof, wherein $R_5$ and $R_{13}$ together with the atoms to which they are attached are combined to form a 5- or 6-membered heteroaryl ring, wherein the 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy.

In some embodiments is a compound of Formula (I), or a pharmaceutically acceptable salt or solvate thereof, wherein $R_4$ is hydrogen and $R_5$ is $C_1$-$C_6$alkyl. In some embodiments is a compound of Formula (I), or a pharmaceutically acceptable salt or solvate thereof, wherein $R_4$ and $R_5$ are hydrogen. In some embodiments is a compound of Formula (I), or a pharmaceutically acceptable salt or solvate thereof, wherein $R_4$ and $R_5$ are $C_1$-$C_6$alkyl.

In some embodiments is a compound of Formula (I), or a pharmaceutically acceptable salt or solvate thereof, wherein each $R_3$ is hydrogen. In some embodiments is a compound of Formula (I), or a pharmaceutically acceptable salt or solvate thereof, wherein each $R_3$ is $C_1$-$C_6$alkyl. In some embodiments is a compound of Formula (I), or a pharmaceutically acceptable salt or solvate thereof, wherein $R_2$ and $R_3$ together with the atoms to which they are attached are combined to form a 5- or 6-membered heterocycloalkyl ring optionally substituted 1, 2, or 3 with groups selected from halogen, —OH, $C_1$-$C_6$alkyl, and —$C_1$-$C_6$alkyl-OH.

In some embodiments is a compound of Formula (I), or a pharmaceutically acceptable salt or solvate thereof, wherein $R_{18}$ is hydrogen. In some embodiments is a compound of Formula (I), or a pharmaceutically acceptable salt or solvate thereof, wherein $R_{18}$ is deuterium. In some embodiments is a compound of Formula (I), or a pharmaceutically acceptable salt or solvate thereof, wherein $R_{18}$ is halogen. In some embodiments is a compound of Formula (I), or a pharmaceutically acceptable salt or solvate thereof, wherein $R_{18}$ is $C_1$-$C_6$alkyl. In some embodiments is a compound of Formula (I), or a pharmaceutically acceptable salt or solvate thereof, wherein $R_{18}$ is $C_1$-$C_6$deuteroalkyl.

In some embodiments, provided herein is a compound of Formula (II), or a pharmaceutically acceptable salt or solvate thereof:

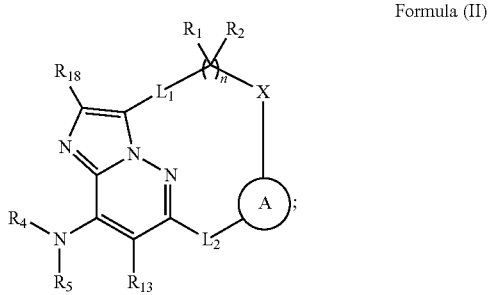

Formula (II)

wherein:

Ⓐ is $C_3$-$C_6$cycloalkyl, $C_6$-$C_{10}$aryl, $C_2$-$C_9$heterocycloalkyl, or $C_2$-$C_9$heteroaryl, wherein $C_3$-$C_6$cycloalkyl, $C_6$-$C_{10}$aryl, $C_2$-$C_9$heterocycloalkyl, or $C_2$-$C_9$heteroaryl is optionally substituted with 1, 2, 3, or 4 $R_7$;

X is —O—, —C($R_9$)($R_{10}$)—, —C($R_9$)($R_{10}$)—O—, —O—C($R_9$)($R_{10}$), —C(O)—, —C(O)N($R_3$)—, —N($R_3$)C(O)—, or —N($R_{17}$)—;

$L_1$ is —C(O)N($R_3$)—, —N($R_3$)C(O)—, —C($R_9$)($R_{10}$)—O—, or —O—C($R_9$)($R_{10}$)—;

$L_2$ is —N($R_6$)—, —N($R_6$)CH$_2$—, or —CH$_2$N($R_6$)—;

each $R_1$ is independently selected from hydrogen, deuterium, $C_1$-$C_6$alkyl, and $C_1$-$C_6$deuteroalkyl;

each $R_2$ is independently selected from hydrogen, deuterium, $C_1$-$C_6$alkyl, and $C_1$-$C_6$deuteroalkyl; or $R_1$ and $R_2$ are combined to form a 3-, 4-, 5-, or 6-membered cycloalkyl ring or a 4-, 5-, or 6-membered heterocycloalkyl ring;

each $R_3$ is independently hydrogen or $C_1$-$C_6$alkyl; or $R_2$ and $R_3$ together with the atoms to which they are attached are combined to form a 5- or 6-membered heterocycloalkyl ring optionally substituted 1, 2, or 3 with groups selected from halogen, —OH, $C_1$-$C_6$alkyl, and —$C_1$-$C_6$alkyl-OH;

$R_4$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

$R_5$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

$R_{13}$ is hydrogen, deuterium, $C_1$-$C_6$alkyl, or $C_1$-$C_6$deuteroalkyl; or $R_5$ and $R_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_6$ is hydrogen or $C_1$-$C_6$alkyl;

each $R_7$ is independently selected from deuterium, halogen, $C_1$-$C_6$alkyl, $C_1$-$C_6$deuteroalkyl, $C_1$-$C_6$haloalkyl, $C_1$-$C_6$alkoxy, $C_1$-$C_6$heteroalkyl, oxo, —$OR_{11}$, —$N(R_{11})_2$, —CN, —C(=O)$R_{12}$, —C(=O)$OR_{11}$, —C(=O)$N(R_{11})_2$, —$NR_{11}$C(=O)$R_{12}$, —$NR_{11}$S(=O)$_2$$R_{12}$, —S(=O)$_2$$R_{12}$, and —S(=O)$_2$$N(R_{11})_2$;

each $R_9$ and each $R_{10}$ are independently selected from hydrogen, deuterium, $C_1$-$C_6$alkyl, and $C_1$-$C_6$deuteroalkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_{14}$, and —C(=O)$N(R_{14})_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{17}$ is hydrogen or $C_1$-$C_6$alkyl;

$R_{18}$ is hydrogen, deuterium, halogen, $C_1$-$C_6$alkyl, or $C_1$-$C_6$deuteroalkyl; and n is 1, 2, 3, or 4.

In some embodiments is a compound of Formula (II), or a pharmaceutically acceptable salt or solvate thereof, wherein Ⓐ is $C_6$-$C_{10}$aryl optionally substituted with 1, 2, or 3 $R_7$. In some embodiments is a compound of Formula (II), or a pharmaceutically acceptable salt or solvate thereof, wherein Ⓐ is phenyl optionally substituted with 1, 2, or 3 $R_7$. In some embodiments is a compound of Formula (II), or a pharmaceutically acceptable salt or solvate thereof, wherein Ⓐ is $C_2$-$C_9$heteroaryl optionally substituted with 1, 2, or 3 $R_7$. In some embodiments is a compound of Formula (II), or a pharmaceutically acceptable salt or solvate thereof, wherein Ⓐ is $C_2$-$C_9$heteroaryl selected from oxazolyl, thiazolyl, pyrazolyl, furanyl, thienyl, pyrrolyl, imidazolyl, triazolyl, isoxazolyl, isothiazolyl, pyridinyl, pyrimidinyl, pyrazinyl, and pyridazinyl, wherein oxazolyl, thiazolyl, pyrazolyl, furanyl, thienyl, pyrrolyl, imidazolyl, triazolyl, isoxazolyl, isothiazolyl, pyridinyl, pyrimidinyl, pyrazinyl, and pyridazinyl are optionally substituted with 1, 2, or 3 $R_7$. In some embodiments is a compound of Formula (II), or a pharmaceutically acceptable salt or solvate thereof, wherein $R_7$ is selected from halogen, $C_1$-$C_6$alkyl, $C_1$-$C_6$haloalkyl, $C_1$-$C_6$alkoxy, and —CN. In some embodiments is a compound of Formula (II), or a pharmaceutically acceptable salt or solvate thereof, wherein Ⓐ is $C_2$-$C_9$heteroaryl selected from:

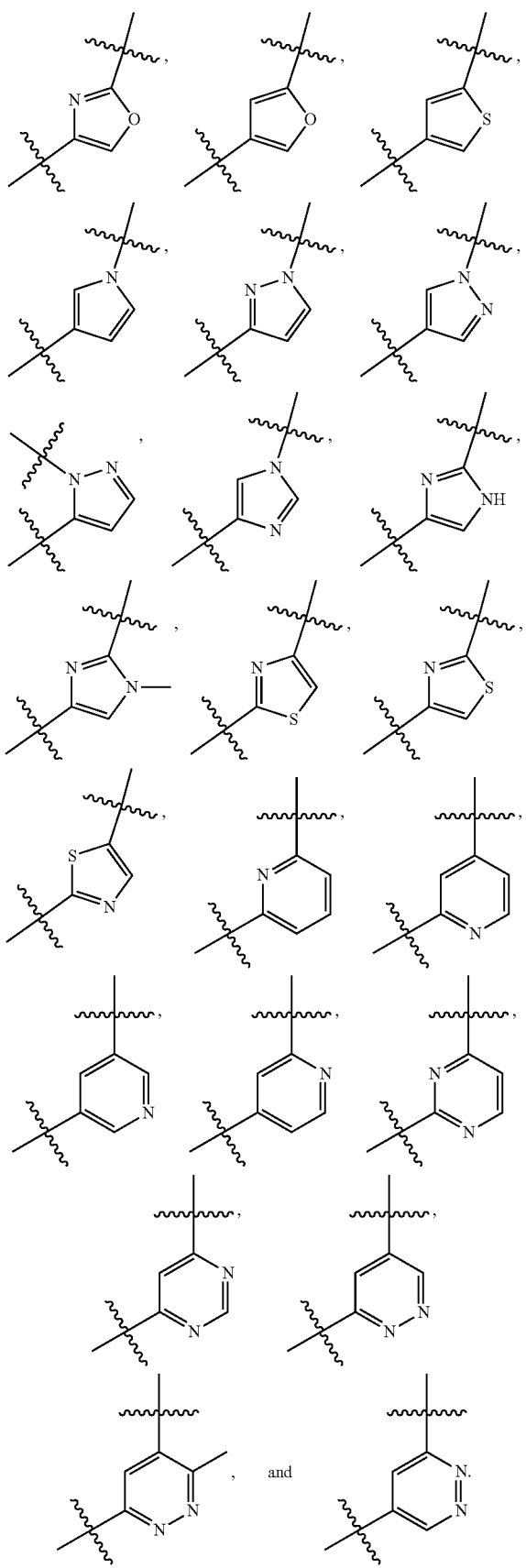

In some embodiments is a compound of Formula (II), or a pharmaceutically acceptable salt or solvate thereof, wherein (A) is $C_2$-$C_9$heterocycloalkyl optionally substituted with 1, 2, or 3 $R_7$. In some embodiments is a compound of Formula (II), or a pharmaceutically acceptable salt or solvate thereof, wherein (A) is $C_3$-$C_6$cycloalkyl optionally substituted with 1, 2, 3, or 4 $R_7$. In some embodiments is a compound of Formula (II), or a pharmaceutically acceptable salt or solvate thereof, wherein $R_7$ is selected from halogen, $C_1$-$C_6$alkyl, $C_1$-$C_6$haloalkyl, $C_1$-$C_6$alkoxy, and oxo. In some embodiments is a compound of Formula (II), or a pharmaceutically acceptable salt or solvate thereof, wherein (A) is $C_2$-$C_9$heterocycloalkyl selected from:

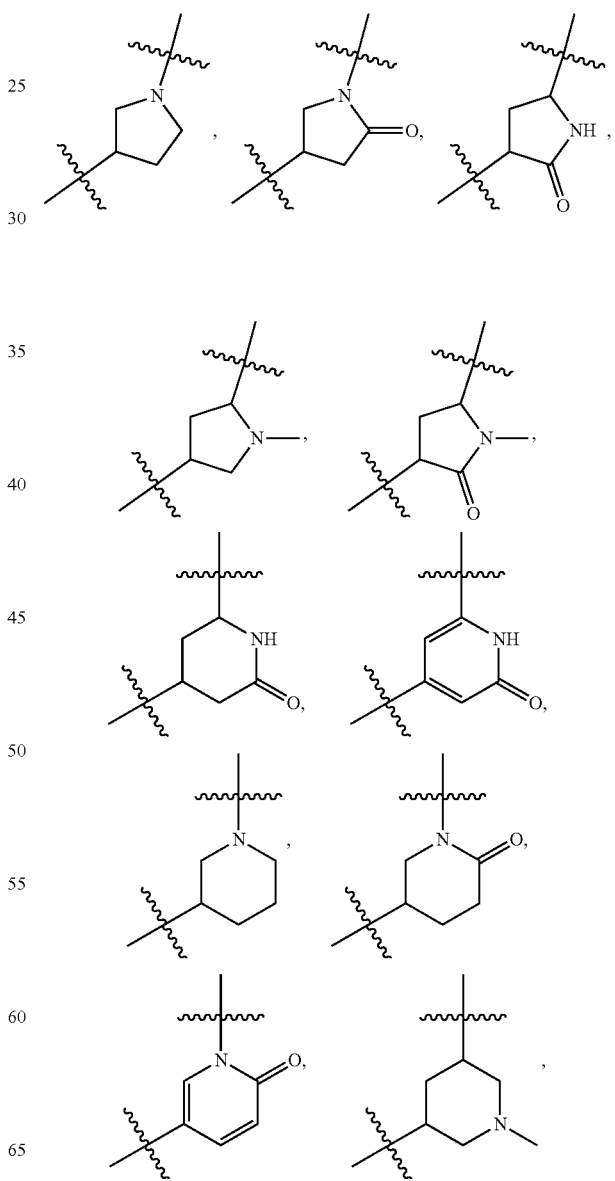

In some embodiments is a compound of Formula (II), or a pharmaceutically acceptable salt or solvate thereof, wherein L$_1$ is —C(O)N(R$_3$)—. In some embodiments is a compound of Formula (II), or a pharmaceutically acceptable salt or solvate thereof, wherein L$_1$ is —N(R$_3$)C(O)—. In some embodiments is a compound of Formula (II), or a pharmaceutically acceptable salt or solvate thereof, wherein L$_1$ is —C(R$_9$)(R$_{10}$)—O—. In some embodiments is a compound of Formula (II), or a pharmaceutically acceptable salt or solvate thereof, wherein L$_1$ is —O—C(R$_9$)(R$_{10}$)—.

In some embodiments is a compound of Formula (II), or a pharmaceutically acceptable salt or solvate thereof, wherein L$_2$ is —N(R$_6$)—. In some embodiments is a compound of Formula (II), or a pharmaceutically acceptable salt or solvate thereof, wherein L$_2$ is —N(H)—. In some embodiments is a compound of Formula (II), or a pharmaceutically acceptable salt or solvate thereof, wherein L$_2$ is —N(R$_6$)CH$_2$—. In some embodiments is a compound of Formula (II), or a pharmaceutically acceptable salt or solvate thereof, wherein L$_2$ is —N(H)CH$_2$—. In some embodiments is a compound of Formula (II), or a pharmaceutically acceptable salt or solvate thereof, wherein L$_2$ is —CH$_2$N(R$_6$)—. In some embodiments is a compound of Formula (II), or a pharmaceutically acceptable salt or solvate thereof, wherein L$_2$ is —CH$_2$N(H)—.

In some embodiments is a compound of Formula (II), or a pharmaceutically acceptable salt or solvate thereof, wherein X is —O—. In some embodiments is a compound of Formula (II), or a pharmaceutically acceptable salt or solvate thereof, wherein X is —O— and n is 2. In some embodiments is a compound of Formula (II), or a pharmaceutically acceptable salt or solvate thereof, wherein X is —O—, n is 2, and each R$_1$ and each R$_2$ are hydrogen. In some embodiments is a compound of Formula (II), or a pharmaceutically acceptable salt or solvate thereof, wherein X is —O—, n is 2, each R$_1$ is hydrogen, and one R$_2$ is hydrogen and one R$_2$ is C$_1$-C$_6$alkyl. In some embodiments is a compound of Formula (II), or a pharmaceutically acceptable salt or solvate thereof, wherein X is —O— and n is 3. In some embodiments is a compound of Formula (II), or a pharmaceutically acceptable salt or solvate thereof, wherein X is —O—, n is 3, and each R$_1$ and each R$_2$ are hydrogen. In some embodiments is a compound of Formula (II), or a pharmaceutically acceptable salt or solvate thereof, wherein X is —O—, n is 3, one R$_1$ is C$_1$-C$_6$alkyl and one R$_2$ is C$_1$-C$_6$alkyl and the remaining R$_1$ and R$_2$ are each hydrogen.

In some embodiments is a compound of Formula (II), or a pharmaceutically acceptable salt or solvate thereof, wherein X is —C(R$_9$)(R$_{10}$)—. In some embodiments is a compound of Formula (II), or a pharmaceutically acceptable salt or solvate thereof, wherein X is —CH$_2$—. In some embodiments is a compound of Formula (II), or a pharmaceutically acceptable salt or solvate thereof, wherein X is —CH$_2$— and n is 1. In some embodiments is a compound of Formula (II), or a pharmaceutically acceptable salt or solvate thereof, wherein X is —CH$_2$—, n is 1, and R$_1$ and R$_2$ are hydrogen. In some embodiments is a compound of Formula (II), or a pharmaceutically acceptable salt or solvate thereof, wherein X is —CH$_2$— and n is 2. In some embodiments is a compound of Formula (II), or a pharmaceutically acceptable salt or solvate thereof, wherein X is —CH$_2$—, n is 2, and each R$_1$ and each R$_2$ are hydrogen. In some embodiments is a compound of Formula (II), or a pharmaceutically acceptable salt or solvate thereof, wherein X is —CH$_2$— and n is 3. In some embodiments is a compound of Formula (II), or a pharmaceutically acceptable salt or solvate thereof, wherein X is —CH$_2$—, n is 3, and each R$_1$ and each R$_2$ are hydrogen.

In some embodiments is a compound of Formula (II), or a pharmaceutically acceptable salt or solvate thereof, wherein X is —N(R$_{17}$)—. In some embodiments is a compound of Formula (II), or a pharmaceutically acceptable salt or solvate thereof, wherein X is —N(H)—. In some embodiments is a compound of Formula (II), or a pharmaceutically acceptable salt or solvate thereof, wherein X is —N(H)— and n is 1. In some embodiments is a compound of Formula (II), or a pharmaceutically acceptable salt or solvate thereof, wherein X is —N(H)—, n is 1, and R$_1$ and R$_2$ are hydrogen. In some embodiments is a compound of Formula (II), or a pharmaceutically acceptable salt or solvate thereof, wherein X is —N(H)— and n is 2. In some embodiments is a compound of Formula (II), or a pharmaceutically acceptable salt or solvate thereof, wherein X is —N(H)—, n is 2, and each R$_1$ and each R$_2$ are hydrogen. In some embodiments is a compound of Formula (II), or a pharmaceutically acceptable salt or solvate thereof, wherein X is —N(H)— and n is 3. In some embodiments is a compound of Formula (II), or a pharmaceutically acceptable salt or solvate thereof, wherein X is —N(H)—, n is 3, and each R$_1$ and each R$_2$ are hydrogen.

In some embodiments is a compound of Formula (II), or a pharmaceutically acceptable salt or solvate thereof, wherein X is —C(R$_9$)(R$_{10}$)—O—. In some embodiments is a compound of Formula (II), or a pharmaceutically acceptable salt or solvate thereof, wherein X is —CH$_2$O— and n is 1. In some embodiments is a compound of Formula (II), or a pharmaceutically acceptable salt or solvate thereof, wherein X is —CH$_2$O—, n is 1, and R$_1$ and R$_2$ are hydrogen. In some embodiments is a compound of Formula (II), or a pharmaceutically acceptable salt or solvate thereof, wherein X is —CH$_2$O— and n is 2. In some embodiments is a compound of Formula (II), or a pharmaceutically acceptable salt or solvate thereof, wherein X is —CH$_2$O—, n is 2, and each R$_1$ and each R$_2$ are hydrogen. In some embodiments is a compound of Formula (II), or a pharmaceutically acceptable salt or solvate thereof, wherein X is —CH$_2$O— and n is 3. In some embodiments is a compound of Formula (II), or a pharmaceutically acceptable salt or solvate thereof, wherein X is —CH$_2$O—, n is 3, and each R$_1$ and each R$_2$ are hydrogen.

In some embodiments is a compound of Formula (II), or a pharmaceutically acceptable salt or solvate thereof, wherein R$_4$ is selected from hydrogen and C$_1$-C$_6$alkyl. In some embodiments is a compound of Formula (II), or a pharmaceutically acceptable salt or solvate thereof, wherein $R_4$ is hydrogen. In some embodiments is a compound of Formula (II), or a pharmaceutically acceptable salt or solvate thereof, wherein $R_4$ is $C_1$-$C_6$alkyl.

In some embodiments is a compound of Formula (II), or a pharmaceutically acceptable salt or solvate thereof, wherein $R_5$ is selected from hydrogen and $C_1$-$C_6$alkyl. In some embodiments is a compound of Formula (II), or a pharmaceutically acceptable salt or solvate thereof, wherein $R_5$ is hydrogen. In some embodiments is a compound of Formula (II), or a pharmaceutically acceptable salt or solvate thereof, wherein $R_5$ is $C_1$-$C_6$alkyl.

In some embodiments is a compound of Formula (II), or a pharmaceutically acceptable salt or solvate thereof, wherein $R_{13}$ is hydrogen. In some embodiments is a compound of Formula (II), or a pharmaceutically acceptable salt or solvate thereof, wherein $R_5$ and $R_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy. In some embodiments is a compound of Formula (II), or a pharmaceutically acceptable salt or solvate thereof, wherein $R_5$ and $R_{13}$ together with the atoms to which they are attached are combined to form a 5- or 6-membered heterocycloalkyl ring, wherein the 5- or 6-membered heterocycloalkyl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy. In some embodiments is a compound of Formula (II), or a pharmaceutically acceptable salt or solvate thereof, wherein $R_5$ and $R_{13}$ together with the atoms to which they are attached are combined to form a 5- or 6-membered heteroaryl ring, wherein the 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy.

In some embodiments is a compound of Formula (II), or a pharmaceutically acceptable salt or solvate thereof, wherein $R_4$ is hydrogen and $R_5$ is $C_1$-$C_6$alkyl. In some embodiments is a compound of Formula (II), or a pharmaceutically acceptable salt or solvate thereof, wherein $R_4$ and $R_5$ are hydrogen. In some embodiments is a compound of Formula (II), or a pharmaceutically acceptable salt or solvate thereof, wherein $R_4$ and $R_5$ are $C_1$-$C_6$alkyl.

In some embodiments is a compound of Formula (II), or a pharmaceutically acceptable salt or solvate thereof, wherein each $R_3$ is hydrogen. In some embodiments is a compound of Formula (II), or a pharmaceutically acceptable salt or solvate thereof, wherein each $R_3$ is $C_1$-$C_6$alkyl. In some embodiments is a compound of Formula (II), or a pharmaceutically acceptable salt or solvate thereof, wherein $R_2$ and $R_3$ together with the atoms to which they are attached are combined to form a 5- or 6-membered heterocycloalkyl ring optionally substituted 1, 2, or 3 with groups selected from halogen, —OH, $C_1$-$C_6$alkyl, and —$C_1$-$C_6$alkyl-OH.

In some embodiments is a compound of Formula (II), or a pharmaceutically acceptable salt or solvate thereof, wherein $R_{18}$ is hydrogen. In some embodiments is a compound of Formula (II), or a pharmaceutically acceptable salt or solvate thereof, wherein $R_{18}$ is deuterium. In some embodiments is a compound of Formula (II), or a pharmaceutically acceptable salt or solvate thereof, wherein $R_{18}$ is halogen. In some embodiments is a compound of Formula (II), or a pharmaceutically acceptable salt or solvate thereof, wherein $R_{18}$ is $C_1$-$C_6$alkyl. In some embodiments is a compound of Formula (II), or a pharmaceutically acceptable salt or solvate thereof, wherein $R_{18}$ is $C_1$-$C_6$deuteroalkyl.

In some embodiments, provided herein is a compound of Formula (III), or a pharmaceutically acceptable salt or solvate thereof:

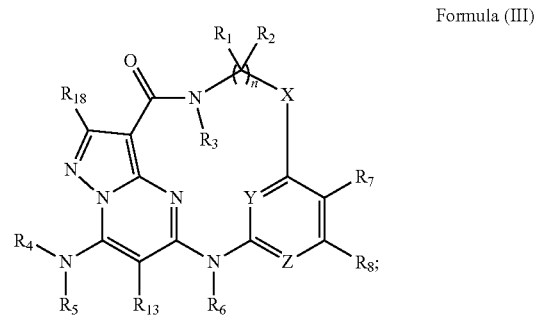

Formula (III)

wherein:
X is —O— or —C($R_9$)($R_{10}$)—;
Y is =N— or =C($R_{15}$)—;
Z is =N— or =C($R_{16}$)—;
each $R_1$ is independently selected from hydrogen, deuterium, $C_1$-$C_6$alkyl, and $C_1$-$C_6$deuteroalkyl;
each $R_2$ is independently selected from hydrogen, deuterium, $C_1$-$C_6$alkyl, and $C_1$-$C_6$deuteroalkyl;
$R_3$ is hydrogen or $C_1$-$C_6$alkyl;
$R_4$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;
$R_5$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;
$R_{13}$ is hydrogen, deuterium, $C_1$-$C_6$alkyl, or $C_1$-$C_6$deuteroalkyl; or $R_5$ and $R_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;
$R_6$ is hydrogen or $C_1$-$C_6$alkyl;
$R_7$ and $R_8$ are independently selected from hydrogen, deuterium, halogen, $C_1$-$C_6$alkyl, $C_1$-$C_6$deuteroalkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)N($R_{11})_2$, —$NR_{11}$C(=O)$R_{12}$, —$NR_{11}$S(=O)$_2$$R_{12}$, —S(=O)$_2$$R_{12}$, and —S(=O)$_2$N($R_{11})_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;
$R_9$ and $R_{10}$ are independently selected from hydrogen, deuterium, $C_1$-$C_6$alkyl, and $C_1$-$C_6$deuteroalkyl;
each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_{14}$, and —C(=O)N($R_{14})_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{15}$ and $R_{16}$ are independently selected from hydrogen, deuterium, halogen, $C_1$-$C_6$alkyl, $C_1$-$C_6$deuteroalkyl, $C_1$-$C_6$haloalkyl, $C_1$-$C_6$alkoxy, $C_1$-$C_6$heteroalkyl, —$OR_{11}$, —$N(R_{11})_2$, —CN, —C(=O)$R_{12}$, —C(=O)$OR_{11}$, —C(=O)$N(R_{11})_2$, —$NR_{11}$C(=O)$R_{12}$, —$NR_{11}$S(=O)$_2R_{12}$, —S(=O)$_2R_{12}$, and —S(=O)$_2N(R_{11})_2$;

$R_{18}$ is hydrogen, deuterium, halogen, $C_1$-$C_6$alkyl, or $C_1$-$C_6$deuteroalkyl; and n is 1, 2, 3, or 4.

In some embodiments is a compound of Formula (III), or a pharmaceutically acceptable salt or solvate thereof, wherein Y is =C($R_{15}$)— and Z is =C($R_{16}$)—. In some embodiments is a compound of Formula (III), or a pharmaceutically acceptable salt or solvate thereof, wherein Y is =C($R_{15}$)—, Z is =C($R_{16}$), $R_{15}$ is hydrogen, and $R_{16}$ is hydrogen. In some embodiments is a compound of Formula (III), or a pharmaceutically acceptable salt or solvate thereof, wherein Y is =C($R_{15}$)—, Z is =C($R_{16}$), $R_{15}$ is hydrogen, and $R_{16}$ is halogen. In some embodiments is a compound of Formula (III), or a pharmaceutically acceptable salt or solvate thereof, wherein Y is =C($R_{15}$)—, Z is =C($R_{16}$), $R_{15}$ is halogen, and $R_{16}$ is halogen. In some embodiments is a compound of Formula (III), or a pharmaceutically acceptable salt or solvate thereof, wherein Y is =C($R_{15}$)—, Z is =C($R_{16}$), $R_{15}$ is hydrogen, and $R_{16}$ is $C_1$-$C_6$alkyl. In some embodiments is a compound of Formula (III), or a pharmaceutically acceptable salt or solvate thereof, wherein Y is =C($R_{15}$)—, Z is =C($R_{16}$), $R_{15}$ is hydrogen, and $R_{16}$ is $C_1$-$C_6$haloalkyl.

In some embodiments is a compound of Formula (III), or a pharmaceutically acceptable salt or solvate thereof, wherein Y is =N— and Z is =C($R_{16}$)—. In some embodiments is a compound of Formula (III), or a pharmaceutically acceptable salt or solvate thereof, wherein Y is =N—, Z is =C($R_{16}$), and $R_{16}$ is hydrogen. In some embodiments is a compound of Formula (III), or a pharmaceutically acceptable salt or solvate thereof, wherein Y is =N—, Z is =C($R_{16}$), and $R_{16}$ is halogen. In some embodiments is a compound of Formula (III), or a pharmaceutically acceptable salt or solvate thereof, wherein Y is =N—, Z is =C($R_{16}$), and $R_{16}$ is $C_1$-$C_6$alkyl. In some embodiments is a compound of Formula (III), or a pharmaceutically acceptable salt or solvate thereof, wherein Y is =N—, Z is =C($R_{16}$), and $R_{16}$ is $C_1$-$C_6$haloalkyl.

In some embodiments is a compound of Formula (III), or a pharmaceutically acceptable salt or solvate thereof, wherein Y is =C($R_{15}$)— and Z is =N—. In some embodiments is a compound of Formula (III), or a pharmaceutically acceptable salt or solvate thereof, wherein Y is =C($R_{15}$)—, Z is =N—, and $R_{15}$ is hydrogen. In some embodiments is a compound of Formula (III), or a pharmaceutically acceptable salt or solvate thereof, wherein Y is =C($R_{15}$)—, Z is =N—, and $R_{15}$ is halogen. In some embodiments is a compound of Formula (III), or a pharmaceutically acceptable salt or solvate thereof, wherein Y is =C($R_{15}$)—, Z is =N—, and $R_{15}$ is $C_1$-$C_6$alkyl. In some embodiments is a compound of Formula (III), or a pharmaceutically acceptable salt or solvate thereof, wherein Y is =C($R_{15}$)—, Z is =N—, and $R_{15}$ is $C_1$-$C_6$haloalkyl.

In some embodiments is a compound of Formula (III), or a pharmaceutically acceptable salt or solvate thereof, wherein Y is =N— and Z is =N—.

In some embodiments is a compound of Formula (III), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (III), or a pharmaceutically acceptable salt or solvate thereof, wherein $R_7$ and $R_8$ are each hydrogen. In some embodiments is a compound of Formula (III), or a pharmaceutically acceptable salt or solvate thereof, wherein $R_7$ and $R_8$ are each halogen. In some embodiments is a compound of Formula (III), or a pharmaceutically acceptable salt or solvate thereof, wherein $R_7$ and $R_8$ are each $C_1$-$C_6$alkyl. In some embodiments is a compound of Formula (III), or a pharmaceutically acceptable salt or solvate thereof, wherein $R_7$ is hydrogen and $R_8$ is halogen. In some embodiments is a compound of Formula (III), or a pharmaceutically acceptable salt or solvate thereof, wherein $R_7$ is hydrogen and $R_8$ is $C_1$-$C_6$alkyl. In some embodiments is a compound of Formula (III), or a pharmaceutically acceptable salt or solvate thereof, wherein $R_7$ is hydrogen and $R_8$ is $C_1$-$C_6$haloalkyl. In some embodiments is a compound of Formula (III), or a pharmaceutically acceptable salt or solvate thereof, wherein $R_7$ is hydrogen and $R_8$ is $C_1$-$C_6$alkoxy. In some embodiments is a compound of Formula (III), or a pharmaceutically acceptable salt or solvate thereof, wherein $R_7$ is hydrogen and $R_8$ is —CN. In some embodiments is a compound of Formula (III), or a pharmaceutically acceptable salt or solvate thereof, wherein $R_7$ is halogen and $R_8$ is hydrogen. In some embodiments is a compound of Formula (III), or a pharmaceutically acceptable salt or solvate thereof, wherein $R_7$ is $C_1$-$C_6$alkyl and $R_8$ is hydrogen. In some embodiments is a compound of Formula (III), or a pharmaceutically acceptable salt or solvate thereof, wherein $R_7$ is $C_1$-$C_6$haloalkyl and $R_8$ is hydrogen. In some embodiments is a compound of Formula (III), or a pharmaceutically acceptable salt or solvate thereof, wherein $R_7$ is $C_1$-$C_6$alkoxy and $R_8$ is hydrogen. In some embodiments is a compound of Formula (III), or a pharmaceutically acceptable salt or solvate thereof, wherein $R_7$ is —CN and $R_8$ is hydrogen.

In some embodiments is a compound of Formula (III), or a pharmaceutically acceptable salt or solvate thereof, wherein X is —O—. In some embodiments is a compound of Formula (III), or a pharmaceutically acceptable salt or solvate thereof, wherein X is —O— and n is 2. In some embodiments is a compound of Formula (III), or a pharmaceutically acceptable salt or solvate thereof, wherein X is —O—, n is 2, and each $R_1$ and each $R_2$ are hydrogen. In some embodiments is a compound of Formula (III), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (III), or a pharmaceutically acceptable salt or solvate thereof, wherein X is —O— and n is 3. In some embodiments is a compound of Formula (III), or a pharmaceutically acceptable salt or solvate thereof, wherein X is —O—, n is 3, and each $R_1$ and each $R_2$ are hydrogen. In some embodiments is a compound of Formula (III), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (III), or a pharmaceutically acceptable salt or solvate thereof, wherein X is —C($R_9$)($R_{10}$)—. In some embodiments is a compound of Formula (III), or a pharmaceutically acceptable salt or solvate thereof, wherein X is —CH$_2$—. In some embodiments is a compound of Formula (III), or a pharmaceutically acceptable salt or solvate thereof, wherein X is —CH$_2$— and n is 1. In some embodiments is a compound of Formula (III), or a pharmaceutically acceptable salt or solvate thereof, wherein X is —CH$_2$—, n is 1, and R$_1$ and R$_2$ are hydrogen. In some embodiments is a compound of Formula (III), or a pharmaceutically acceptable salt or solvate thereof, wherein X is —CH$_2$— and n is 2. In some embodiments is a compound of Formula (III), or a pharmaceutically acceptable salt or solvate thereof, wherein X is —CH$_2$—, n is 2, and each R$_1$ and each R$_2$ are hydrogen. In some embodiments is a compound of Formula (III), or a pharmaceutically acceptable salt or solvate thereof, wherein X is —CH$_2$— and n is 3. In some embodiments is a compound of Formula (III), or a pharmaceutically acceptable salt or solvate thereof, wherein X is —CH$_2$—, n is 3, and each R$_1$ and each R$_2$ are hydrogen.

In some embodiments is a compound of Formula (III), or a pharmaceutically acceptable salt or solvate thereof, wherein R$_4$ is selected from hydrogen and C$_1$-C$_6$alkyl. In some embodiments is a compound of Formula (III), or a pharmaceutically acceptable salt or solvate thereof, wherein R$_4$ is hydrogen. In some embodiments is a compound of Formula (III), or a pharmaceutically acceptable salt or solvate thereof, wherein R$_4$ is C$_1$-C$_6$alkyl.

In some embodiments is a compound of Formula (III), or a pharmaceutically acceptable salt or solvate thereof, wherein R$_5$ is selected from hydrogen and C$_1$-C$_6$alkyl. In some embodiments is a compound of Formula (III), or a pharmaceutically acceptable salt or solvate thereof, wherein R$_5$ is hydrogen. In some embodiments is a compound of Formula (III), or a pharmaceutically acceptable salt or solvate thereof, wherein R$_5$ is C$_1$-C$_6$alkyl.

In some embodiments is a compound of Formula (III), or a pharmaceutically acceptable salt or solvate thereof, wherein R$_{13}$ is hydrogen. In some embodiments is a compound of Formula (III), or a pharmaceutically acceptable salt or solvate thereof, wherein R$_5$ and R$_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, C$_1$-C$_6$alkyl, C$_1$-C$_6$haloalkyl, C$_1$-C$_6$alkoxy, and C$_1$-C$_6$haloalkoxy. In some embodiments is a compound of Formula (III), or a pharmaceutically acceptable salt or solvate thereof, wherein R$_5$ and R$_{13}$ together with the atoms to which they are attached are combined to form a 5- or 6-membered heterocycloalkyl ring, wherein the 5- or 6-membered heterocycloalkyl ring is optionally substituted with 1, 2, or 3 groups selected from halogen, C$_1$-C$_6$alkyl, C$_1$-C$_6$haloalkyl, C$_1$-C$_6$alkoxy, and C$_1$-C$_6$haloalkoxy. In some embodiments is a compound of Formula (III), or a pharmaceutically acceptable salt or solvate thereof, wherein R$_5$ and R$_{13}$ together with the atoms to which they are attached are combined to form a 5- or 6-membered heteroaryl ring, wherein the 5- or 6-membered heteroaryl ring is optionally substituted with 1, 2, or 3 groups selected from halogen, C$_1$-C$_6$alkyl, C$_1$-C$_6$haloalkyl, C$_1$-C$_6$alkoxy, and C$_1$-C$_6$haloalkoxy.

In some embodiments is a compound of Formula (III), or a pharmaceutically acceptable salt or solvate thereof, wherein R$_4$ is hydrogen and R$_5$ is C$_1$-C$_6$alkyl. In some embodiments is a compound of Formula (III), or a pharmaceutically acceptable salt or solvate thereof, wherein R$_4$ and R$_5$ are hydrogen. In some embodiments is a compound of Formula (III), or a pharmaceutically acceptable salt or solvate thereof, wherein R$_4$ and R$_5$ are C$_1$-C$_6$alkyl.

In some embodiments is a compound of Formula (III), or a pharmaceutically acceptable salt or solvate thereof, wherein R$_3$ is hydrogen. In some embodiments is a compound of Formula (III), or a pharmaceutically acceptable salt or solvate thereof, wherein R$_3$ is C$_1$-C$_6$alkyl.

In some embodiments is a compound of Formula (III), or a pharmaceutically acceptable salt or solvate thereof, wherein R$_6$ is hydrogen. In some embodiments is a compound of Formula (III), or a pharmaceutically acceptable salt or solvate thereof, wherein R$_6$ is C$_1$-C$_6$alkyl.

In some embodiments is a compound of Formula (III), or a pharmaceutically acceptable salt or solvate thereof, wherein R$_{18}$ is hydrogen. In some embodiments is a compound of Formula (III), or a pharmaceutically acceptable salt or solvate thereof, wherein R$_{18}$ is deuterium. In some embodiments is a compound of Formula (III), or a pharmaceutically acceptable salt or solvate thereof, wherein R$_{18}$ is halogen. In some embodiments is a compound of Formula (III), or a pharmaceutically acceptable salt or solvate thereof, wherein R$_{18}$ is C$_1$-C$_6$alkyl. In some embodiments is a compound of Formula (III), or a pharmaceutically acceptable salt or solvate thereof, wherein R$_{18}$ is C$_1$-C$_6$deuteroalkyl.

In some embodiments, provided herein is a compound of Formula (IIIa), or a pharmaceutically acceptable salt or solvate thereof:

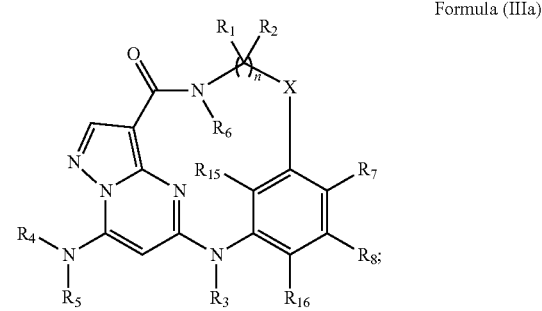

Formula (IIIa)

wherein:
X is —O— or —C(R$_9$)(R$_{10}$)—;
each R$_1$ is independently selected from hydrogen and C$_1$-C$_6$alkyl;
each R$_2$ is independently selected from hydrogen and C$_1$-C$_6$alkyl;
R$_3$ is hydrogen or C$_1$-C$_6$alkyl;
R$_4$ and R$_5$ are independently selected from hydrogen, C$_1$-C$_6$alkyl, C$_1$-C$_6$heteroalkyl, C$_3$-C$_6$cycloalkyl, and C$_2$-C$_9$heterocycloalkyl;
R$_6$ is hydrogen or C$_1$-C$_6$alkyl;
R$_7$ and R$_8$ are independently selected from hydrogen, halogen, C$_1$-C$_6$alkyl, —C$_1$-C$_6$alkyl-OH, C$_1$-C$_6$haloalkyl, C$_1$-C$_6$alkoxy, C$_3$-C$_6$cycloalkyl, C$_2$-C$_9$heterocycloalkyl, C$_2$-C$_9$heteroaryl, C$_6$-C$_{10}$aryl, —OR$_{11}$, —N(R$_{11}$)$_2$, —CN, —C(=O)R$_{12}$, —C(=O)OR$_{11}$, —C(=O)N(R$_{11}$)$_2$, —NR$_{11}$C(=O)R$_{12}$, —NR$_{11}$S(=O)$_2$R$_{12}$, —S(=O)$_2$R$_{12}$, and —S(=O)$_2$N(R$_{11}$)$_2$, wherein C$_3$-C$_6$cycloalkyl, C$_2$-C$_9$heterocycloalkyl, C$_2$-C$_9$heteroaryl, or C$_6$-C$_{10}$aryl are optionally substituted with 1, 2, or 3 groups selected from halogen, C$_1$-C$_6$alkyl, C$_1$-C$_6$haloalkyl, C$_1$-C$_6$alkoxy, and C$_1$-C$_6$haloalkoxy;
R$_9$ and R$_{10}$ are independently selected from hydrogen and C$_1$-C$_6$alkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —$C(=O)OR_{14}$, and —$C(=O)N(R_{14})_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{15}$ and $R_{16}$ are independently selected from hydrogen, halogen, $C_1$-$C_6$alkyl, $C_1$-$C_6$haloalkyl, $C_1$-$C_6$alkoxy, $C_1$-$C_6$heteroalkyl, —$OR_{11}$, —$N(R_{11})_2$, —$CN$, —$C(=O)R_{12}$, —$C(=O)OR_{11}$, —$C(=O)N(R_{11})_2$, —$NR_{11}C(=O)R_{12}$, —$NR_{11}S(=O)_2R_{12}$, —$S(=O)_2R_{12}$, and —$S(=O)_2N(R_{11})_2$; and n is 1, 2, 3, or 4.

In some embodiments is a compound of Formula (IIIa), or a pharmaceutically acceptable salt or solvate thereof, wherein $R_{15}$ is hydrogen and $R_{16}$ is hydrogen. In some embodiments is a compound of Formula (IIIa), or a pharmaceutically acceptable salt or solvate thereof, wherein $R_{15}$ is hydrogen and $R_{16}$ is halogen. In some embodiments is a compound of Formula (IIIa), or a pharmaceutically acceptable salt or solvate thereof, wherein $R_{15}$ is halogen and $R_{16}$ is halogen. In some embodiments is a compound of Formula (IIIa), or a pharmaceutically acceptable salt or solvate thereof, wherein $R_{15}$ is hydrogen and $R_{16}$ is $C_1$-$C_6$alkyl. In some embodiments is a compound of Formula (IIIa), or a pharmaceutically acceptable salt or solvate thereof, wherein $R_{15}$ is hydrogen and $R_{16}$ is $C_1$-$C_6$haloalkyl. In some embodiments is a compound of Formula (IIIa), or a pharmaceutically acceptable salt or solvate thereof, wherein $R_{15}$ is halogen and $R_{16}$ is hydrogen.

In some embodiments is a compound of Formula (IIIa), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IIIa), or a pharmaceutically acceptable salt or solvate thereof, wherein $R_7$ and $R_8$ are each hydrogen. In some embodiments is a compound of Formula (IIIa), or a pharmaceutically acceptable salt or solvate thereof, wherein $R_7$ and $R_8$ are each halogen. In some embodiments is a compound of Formula (IIIa), or a pharmaceutically acceptable salt or solvate thereof, wherein $R_7$ and $R_8$ are each $C_1$-$C_6$alkyl. In some embodiments is a compound of Formula (IIIa), or a pharmaceutically acceptable salt or solvate thereof, wherein $R_7$ is hydrogen and $R_8$ is halogen. In some embodiments is a compound of Formula (IIIa), or a pharmaceutically acceptable salt or solvate thereof, wherein $R_7$ is hydrogen and $R_8$ is $C_1$-$C_6$alkyl. In some embodiments is a compound of Formula (IIIa), or a pharmaceutically acceptable salt or solvate thereof, wherein $R_7$ is hydrogen and $R_8$ is $C_1$-$C_6$haloalkyl. In some embodiments is a compound of Formula (IIIa), or a pharmaceutically acceptable salt or solvate thereof, wherein $R_7$ is hydrogen and $R_8$ is $C_1$-$C_6$alkoxy. In some embodiments is a compound of Formula (IIIa), or a pharmaceutically acceptable salt or solvate thereof, wherein $R_7$ is hydrogen and $R_8$ is —CN. In some embodiments is a compound of Formula (IIIa), or a pharmaceutically acceptable salt or solvate thereof, wherein $R_7$ is halogen and $R_8$ is hydrogen. In some embodiments is a compound of Formula (IIIa), or a pharmaceutically acceptable salt or solvate thereof, wherein $R_7$ is $C_1$-$C_6$alkyl and $R_8$ is hydrogen. In some embodiments is a compound of Formula (IIIa), or a pharmaceutically acceptable salt or solvate thereof, wherein $R_7$ is $C_1$-$C_6$haloalkyl and $R_8$ is hydrogen. In some embodiments is a compound of Formula (IIIa), or a pharmaceutically acceptable salt or solvate thereof, wherein $R_7$ is $C_1$-$C_6$alkoxy and $R_8$ is hydrogen. In some embodiments is a compound of Formula (IIIa), or a pharmaceutically acceptable salt or solvate thereof, wherein $R_7$ is —CN and $R_8$ is hydrogen.

In some embodiments is a compound of Formula (IIIa), or a pharmaceutically acceptable salt or solvate thereof, wherein X is —O—. In some embodiments is a compound of Formula (IIIa), or a pharmaceutically acceptable salt or solvate thereof, wherein X is —O— and n is 2. In some embodiments is a compound of Formula (IIIa), or a pharmaceutically acceptable salt or solvate thereof, wherein X is —O—, n is 2, and each $R_1$ and each $R_2$ are hydrogen. In some embodiments is a compound of Formula (IIIa), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IIIa), or a pharmaceutically acceptable salt or solvate thereof, wherein X is —O— and n is 3. In some embodiments is a compound of Formula (IIIa), or a pharmaceutically acceptable salt or solvate thereof, wherein X is —O—, n is 3, and each $R_1$ and each $R_2$ are hydrogen. In some embodiments is a compound of Formula (IIIa), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IIIa), or a pharmaceutically acceptable salt or solvate thereof, wherein X is —$C(R_9)(R_{10})$—. In some embodiments is a compound of Formula (IIIa), or a pharmaceutically acceptable salt or solvate thereof, wherein X is —$CH_2$—. In some embodiments is a compound of Formula (IIIa), or a pharmaceutically acceptable salt or solvate thereof, wherein X is —$CH_2$— and n is 1. In some embodiments is a compound of Formula (IIIa), or a pharmaceutically acceptable salt or solvate thereof, wherein X is —$CH_2$—, n is 1, and $R_1$ and $R_2$ are hydrogen. In some embodiments is a compound of Formula (IIIa), or a pharmaceutically acceptable salt or solvate thereof, wherein X is —$CH_2$— and n is 2. In some embodiments is a compound of Formula (IIIa), or a pharmaceutically acceptable salt or solvate thereof, wherein X is —$CH_2$—, n is 2, and each $R_1$ and each $R_2$ are hydrogen. In some embodiments is a compound of Formula (IIIa), or a pharmaceutically acceptable salt or solvate thereof, wherein X is —$CH_2$— and n is 3. In some embodiments is a compound of Formula (IIIa), or a pharmaceutically acceptable salt or solvate thereof, wherein X is —$CH_2$—, n is 3, and each $R_1$ and each $R_2$ are hydrogen.

In some embodiments is a compound of Formula (IIIa), or a pharmaceutically acceptable salt or solvate thereof, wherein $R_4$ and $R_5$ are independently selected from hydrogen and $C_1$-$C_6$alkyl. In some embodiments is a compound of Formula (IIIa), or a pharmaceutically acceptable salt or solvate thereof, wherein $R_4$ is hydrogen and $R_5$ is $C_1$-$C_6$alkyl. In some embodiments is a compound of Formula (IIIa), or a pharmaceutically acceptable salt or solvate thereof, wherein $R_4$ and $R_5$ are hydrogen. In some embodiments is a compound of Formula (IIIa), or a pharmaceutically acceptable salt or solvate thereof, wherein $R_4$ and $R_5$ are $C_1$-$C_6$alkyl.

In some embodiments is a compound of Formula (IIIa), or a pharmaceutically acceptable salt or solvate thereof, wherein $R_3$ is hydrogen. In some embodiments is a compound of Formula (IIIa), or a pharmaceutically acceptable salt or solvate thereof, wherein $R_3$ is $C_1$-$C_6$alkyl.

In some embodiments is a compound of Formula (IIIa), or a pharmaceutically acceptable salt or solvate thereof, wherein $R_6$ is hydrogen. In some embodiments is a compound of Formula (IIIa), or a pharmaceutically acceptable salt or solvate thereof, wherein $R_6$ is $C_1$-$C_6$alkyl.

In some embodiments, provided herein is a compound of Formula (IIIb), or a pharmaceutically acceptable salt or solvate thereof:

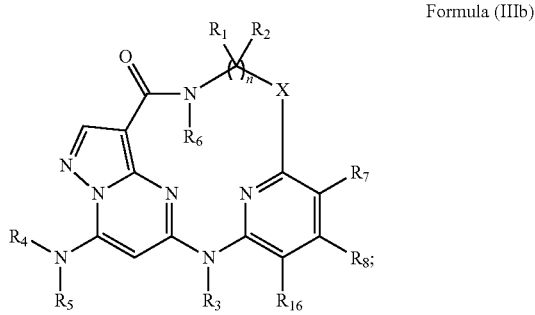

Formula (IIIb)

wherein:

X is —O— or —C($R_9$)($R_{10}$)—;

each $R_1$ is independently selected from hydrogen and $C_1$-$C_6$alkyl;

each $R_2$ is independently selected from hydrogen and $C_1$-$C_6$alkyl;

$R_3$ is hydrogen or $C_1$-$C_6$alkyl;

$R_4$ and $R_5$ are independently selected from hydrogen, $C_1$-$C_6$alkyl, $C_1$-$C_6$heteroalkyl, $C_3$-$C_6$cycloalkyl, and $C_2$-$C_9$heterocycloalkyl;

$R_6$ is hydrogen or $C_1$-$C_6$alkyl;

$R_7$ and $R_8$ are independently selected from hydrogen, halogen, $C_1$-$C_6$alkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)$N(R_{11})_2$, —$NR_{11}$C(=O)$R_{12}$, —$NR_{11}$S(=O)$_2R_{12}$, —S(=O)$_2R_{12}$, and —S(=O)$_2N(R_{11})_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_9$ and $R_{10}$ are independently selected from hydrogen and $C_1$-$C_6$alkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_{14}$, and —C(=O)$N(R_4)_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{16}$ is selected from hydrogen, halogen, $C_1$-$C_6$alkyl, $C_1$-$C_6$haloalkyl, $C_1$-$C_6$alkoxy, $C_1$-$C_6$heteroalkyl, —$OR_{11}$, —$N(R_{11})_2$, —CN, —C(=O)$R_{12}$, —C(=O)$OR_{11}$, —C(=O)$N(R_{11})_2$, —$NR_{11}$C(=O)$R_{12}$, —$NR_{11}$S(=O)$_2R_{12}$, —S(=O)$_2R_{12}$, and —S(=O)$_2N(R_{11})_2$; and n is 1, 2, 3, or 4.

In some embodiments is a compound of Formula (IIIb), or a pharmaceutically acceptable salt or solvate thereof, wherein $R_{16}$ is hydrogen. In some embodiments is a compound of Formula (IIIb), or a pharmaceutically acceptable salt or solvate thereof, wherein $R_{16}$ is halogen. In some embodiments is a compound of Formula (IIIb), or a pharmaceutically acceptable salt or solvate thereof, wherein $R_{16}$ is $C_1$-$C_6$alkyl. In some embodiments is a compound of Formula (IIIb), or a pharmaceutically acceptable salt or solvate thereof, wherein $R_{16}$ is $C_1$-$C_6$haloalkyl.

In some embodiments is a compound of Formula (IIIb), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IIIb), or a pharmaceutically acceptable salt or solvate thereof, wherein $R_7$ and $R_8$ are each hydrogen. In some embodiments is a compound of Formula (IIIb), or a pharmaceutically acceptable salt or solvate thereof, wherein $R_7$ and $R_8$ are each halogen. In some embodiments is a compound of Formula (IIIb), or a pharmaceutically acceptable salt or solvate thereof, wherein $R_7$ and $R_8$ are each $C_1$-$C_6$alkyl. In some embodiments is a compound of Formula (IIIb), or a pharmaceutically acceptable salt or solvate thereof, wherein $R_7$ is hydrogen and $R_8$ is halogen. In some embodiments is a compound of Formula (IIIb), or a pharmaceutically acceptable salt or solvate thereof, wherein $R_7$ is hydrogen and $R_8$ is $C_1$-$C_6$alkyl. In some embodiments is a compound of Formula (IIIb), or a pharmaceutically acceptable salt or solvate thereof, wherein $R_7$ is hydrogen and $R_8$ is $C_1$-$C_6$haloalkyl. In some embodiments is a compound of Formula (IIIb), or a pharmaceutically acceptable salt or solvate thereof, wherein $R_7$ is hydrogen and $R_8$ is $C_1$-$C_6$alkoxy. In some embodiments is a compound of Formula (IIIb), or a pharmaceutically acceptable salt or solvate thereof, wherein $R_7$ is hydrogen and $R_8$ is —CN. In some embodiments is a compound of Formula (IIIb), or a pharmaceutically acceptable salt or solvate thereof, wherein $R_7$ is halogen and $R_8$ is hydrogen. In some embodiments is a compound of Formula (IIIb), or a pharmaceutically acceptable salt or solvate thereof, wherein $R_7$ is $C_1$-$C_6$alkyl and $R_8$ is hydrogen. In some embodiments is a compound of Formula (IIIb), or a pharmaceutically acceptable salt or solvate thereof, wherein $R_7$ is $C_1$-$C_6$haloalkyl and $R_8$ is hydrogen. In some embodiments is a compound of Formula (IIIb), or a pharmaceutically acceptable salt or solvate thereof, wherein $R_7$ is $C_1$-$C_6$alkoxy and $R_8$ is hydrogen. In some embodiments is a compound of Formula (IIIb), or a pharmaceutically acceptable salt or solvate thereof, wherein $R_7$ is —CN and $R_8$ is hydrogen.

In some embodiments is a compound of Formula (IIIb), or a pharmaceutically acceptable salt or solvate thereof, wherein X is —O—. In some embodiments is a compound of Formula (IIIb), or a pharmaceutically acceptable salt or solvate thereof, wherein X is —O— and n is 2. In some embodiments is a compound of Formula (IIIb), or a pharmaceutically acceptable salt or solvate thereof, wherein X is —O—, n is 2, and each $R_1$ and each $R_2$ are hydrogen. In some embodiments is a compound of Formula (IIIb), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IIIb), or a pharmaceutically acceptable salt or solvate thereof, wherein X is —O— and n is 3. In some embodiments is a compound of Formula (IIIb), or a pharmaceutically acceptable salt or solvate thereof, wherein X is —O—, n is 3, and each $R_1$ and each $R_2$ are hydrogen. In some embodiments is a compound of Formula (IIIb), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IIIb), or a pharmaceutically acceptable salt or solvate thereof, wherein X is —C($R_9$)($R_{10}$)—. In some embodiments is a compound of Formula (IIIb), or a pharmaceutically acceptable salt or solvate thereof, wherein X is —CH$_2$—. In some embodiments is a compound of Formula (IIIb), or a pharmaceutically acceptable salt or solvate thereof, wherein X is —CH$_2$— and n is 1. In some embodiments is a compound of Formula (IIIb), or a pharmaceutically acceptable salt or solvate thereof, wherein X is —CH$_2$—, n is 1, and $R_1$ and $R_2$ are hydrogen. In some embodiments is a compound of Formula (IIIb), or a pharmaceutically acceptable salt or solvate thereof, wherein X is —CH$_2$— and n is 2. In some embodiments is a compound of Formula (IIIb), or a pharmaceutically acceptable salt or solvate thereof, wherein X is —CH$_2$—, n is 2, and each $R_1$ and each $R_2$ are hydrogen. In some embodiments is a compound of Formula (IIIb), or a pharmaceutically acceptable salt or solvate thereof, wherein X is —CH$_2$— and n is 3. In some embodiments is a compound of Formula (IIIb), or a pharmaceutically acceptable salt or solvate thereof, wherein X is —CH$_2$—, n is 3, and each $R_1$ and each $R_2$ are hydrogen.

In some embodiments is a compound of Formula (IIIb), or a pharmaceutically acceptable salt or solvate thereof, wherein $R_4$ and $R_5$ are independently selected from hydrogen and $C_1$-$C_6$alkyl. In some embodiments is a compound of Formula (IIIb), or a pharmaceutically acceptable salt or solvate thereof, wherein $R_4$ is hydrogen and $R_5$ is $C_1$-$C_6$alkyl. In some embodiments is a compound of Formula (IIIb), or a pharmaceutically acceptable salt or solvate thereof, wherein $R_4$ and $R_5$ are hydrogen. In some embodiments is a compound of Formula (IIIb), or a pharmaceutically acceptable salt or solvate thereof, wherein $R_4$ and $R_5$ are $C_1$-$C_6$alkyl.

In some embodiments is a compound of Formula (IIIb), or a pharmaceutically acceptable salt or solvate thereof, wherein $R_3$ is hydrogen. In some embodiments is a compound of Formula (IIIb), or a pharmaceutically acceptable salt or solvate thereof, wherein $R_3$ is $C_1$-$C_6$alkyl.

In some embodiments is a compound of Formula (IIIb), or a pharmaceutically acceptable salt or solvate thereof, wherein $R_6$ is hydrogen. In some embodiments is a compound of Formula (IIIb), or a pharmaceutically acceptable salt or solvate thereof, wherein $R_6$ is $C_1$-$C_6$alkyl.

In some embodiments, provided herein is a compound of Formula (IIIc), or a pharmaceutically acceptable salt or solvate thereof:

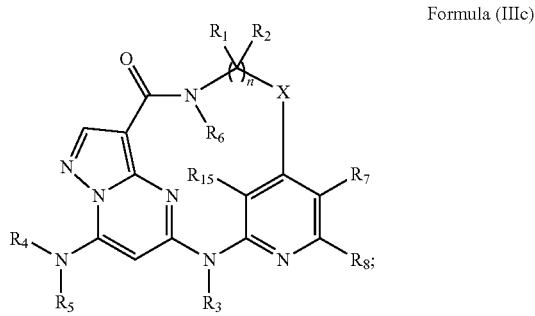

Formula (IIIc)

wherein:

X is —O— or —C($R_9$)($R_{10}$)—;

each $R_1$ is independently selected from hydrogen and $C_1$-$C_6$alkyl;

each $R_2$ is independently selected from hydrogen and $C_1$-$C_6$alkyl;

$R_3$ is hydrogen or $C_1$-$C_6$alkyl;

$R_4$ and $R_5$ are independently selected from hydrogen, $C_1$-$C_6$alkyl, $C_1$-$C_6$heteroalkyl, $C_3$-$C_6$cycloalkyl, and $C_2$-$C_9$heterocycloalkyl;

$R_6$ is hydrogen or $C_1$-$C_6$alkyl;

$R_7$ and $R_8$ are independently selected from hydrogen, halogen, $C_1$-$C_6$alkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)$N(R_{11})_2$, —$NR_{11}$C(=O)$R_{12}$, —$NR_{11}$S(=O)$_2R_{12}$, —S(=O)$_2R_{12}$, and —S(=O)$_2N(R_{11})_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_9$ and $R_{10}$ are independently selected from hydrogen and $C_1$-$C_6$alkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_{14}$, and —C(=O)$N(R_{14})_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{15}$ is selected from hydrogen, halogen, $C_1$-$C_6$alkyl, $C_1$-$C_6$haloalkyl, $C_1$-$C_6$alkoxy, $C_1$-$C_6$heteroalkyl, —$OR_{11}$, —$N(R_{11})_2$, —CN, —C(=O)$R_{12}$, —C(=O)$OR_{11}$, —C(=O)$N(R_{11})_2$, —$NR_{11}$C(=O)$R_{12}$, —$NR_{11}$S(=O)$_2R_{12}$, —S(=O)$_2R_{12}$, and —S(=O)$_2N(R_{11})_2$; and n is 1, 2, 3, or 4.

In some embodiments is a compound of Formula (IIIc), or a pharmaceutically acceptable salt or solvate thereof, wherein $R_{15}$ is hydrogen. In some embodiments is a compound of Formula (IIIc), or a pharmaceutically acceptable salt or solvate thereof, wherein $R_{15}$ is halogen. In some embodiments is a compound of Formula (IIIc), or a pharmaceutically acceptable salt or solvate thereof, wherein $R_{15}$ is $C_1$-$C_6$alkyl. In some embodiments is a compound of Formula (IIIc), or a pharmaceutically acceptable salt or solvate thereof, wherein $R_{15}$ is $C_1$-$C_6$haloalkyl.

In some embodiments is a compound of Formula (IIIc), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IIIc), or a pharmaceutically acceptable salt or solvate thereof, wherein $R_7$ and $R_8$ are each hydrogen. In some embodiments is a compound of Formula (IIIc), or a pharmaceutically acceptable salt or solvate thereof, wherein $R_7$ and $R_8$ are each halogen. In some embodiments is a compound of Formula (IIIc), or a pharmaceutically acceptable salt or solvate thereof, wherein $R_7$ and $R_8$ are each $C_1$-$C_6$alkyl. In some embodiments is a compound of Formula (IIIc), or a pharmaceutically acceptable salt or solvate thereof, wherein $R_7$ is hydrogen and $R_8$ is halogen. In some embodiments is a compound of Formula (IIIc), or a pharmaceutically acceptable salt or solvate thereof, wherein $R_7$ is hydrogen and $R_8$ is $C_1$-$C_6$alkyl. In some embodiments is a compound of Formula (IIIc), or a pharmaceutically acceptable salt or solvate thereof, wherein $R_7$ is hydrogen and $R_8$ is $C_1$-$C_6$haloalkyl. In some embodiments is a compound of Formula (IIIc), or a pharmaceutically acceptable salt or solvate thereof, wherein $R_7$ is hydrogen and $R_8$ is $C_1$-$C_6$alkoxy. In some embodiments is a compound of Formula (IIIc), or a pharmaceutically acceptable salt or solvate thereof, wherein $R_7$ is hydrogen and $R_8$ is —CN. In some embodiments is a compound of Formula (IIIc), or a pharmaceutically acceptable salt or solvate thereof, wherein $R_7$ is halogen and $R_8$ is hydrogen. In some embodiments is a compound of Formula (IIIc), or a pharmaceutically acceptable salt or solvate thereof, wherein $R_7$ is $C_1$-$C_6$alkyl and $R_8$ is hydrogen. In some embodiments is a compound of Formula (IIIc), or a pharmaceutically acceptable salt or solvate thereof, wherein $R_7$ is $C_1$-$C_6$haloalkyl and $R_8$ is hydrogen. In some embodiments is a compound of Formula (IIIc), or a pharmaceutically acceptable salt or solvate thereof, wherein $R_7$ is $C_1$-$C_6$alkoxy and $R_8$ is hydrogen. In some embodiments is a compound of Formula (IIIc), or a pharmaceutically acceptable salt or solvate thereof, wherein $R_7$ is —CN and $R_8$ is hydrogen.

In some embodiments is a compound of Formula (IIIc), or a pharmaceutically acceptable salt or solvate thereof, wherein X is —O—. In some embodiments is a compound of Formula (IIIc), or a pharmaceutically acceptable salt or solvate thereof, wherein X is —O— and n is 2. In some embodiments is a compound of Formula (IIIc), or a pharmaceutically acceptable salt or solvate thereof, wherein X is —O—, n is 2, and each $R_1$ and each $R_2$ are hydrogen. In some embodiments is a compound of Formula (IIIc), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IIIc), or a pharmaceutically acceptable salt or solvate thereof, wherein X is —O— and n is 3. In some embodiments is a compound of Formula (IIIc), or a pharmaceutically acceptable salt or solvate thereof, wherein X is —O—, n is 3, and each $R_1$ and each $R_2$ are hydrogen. In some embodiments is a compound of Formula (IIIc), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IIIc), or a pharmaceutically acceptable salt or solvate thereof, wherein X is —C($R_9$)($R_{10}$)—. In some embodiments is a compound of Formula (IIIc), or a pharmaceutically acceptable salt or solvate thereof, wherein X is —CH$_2$—. In some embodiments is a compound of Formula (IIIc), or a pharmaceutically acceptable salt or solvate thereof, wherein X is —CH$_2$— and n is 1. In some embodiments is a compound of Formula (IIIc), or a pharmaceutically acceptable salt or solvate thereof, wherein X is —CH$_2$—, n is 1, and $R_1$ and $R_2$ are hydrogen. In some embodiments is a compound of Formula (IIIc), or a pharmaceutically acceptable salt or solvate thereof, wherein X is —CH$_2$— and n is 2. In some embodiments is a compound of Formula (IIIc), or a pharmaceutically acceptable salt or solvate thereof, wherein X is —CH$_2$—, n is 2, and each $R_1$ and each $R_2$ are hydrogen. In some embodiments is a compound of Formula (IIIc), or a pharmaceutically acceptable salt or solvate thereof, wherein X is —CH$_2$— and n is 3. In some embodiments is a compound of Formula (IIIc), or a pharmaceutically acceptable salt or solvate thereof, wherein X is —CH$_2$—, n is 3, and each $R_1$ and each $R_2$ are hydrogen.

In some embodiments is a compound of Formula (IIIc), or a pharmaceutically acceptable salt or solvate thereof, wherein $R_4$ and $R_5$ are independently selected from hydrogen and $C_1$-$C_6$alkyl. In some embodiments is a compound of Formula (IIIc), or a pharmaceutically acceptable salt or solvate thereof, wherein $R_4$ is hydrogen and $R_5$ is $C_1$-$C_6$alkyl. In some embodiments is a compound of Formula (IIIc), or a pharmaceutically acceptable salt or solvate thereof, wherein $R_4$ and $R_5$ are hydrogen. In some embodiments is a compound of Formula (IIIc), or a pharmaceutically acceptable salt or solvate thereof, wherein $R_4$ and $R_5$ are $C_1$-$C_6$alkyl.

In some embodiments is a compound of Formula (IIIc), or a pharmaceutically acceptable salt or solvate thereof, wherein $R_3$ is hydrogen. In some embodiments is a compound of Formula (IIIc), or a pharmaceutically acceptable salt or solvate thereof, wherein $R_3$ is $C_1$-$C_6$alkyl.

In some embodiments is a compound of Formula (IIIc), or a pharmaceutically acceptable salt or solvate thereof, wherein $R_6$ is hydrogen. In some embodiments is a compound of Formula (IIIc), or a pharmaceutically acceptable salt or solvate thereof, wherein $R_6$ is $C_1$-$C_6$alkyl.

In some embodiments, provided herein is a compound of Formula (IIId), or a pharmaceutically acceptable salt or solvate thereof:

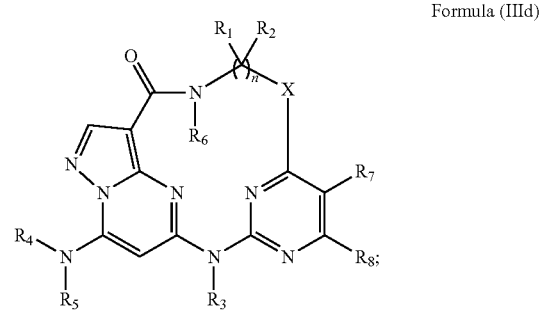

Formula (IIId)

wherein:

X is —O— or —C($R_9$)($R_{10}$)—;

each $R_1$ is independently selected from hydrogen and $C_1$-$C_6$alkyl;

each $R_2$ is independently selected from hydrogen and $C_1$-$C_6$alkyl;

$R_3$ is hydrogen or $C_1$-$C_6$alkyl;

$R_4$ and $R_5$ are independently selected from hydrogen, $C_1$-$C_6$alkyl, $C_1$-$C_6$heteroalkyl, $C_3$-$C_6$cycloalkyl, and $C_2$-$C_9$heterocycloalkyl;

$R_6$ is hydrogen or $C_1$-$C_6$alkyl;

$R_7$ and R are independently selected from hydrogen, halogen, $C_1$-$C_6$alkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O$R_{11}$, —C(=O)N($R_{11}$)$_2$, —$NR_{11}$C(=O)$R_{12}$, —$NR_{11}$S(=O)$_2$$R_{12}$, —S(=O)$_2$$R_{12}$, and —S(=O)$_2$N($R_{10}$), wherein $C_3$-$C_6$cycloalkyl, $C_2$-$C_9$heterocycloalkyl, $C_2$-$C_9$heteroaryl, or $C_4$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_6$ and $R_{10}$ are independently selected from hydrogen and $C_1$-$C_6$alkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —$C(=O)OR_{14}$, and —$C(=O)N(R_4)_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl; and n is 1, 2, 3, or 4.

In some embodiments is a compound of Formula (IIId), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IIId), or a pharmaceutically acceptable salt or solvate thereof, wherein $R_7$ and $R_8$ are each hydrogen. In some embodiments is a compound of Formula (IIId), or a pharmaceutically acceptable salt or solvate thereof, wherein $R_7$ and $R_8$ are each halogen. In some embodiments is a compound of Formula (IIId), or a pharmaceutically acceptable salt or solvate thereof, wherein $R_7$ and $R_8$ are each $C_1$-$C_6$alkyl. In some embodiments is a compound of Formula (IIId), or a pharmaceutically acceptable salt or solvate thereof, wherein $R_7$ is hydrogen and $R_8$ is halogen. In some embodiments is a compound of Formula (IIId), or a pharmaceutically acceptable salt or solvate thereof, wherein $R_7$ is hydrogen and $R_8$ is $C_1$-$C_6$alkyl. In some embodiments is a compound of Formula (IIId), or a pharmaceutically acceptable salt or solvate thereof, wherein $R_7$ is hydrogen and $R_8$ is $C_1$-$C_6$haloalkyl. In some embodiments is a compound of Formula (IIId), or a pharmaceutically acceptable salt or solvate thereof, wherein $R_7$ is hydrogen and $R_8$ is $C_1$-$C_6$alkoxy. In some embodiments is a compound of Formula (IIId), or a pharmaceutically acceptable salt or solvate thereof, wherein $R_7$ is hydrogen and $R_8$ is —CN. In some embodiments is a compound of Formula (IIId), or a pharmaceutically acceptable salt or solvate thereof, wherein $R_7$ is halogen and $R_8$ is hydrogen. In some embodiments is a compound of Formula (IIId), or a pharmaceutically acceptable salt or solvate thereof, wherein $R_7$ is $C_1$-$C_6$alkyl and $R_8$ is hydrogen. In some embodiments is a compound of Formula (IIId), or a pharmaceutically acceptable salt or solvate thereof, wherein $R_7$ is $C_1$-$C_6$haloalkyl and $R_8$ is hydrogen. In some embodiments is a compound of Formula (IIId), or a pharmaceutically acceptable salt or solvate thereof, wherein $R_7$ is $C_1$-$C_6$alkoxy and $R_8$ is hydrogen. In some embodiments is a compound of Formula (IIId), or a pharmaceutically acceptable salt or solvate thereof, wherein $R_7$ is —CN and $R_8$ is hydrogen.

In some embodiments is a compound of Formula (IIId), or a pharmaceutically acceptable salt or solvate thereof, wherein X is —O—. In some embodiments is a compound of Formula (IIId), or a pharmaceutically acceptable salt or solvate thereof, wherein X is —O— and n is 2. In some embodiments is a compound of Formula (IIId), or a pharmaceutically acceptable salt or solvate thereof, wherein X is —O—, n is 2, and each $R_1$ and each $R_2$ are hydrogen. In some embodiments is a compound of Formula (IIId), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IIId), or a pharmaceutically acceptable salt or solvate thereof, wherein X is —O— and n is 3. In some embodiments is a compound of Formula (IIId), or a pharmaceutically acceptable salt or solvate thereof, wherein X is —O—, n is 3, and each $R_1$ and each $R_2$ are hydrogen. In some embodiments is a compound of Formula (IIId), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IIId), or a pharmaceutically acceptable salt or solvate thereof, wherein X is —$C(R_9)(R_{10})$—. In some embodiments is a compound of Formula (IIId), or a pharmaceutically acceptable salt or solvate thereof, wherein X is —$CH_2$—. In some embodiments is a compound of Formula (IIId), or a pharmaceutically acceptable salt or solvate thereof, wherein X is —$CH_2$— and n is 1. In some embodiments is a compound of Formula (IIId), or a pharmaceutically acceptable salt or solvate thereof, wherein X is —$CH_2$—, n is 1, and $R_1$ and $R_2$ are hydrogen. In some embodiments is a compound of Formula (IIId), or a pharmaceutically acceptable salt or solvate thereof, wherein X is —$CH_2$— and n is 2. In some embodiments is a compound of Formula (IIId), or a pharmaceutically acceptable salt or solvate thereof, wherein X is —$CH_2$—, n is 2, and each $R_1$ and each $R_2$ are hydrogen. In some embodiments is a compound of Formula (IIId), or a pharmaceutically acceptable salt or solvate thereof, wherein X is —$CH_2$— and n is 3. In some embodiments is a compound of Formula (IIId), or a pharmaceutically acceptable salt or solvate thereof, wherein X is —$CH_2$—, n is 3, and each $R_1$ and each $R_2$ are hydrogen.

In some embodiments is a compound of Formula (IIId), or a pharmaceutically acceptable salt or solvate thereof, wherein $R_4$ and $R_5$ are independently selected from hydrogen and $C_1$-$C_6$alkyl. In some embodiments is a compound of Formula (IIId), or a pharmaceutically acceptable salt or solvate thereof, wherein $R_4$ is hydrogen and $R_5$ is $C_1$-$C_6$alkyl. In some embodiments is a compound of Formula (IIId), or a pharmaceutically acceptable salt or solvate thereof, wherein $R_4$ and $R_5$ are hydrogen. In some embodiments is a compound of Formula (IIId), or a pharmaceutically acceptable salt or solvate thereof, wherein $R_4$ and $R_5$ are $C_1$-$C_6$alkyl.

In some embodiments is a compound of Formula (IIId), or a pharmaceutically acceptable salt or solvate thereof, wherein $R_3$ is hydrogen. In some embodiments is a compound of Formula (IIId), or a pharmaceutically acceptable salt or solvate thereof, wherein $R_3$ is $C_1$-$C_6$alkyl.

In some embodiments is a compound of Formula (IIId), or a pharmaceutically acceptable salt or solvate thereof, wherein $R_6$ is hydrogen. In some embodiments is a compound of Formula (IIId), or a pharmaceutically acceptable salt or solvate thereof, wherein $R_6$ is $C_1$-$C_6$alkyl.

In some embodiments, provided herein is a compound of Formula (IV), or a pharmaceutically acceptable salt or solvate thereof:

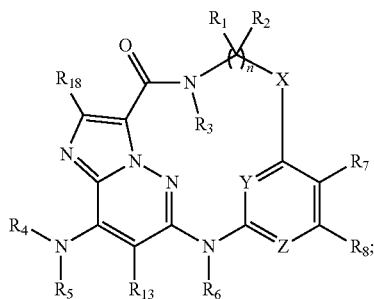

Formula (IV)

wherein:

X is —O— or —C($R_9$)($R_{10}$)—;

Y is =N— or =C($R_{15}$)—;

Z is =N— or =C($R_{16}$)—;

each $R_1$ is independently selected from hydrogen, deuterium, $C_1$-$C_6$alkyl, and $C_1$-$C_6$deuteroalkyl;

each $R_2$ is independently selected from hydrogen, deuterium, $C_1$-$C_6$alkyl, and $C_1$-$C_6$deuteroalkyl;

$R_3$ is hydrogen or $C_1$-$C_6$alkyl;

$R_4$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

$R_5$ is selected from hydrogen, deuterium, $C_1$-$C_6$alkyl, $C_1$-$C_6$deuteroalkyl, $C_1$-$C_6$heteroalkyl, $C_3$-$C_6$cycloalkyl, and $C_2$-$C_9$heterocycloalkyl;

$R_{13}$ is hydrogen, deuterium, $C_1$-$C_6$alkyl, or $C_1$-$C_6$deuteroalkyl; or $R_5$ and $R_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_6$ is hydrogen or $C_1$-$C_6$alkyl;

$R_7$ and $R_8$ are independently selected from hydrogen, deuterium, halogen, $C_1$-$C_6$alkyl, $C_1$-$C_6$deuteroalkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)N($R_{11}$)$_2$, —$NR_{11}$C(=O)$R_{12}$, —$NR_{11}$S(=O)$_2R_{12}$, —S(=O)$_2R_{12}$, and —S(=O)$_2$N($R_{11}$)$_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_9$ and $R_{10}$ are independently selected from hydrogen, deuterium, $C_1$-$C_6$alkyl, and $C_1$-$C_6$deuteroalkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_{14}$, and —C(=O)N($R_{14}$)$_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{15}$ and $R_{16}$ are independently selected from hydrogen, deuterium, halogen, $C_1$-$C_6$alkyl, $C_1$-$C_6$deuteroalkyl, $C_1$-$C_6$haloalkyl, $C_1$-$C_6$alkoxy, $C_1$-$C_6$heteroalkyl, —$OR_{11}$, —$N(R_{11})_2$, —CN, —C(=O)$R_{12}$, —C(=O)$OR_{11}$, —C(=O)N($R_{11}$)$_2$, —$NR_{11}$C(=O)$R_{12}$, —$NR_{11}$S(=O)$_2R_{12}$, —S(=O)$_2R_{12}$, and —S(=O)$_2$N($R_{11}$)$_2$;

$R_{18}$ is hydrogen, deuterium, halogen, $C_1$-$C_6$alkyl, or $C_1$-$C_6$deuteroalkyl; and n is 1, 2, 3, or 4.

In some embodiments is a compound of Formula (IV), or a pharmaceutically acceptable salt or solvate thereof, wherein Y is =C($R_{15}$)— and Z is =C($R_{16}$)—. In some embodiments is a compound of Formula (IV), or a pharmaceutically acceptable salt or solvate thereof, wherein Y is =C($R_{15}$)—, Z is =C($R_{16}$)—, $R_{15}$ is hydrogen, and $R_{16}$ is hydrogen. In some embodiments is a compound of Formula (IV), or a pharmaceutically acceptable salt or solvate thereof, wherein Y is =C($R_{15}$)—, Z is =C($R_{16}$), $R_{15}$ is hydrogen, and $R_{16}$ is halogen. In some embodiments is a compound of Formula (IV), or a pharmaceutically acceptable salt or solvate thereof, wherein Y is =C($R_{15}$)—, Z is =C($R_{16}$), $R_{15}$ is halogen, and $R_{16}$ is halogen. In some embodiments is a compound of Formula (IV), or a pharmaceutically acceptable salt or solvate thereof, wherein Y is =C($R_{15}$)—, Z is =C($R_{16}$), $R_{15}$ is hydrogen, and $R_{16}$ is $C_1$-$C_6$alkyl. In some embodiments is a compound of Formula (IV), or a pharmaceutically acceptable salt or solvate thereof, wherein Y is =C($R_{15}$)—, Z is =C($R_{16}$), $R_{15}$ is hydrogen, and $R_{16}$ is $C_1$-$C_6$haloalkyl.

In some embodiments is a compound of Formula (IV), or a pharmaceutically acceptable salt or solvate thereof, wherein Y is =N— and Z is =C($R_{16}$)—. In some embodiments is a compound of Formula (IV), or a pharmaceutically acceptable salt or solvate thereof, wherein Y is =N—, Z is =C($R_{16}$), and $R_{16}$ is hydrogen. In some embodiments is a compound of Formula (IV), or a pharmaceutically acceptable salt or solvate thereof, wherein Y is =N—, Z is =C($R_{16}$), and $R_{16}$ is halogen. In some embodiments is a compound of Formula (IV), or a pharmaceutically acceptable salt or solvate thereof, wherein Y is =N—, Z is =C($R_{16}$), and $R_{16}$ is $C_1$-$C_6$alkyl. In some embodiments is a compound of Formula (IV), or a pharmaceutically acceptable salt or solvate thereof, wherein Y is =N—, Z is =C($R_{16}$), and $R_{16}$ is $C_1$-$C_6$haloalkyl.

In some embodiments is a compound of Formula (IV), or a pharmaceutically acceptable salt or solvate thereof, wherein Y is =C($R_{15}$)— and Z is =N—. In some embodiments is a compound of Formula (IV), or a pharmaceutically acceptable salt or solvate thereof, wherein Y is =C($R_{15}$)—, Z is =N—, and $R_{15}$ is hydrogen. In some embodiments is a compound of Formula (IV), or a pharmaceutically acceptable salt or solvate thereof, wherein Y is =C($R_{15}$)—, Z is =N—, and $R_{15}$ is halogen. In some embodiments is a compound of Formula (IV), or a pharmaceutically acceptable salt or solvate thereof, wherein Y is =C($R_{15}$)—, Z is =N—, and $R_{15}$ is $C_1$-$C_6$alkyl. In some embodiments is a compound of Formula (IV), or a pharmaceutically acceptable salt or solvate thereof, wherein Y is =C($R_{15}$)—, Z is =N—, and $R_{15}$ is $C_1$-$C_6$haloalkyl.

In some embodiments is a compound of Formula (IV), or a pharmaceutically acceptable salt or solvate thereof, wherein Y is =N— and Z is =N—.

In some embodiments is a compound of Formula (IV), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IV), or a pharmaceutically acceptable salt or solvate thereof, wherein $R_7$ and $R_8$ are each hydrogen. In some embodiments is a compound of Formula (IV), or a pharmaceutically acceptable salt or solvate thereof, wherein $R_7$ and $R_8$ are each halogen. In some embodiments is a compound of Formula (IV), or a pharmaceutically acceptable salt or solvate thereof, wherein $R_7$ and $R_8$ are each $C_1$-$C_6$alkyl. In some embodiments is a compound of Formula (IV), or a pharmaceutically acceptable salt or solvate thereof, wherein $R_7$ is hydrogen and $R_8$ is halogen. In some embodiments is a compound of Formula (IV), or a pharmaceutically acceptable salt or solvate thereof, wherein $R_7$ is hydrogen and $R_8$ is $C_1$-$C_6$alkyl. In some embodiments is a compound of Formula (IV), or a pharmaceutically acceptable salt or solvate thereof, wherein $R_7$ is hydrogen and $R_8$ is $C_1$-$C_6$haloalkyl. In some embodiments is a compound of Formula (IV), or a pharmaceutically acceptable salt or solvate thereof, wherein $R_7$ is hydrogen and $R_8$ is $C_1$-$C_6$alkoxy. In some embodiments is a compound of Formula (IV), or a pharmaceutically acceptable salt or solvate thereof, wherein $R_7$ is hydrogen and $R_8$ is —CN. In some embodiments is a compound of Formula (IV), or a pharmaceutically acceptable salt or solvate thereof, wherein $R_7$ is halogen and $R_8$ is hydrogen. In some embodiments is a compound of Formula (IV), or a pharmaceutically acceptable salt or solvate thereof, wherein $R_7$ is $C_1$-$C_6$alkyl and $R_8$ is hydrogen. In some embodiments is a compound of Formula (IV), or a pharmaceutically acceptable salt or solvate thereof, wherein $R_7$ is $C_1$-$C_6$haloalkyl and $R_8$ is hydrogen. In some embodiments is a compound of Formula (IV), or a pharmaceutically acceptable salt or solvate thereof, wherein $R_7$ is $C_1$-$C_6$alkoxy and $R_8$ is hydrogen. In some embodiments is a compound of Formula (IV), or a pharmaceutically acceptable salt or solvate thereof, wherein $R_7$ is —CN and $R_8$ is hydrogen.

In some embodiments is a compound of Formula (IV), or a pharmaceutically acceptable salt or solvate thereof, wherein X is —O—. In some embodiments is a compound of Formula (IV), or a pharmaceutically acceptable salt or solvate thereof, wherein X is —O— and n is 2. In some embodiments is a compound of Formula (IV), or a pharmaceutically acceptable salt or solvate thereof, wherein X is —O—, n is 2, and each $R_1$ and each $R_2$ are hydrogen. In some embodiments is a compound of Formula (IV), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IV), or a pharmaceutically acceptable salt or solvate thereof, wherein X is —O— and n is 3. In some embodiments is a compound of Formula (IV), or a pharmaceutically acceptable salt or solvate thereof, wherein X is —O—, n is 3, and each $R_1$ and each $R_2$ are hydrogen. In some embodiments is a compound of Formula (IV), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IV), or a pharmaceutically acceptable salt or solvate thereof, wherein X is —C($R_9$)($R_{10}$)—. In some embodiments is a compound of Formula (IV), or a pharmaceutically acceptable salt or solvate thereof, wherein X is —CH$_2$—. In some embodiments is a compound of Formula (IV), or a pharmaceutically acceptable salt or solvate thereof, wherein X is —CH$_2$— and n is 1. In some embodiments is a compound of Formula (IV), or a pharmaceutically acceptable salt or solvate thereof, wherein X is —CH$_2$—, n is 1, and $R_1$ and $R_2$ are hydrogen. In some embodiments is a compound of Formula (IV), or a pharmaceutically acceptable salt or solvate thereof, wherein X is —CH$_2$— and n is 2. In some embodiments is a compound of Formula (IV), or a pharmaceutically acceptable salt or solvate thereof, wherein X is —CH$_2$—, n is 2, and each $R_1$ and each $R_2$ are hydrogen. In some embodiments is a compound of Formula (IV), or a pharmaceutically acceptable salt or solvate thereof, wherein X is —CH$_2$— and n is 3. In some embodiments is a compound of Formula (IV), or a pharmaceutically acceptable salt or solvate thereof, wherein X is —CH$_2$—, n is 3, and each $R_1$ and each $R_2$ are hydrogen.

In some embodiments is a compound of Formula (IV), or a pharmaceutically acceptable salt or solvate thereof, wherein $R_4$ is selected from hydrogen and $C_1$-$C_6$alkyl. In some embodiments is a compound of Formula (IV), or a pharmaceutically acceptable salt or solvate thereof, wherein $R_4$ is hydrogen. In some embodiments is a compound of Formula (IV), or a pharmaceutically acceptable salt or solvate thereof, wherein $R_4$ is $C_1$-$C_6$alkyl.

In some embodiments is a compound of Formula (IV), or a pharmaceutically acceptable salt or solvate thereof, wherein $R_5$ is selected from hydrogen and $C_1$-$C_6$alkyl. In some embodiments is a compound of Formula (IV), or a pharmaceutically acceptable salt or solvate thereof, wherein $R_5$ is hydrogen. In some embodiments is a compound of Formula (IV), or a pharmaceutically acceptable salt or solvate thereof, wherein $R_5$ is $C_1$-$C_6$alkyl.

In some embodiments is a compound of Formula (IV), or a pharmaceutically acceptable salt or solvate thereof, wherein $R_{13}$ is hydrogen. In some embodiments is a compound of Formula (IV), or a pharmaceutically acceptable salt or solvate thereof, wherein $R_5$ and $R_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy. In some embodiments is a compound of Formula (IV), or a pharmaceutically acceptable salt or solvate thereof, wherein $R_5$ and $R_{13}$ together with the atoms to which they are attached are combined to form a 5- or 6-membered heterocycloalkyl ring, wherein the 5- or 6-membered heterocycloalkyl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy. In some embodiments is a compound of Formula (IV), or a pharmaceutically acceptable salt or solvate thereof, wherein $R_5$ and $R_{13}$ together with the atoms to which they are attached are combined to form a 5- or 6-membered heteroaryl ring, wherein the 5- or 6-membered heteroaryl ring is optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy.

In some embodiments is a compound of Formula (IV), or a pharmaceutically acceptable salt or solvate thereof, wherein $R_4$ is hydrogen and $R_5$ is $C_1$-$C_6$alkyl. In some embodiments is a compound of Formula (IV), or a pharmaceutically acceptable salt or solvate thereof, wherein $R_4$ and $R_5$ are hydrogen. In some embodiments is a compound of Formula (IV), or a pharmaceutically acceptable salt or solvate thereof, wherein $R_4$ and $R_5$ are $C_1$-$C_6$alkyl.

In some embodiments is a compound of Formula (IV), or a pharmaceutically acceptable salt or solvate thereof, wherein $R_3$ is hydrogen. In some embodiments is a compound of Formula (IV), or a pharmaceutically acceptable salt or solvate thereof, wherein $R_3$ is $C_1$-$C_6$alkyl.

In some embodiments is a compound of Formula (IV), or a pharmaceutically acceptable salt or solvate thereof, wherein $R_6$ is hydrogen. In some embodiments is a compound of Formula (IV), or a pharmaceutically acceptable salt or solvate thereof, wherein $R_6$ is $C_1$-$C_6$alkyl.

In some embodiments is a compound of Formula (IV), or a pharmaceutically acceptable salt or solvate thereof, wherein $R_{18}$ is hydrogen. In some embodiments is a compound of Formula (IV), or a pharmaceutically acceptable salt or solvate thereof, wherein $R_{18}$ is deuterium. In some embodiments is a compound of Formula (IV), or a pharmaceutically acceptable salt or solvate thereof, wherein $R_{18}$ is halogen. In some embodiments is a compound of Formula (IV), or a pharmaceutically acceptable salt or solvate thereof, wherein $R_{18}$ is $C_1$-$C_6$alkyl. In some embodiments is a compound of Formula (IV), or a pharmaceutically acceptable salt or solvate thereof, wherein $R_{18}$ is $C_1$-$C_6$deuteroalkyl.

In some embodiments, provided herein is a compound of Formula (IVa), or a pharmaceutically acceptable salt or solvate thereof:

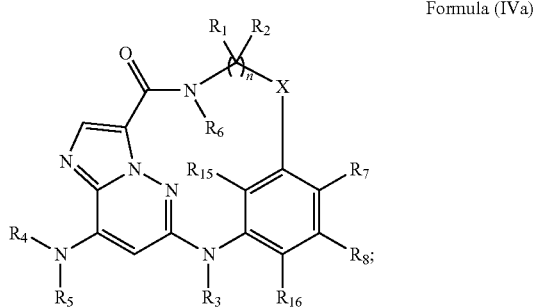

Formula (IVa)

wherein:

X is —O— or —C($R_9$)($R_{10}$)—;

each $R_1$ is independently selected from hydrogen and $C_1$-$C_6$alkyl;

each $R_2$ is independently selected from hydrogen and $C_1$-$C_6$alkyl;

$R_3$ is hydrogen or $C_1$-$C_6$alkyl;

$R_4$ and $R_5$ are independently selected from hydrogen, $C_1$-$C_6$alkyl, $C_1$-$C_6$heteroalkyl, $C_3$-$C_6$cycloalkyl, and $C_2$-$C_9$heterocycloalkyl;

$R_6$ is hydrogen or $C_1$-$C_6$alkyl;

$R_7$ and $R_8$ are independently selected from hydrogen, halogen, $C_1$-$C_6$alkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)N($R_{11})_2$, —$NR_{11}$C(=O)$R_{12}$, —$NR_{11}$S(=O)$_2R_{12}$, —S(=O)$_2R_{12}$, and —S(=O)$_2$N($R_{11})_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_9$ and $R_{10}$ are independently selected from hydrogen and $C_1$-$C_6$alkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_4$, and —C(=O)N($R_{14})_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{15}$ and $R_{16}$ are independently selected from hydrogen, halogen, $C_1$-$C_6$alkyl, $C_1$-$C_6$haloalkyl, $C_1$-$C_6$alkoxy, $C_1$-$C_6$heteroalkyl, —$OR_{11}$, —$N(R_{11})_2$, —CN, —C(=O)$R_{12}$, —C(=O)$OR_{11}$, —C(=O)N($R_{11})_2$, —$NR_{11}$C(=O)$R_{12}$, —$NR_{11}$S(=O)$_2R_{12}$, —S(=O)$_2R_{12}$, and —S(=O)$_2$N($R_{11})_2$; and n is 1, 2, 3, or 4.

In some embodiments is a compound of Formula (IVa), or a pharmaceutically acceptable salt or solvate thereof, wherein $R_{15}$ is hydrogen and $R_{16}$ is hydrogen. In some embodiments is a compound of Formula (IVa), or a pharmaceutically acceptable salt or solvate thereof, wherein $R_{15}$ is hydrogen and $R_{16}$ is halogen. In some embodiments is a compound of Formula (Iva), or a pharmaceutically acceptable salt or solvate thereof, wherein $R_{15}$ is halogen and $R_{16}$ is halogen. In some embodiments is a compound of Formula (IVa), or a pharmaceutically acceptable salt or solvate thereof, wherein $R_{15}$ is hydrogen and $R_{16}$ is $C_1$-$C_6$alkyl. In some embodiments is a compound of Formula (IVa), or a pharmaceutically acceptable salt or solvate thereof, wherein $R_{15}$ is hydrogen and $R_{16}$ is $C_1$-$C_6$haloalkyl. In some embodiments is a compound of Formula (IVa), or a pharmaceutically acceptable salt or solvate thereof, wherein $R_{15}$ is halogen and $R_{16}$ is hydrogen.

In some embodiments is a compound of Formula (IVa), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IVa), or a pharmaceutically acceptable salt or solvate thereof, wherein $R_7$ and $R_8$ are each hydrogen. In some embodiments is a compound of Formula (IVa), or a pharmaceutically acceptable salt or solvate thereof, wherein $R_7$ and $R_8$ are each halogen. In some embodiments is a compound of Formula (IVa), or a pharmaceutically acceptable salt or solvate thereof, wherein $R_7$ and $R_8$ are each $C_1$-$C_6$alkyl. In some embodiments is a compound of Formula (IVa), or a pharmaceutically acceptable salt or solvate thereof, wherein $R_7$ is hydrogen and $R_8$ is halogen. In some embodiments is a compound of Formula (IVa), or a pharmaceutically acceptable salt or solvate thereof, wherein $R_7$ is hydrogen and $R_8$ is $C_1$-$C_6$alkyl. In some embodiments is a compound of Formula (IVa), or a pharmaceutically acceptable salt or solvate thereof, wherein $R_7$ is hydrogen and $R_8$ is $C_1$-$C_6$haloalkyl. In some embodiments is a compound of Formula (IVa), or a pharmaceutically acceptable salt or solvate thereof, wherein $R_7$ is hydrogen and $R_8$ is $C_1$-$C_6$alkoxy. In some embodiments is a compound of Formula (IVa), or a pharmaceutically acceptable salt or solvate thereof, wherein $R_7$ is hydrogen and $R_8$ is —CN. In some embodiments is a compound of Formula (IVa), or a pharmaceutically acceptable salt or solvate thereof, wherein $R_7$ is halogen and $R_8$ is hydrogen. In some embodiments is a compound of Formula (IVa), or a pharmaceutically acceptable salt or solvate thereof, wherein $R_7$ is $C_1$-$C_6$alkyl and $R_8$ is hydrogen. In some embodiments is a compound of Formula (IVa), or a pharmaceutically acceptable salt or solvate thereof, wherein $R_7$ is $C_1$-$C_6$haloalkyl and $R_8$ is hydrogen. In some embodiments is a compound of Formula (Iva), or a pharmaceutically acceptable salt or solvate thereof, wherein $R_7$ is $C_1$-$C_6$alkoxy and $R_8$ is hydrogen. In some embodiments is a compound of Formula (IVa), or a pharmaceutically acceptable salt or solvate thereof, wherein $R_7$ is —CN and $R_8$ is hydrogen.

In some embodiments is a compound of Formula (IVa), or a pharmaceutically acceptable salt or solvate thereof, wherein X is —O—. In some embodiments is a compound of Formula (IVa), or a pharmaceutically acceptable salt or solvate thereof, wherein X is —O— and n is 2. In some embodiments is a compound of Formula (IVa), or a pharmaceutically acceptable salt or solvate thereof, wherein X is —O—, n is 2, and each $R_1$ and each $R_2$ are hydrogen. In some embodiments is a compound of Formula (IVa), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IVa), or a pharmaceutically acceptable salt or solvate thereof, wherein X is —O— and n is 3. In some embodiments is a compound of Formula (IVa), or a pharmaceutically acceptable salt or solvate thereof, wherein X is —O—, n is 3, and each $R_1$ and each $R_2$ are hydrogen. In some embodiments is a compound of Formula (IVa), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IVa), or a pharmaceutically acceptable salt or solvate thereof, wherein X is —C($R_9$)($R_{10}$)—. In some embodiments is a compound of Formula (IVa), or a pharmaceutically acceptable salt or solvate thereof, wherein X is —CH$_2$—. In some embodiments is a compound of Formula (IVa), or a pharmaceutically acceptable salt or solvate thereof, wherein X is —CH$_2$— and n is 1. In some embodiments is a compound of Formula (IVa), or a pharmaceutically acceptable salt or solvate thereof, wherein X is —CH$_2$—, n is 1, and $R_1$ and $R_2$ are hydrogen. In some embodiments is a compound of Formula (IVa), or a pharmaceutically acceptable salt or solvate thereof, wherein X is —CH$_2$— and n is 2. In some embodiments is a compound of Formula (IVa), or a pharmaceutically acceptable salt or solvate thereof, wherein X is —CH$_2$—, n is 2, and each $R_1$ and each $R_2$ are hydrogen. In some embodiments is a compound of Formula (IVa), or a pharmaceutically acceptable salt or solvate thereof, wherein X is —CH$_2$— and n is 3. In some embodiments is a compound of Formula (IVa), or a pharmaceutically acceptable salt or solvate thereof, wherein X is —CH$_2$—, n is 3, and each $R_1$ and each $R_2$ are hydrogen.

In some embodiments is a compound of Formula (IVa), or a pharmaceutically acceptable salt or solvate thereof, wherein $R_4$ and $R_5$ are independently selected from hydrogen and $C_1$-$C_6$alkyl. In some embodiments is a compound of Formula (IVa), or a pharmaceutically acceptable salt or solvate thereof, wherein $R_4$ is hydrogen and $R_5$ is $C_1$-$C_6$alkyl. In some embodiments is a compound of Formula (IVa), or a pharmaceutically acceptable salt or solvate thereof, wherein $R_4$ and $R_5$ are hydrogen. In some embodiments is a compound of Formula (IVa), or a pharmaceutically acceptable salt or solvate thereof, wherein $R_4$ and $R_5$ are $C_1$-$C_6$alkyl.

In some embodiments is a compound of Formula (IVa), or a pharmaceutically acceptable salt or solvate thereof, wherein $R_3$ is hydrogen. In some embodiments is a compound of Formula (IVa), or a pharmaceutically acceptable salt or solvate thereof, wherein $R_3$ is $C_1$-$C_6$alkyl.

In some embodiments is a compound of Formula (IVa), or a pharmaceutically acceptable salt or solvate thereof, wherein $R_6$ is hydrogen. In some embodiments is a compound of Formula (IVa), or a pharmaceutically acceptable salt or solvate thereof, wherein $R_6$ is $C_1$-$C_6$alkyl.

In some embodiments, provided herein is a compound of Formula (IVb), or a pharmaceutically acceptable salt or solvate thereof:

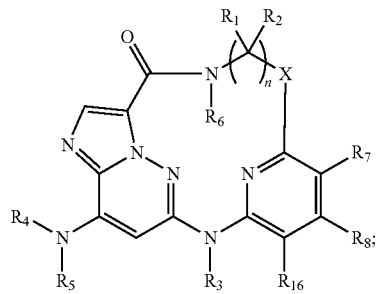

Formula (IVb)

wherein:

X is —O— or —C($R_9$)($R_{10}$)—;

each $R_1$ is independently selected from hydrogen and $C_1$-$C_6$alkyl;

each $R_2$ is independently selected from hydrogen and $C_1$-$C_6$alkyl;

$R_3$ is hydrogen or $C_1$-$C_6$alkyl;

$R_4$ and $R_5$ are independently selected from hydrogen, $C_1$-$C_6$alkyl, $C_1$-$C_6$heteroalkyl, $C_3$-$C_6$cycloalkyl, and $C_2$-$C_9$heterocycloalkyl;

$R_6$ is hydrogen or $C_1$-$C_6$alkyl;

$R_7$ and $R_8$ are independently selected from hydrogen, halogen, $C_1$-$C_6$alkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)N($R_{11}$)$_2$, —$NR_{11}$C(=O)$R_{12}$, —$NR_{11}$S(=O)$_2R_{12}$, —S(=O)$_2R_{12}$, and —S(=O)$_2$N($R_{11}$)$_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_9$ and $R_{10}$ are independently selected from hydrogen and $C_1$-$C_6$alkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_{14}$, and —C(=O)N($R_{14}$)$_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{16}$ is selected from hydrogen, halogen, $C_1$-$C_6$alkyl, $C_1$-$C_6$haloalkyl, $C_1$-$C_6$alkoxy, $C_1$-$C_6$heteroalkyl, —$OR_{11}$, —$N(R_{11})_2$, —CN, —C(=O)$R_{12}$, —C(=O)$OR_{11}$, —C(=O)N($R_{11}$)$_2$, —$NR_{11}$C(=O)$R_{12}$, —$NR_{11}$S(=O)$_2R_{12}$, —S(=O)$_2R_{12}$, and —S(=O)$_2$N($R_{11}$)$_2$; and n is 1, 2, 3, or 4.

In some embodiments is a compound of Formula (IVb), or a pharmaceutically acceptable salt or solvate thereof, wherein $R_{16}$ is hydrogen. In some embodiments is a compound of Formula (IVb), or a pharmaceutically acceptable salt or solvate thereof, wherein $R_{16}$ is halogen. In some embodiments is a compound of Formula (IVb), or a pharmaceutically acceptable salt or solvate thereof, wherein $R_{16}$ is $C_1$-$C_6$alkyl. In some embodiments is a compound of Formula (IVb), or a pharmaceutically acceptable salt or solvate thereof, wherein $R_{16}$ is $C_1$-$C_6$haloalkyl.

In some embodiments is a compound of Formula (IVb), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IVb), or a pharmaceutically acceptable salt or solvate thereof, wherein $R_7$ and $R_8$ are each hydrogen. In some embodiments is a compound of Formula (IVb), or a pharmaceutically acceptable salt or solvate thereof, wherein $R_7$ and $R_8$ are each halogen. In some embodiments is a compound of Formula (IVb), or a pharmaceutically acceptable salt or solvate thereof, wherein $R_7$ and $R_8$ are each $C_1$-$C_6$alkyl. In some embodiments is a compound of Formula (IVb), or a pharmaceutically acceptable salt or solvate thereof, wherein $R_7$ is hydrogen and $R_8$ is halogen. In some embodiments is a compound of Formula (IVb), or a pharmaceutically acceptable salt or solvate thereof, wherein $R_7$ is hydrogen and $R_8$ is $C_1$-$C_6$alkyl. In some embodiments is a compound of Formula (IVb), or a pharmaceutically acceptable salt or solvate thereof, wherein $R_7$ is hydrogen and $R_8$ is $C_1$-$C_6$haloalkyl. In some embodiments is a compound of Formula (IVb), or a pharmaceutically acceptable salt or solvate thereof, wherein $R_7$ is hydrogen and $R_8$ is $C_1$-$C_6$alkoxy. In some embodiments is a compound of Formula (IVb), or a pharmaceutically acceptable salt or solvate thereof, wherein $R_7$ is hydrogen and $R_8$ is —CN. In some embodiments is a compound of Formula (IVb), or a pharmaceutically acceptable salt or solvate thereof, wherein $R_7$ is halogen and $R_8$ is hydrogen. In some embodiments is a compound of Formula (IVb), or a pharmaceutically acceptable salt or solvate thereof, wherein $R_7$ is $C_1$-$C_6$alkyl and $R_8$ is hydrogen. In some embodiments is a compound of Formula (IVb), or a pharmaceutically acceptable salt or solvate thereof, wherein $R_7$ is $C_1$-$C_6$haloalkyl and $R_8$ is hydrogen. In some embodiments is a compound of Formula (IVb), or a pharmaceutically acceptable salt or solvate thereof, wherein $R_7$ is $C_1$-$C_6$alkoxy and $R_8$ is hydrogen. In some embodiments is a compound of Formula (IVb), or a pharmaceutically acceptable salt or solvate thereof, wherein $R_7$ is —CN and $R_8$ is hydrogen.

In some embodiments is a compound of Formula (IVb), or a pharmaceutically acceptable salt or solvate thereof, wherein X is —O—. In some embodiments is a compound of Formula (IVb), or a pharmaceutically acceptable salt or solvate thereof, wherein X is —O— and n is 2. In some embodiments is a compound of Formula (IVb), or a pharmaceutically acceptable salt or solvate thereof, wherein X is —O—, n is 2, and each $R_1$ and each $R_2$ are hydrogen. In some embodiments is a compound of Formula (IVb), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IVb), or a pharmaceutically acceptable salt or solvate thereof, wherein X is —O— and n is 3. In some embodiments is a compound of Formula (IVb), or a pharmaceutically acceptable salt or solvate thereof, wherein X is —O—, n is 3, and each $R_1$ and each $R_2$ are hydrogen. In some embodiments is a compound of Formula (IVb), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IVb), or a pharmaceutically acceptable salt or solvate thereof, wherein X is —C($R_9$)($R_{10}$)—. In some embodiments is a compound of Formula (IVb), or a pharmaceutically acceptable salt or solvate thereof, wherein X is —CH$_2$—. In some embodiments is a compound of Formula (IVb), or a pharmaceutically acceptable salt or solvate thereof, wherein X is —CH$_2$— and n is 1. In some embodiments is a compound of Formula (IVb), or a pharmaceutically acceptable salt or solvate thereof, wherein X is —CH$_2$—, n is 1, and $R_1$ and $R_2$ are hydrogen. In some embodiments is a compound of Formula (IVb), or a pharmaceutically acceptable salt or solvate thereof, wherein X is —CH$_2$— and n is 2. In some embodiments is a compound of Formula (IVb), or a pharmaceutically acceptable salt or solvate thereof, wherein X is —CH$_2$—, n is 2, and each $R_1$ and each $R_2$ are hydrogen. In some embodiments is a compound of Formula (IVb), or a pharmaceutically acceptable salt or solvate thereof, wherein X is —CH$_2$— and n is 3. In some embodiments is a compound of Formula (IVb), or a pharmaceutically acceptable salt or solvate thereof, wherein X is —CH$_2$—, n is 3, and each $R_1$ and each $R_2$ are hydrogen.

In some embodiments is a compound of Formula (IVb), or a pharmaceutically acceptable salt or solvate thereof, wherein $R_4$ and $R_5$ are independently selected from hydrogen and $C_1$-$C_6$alkyl. In some embodiments is a compound of Formula (IVb), or a pharmaceutically acceptable salt or solvate thereof, wherein $R_4$ is hydrogen and $R_5$ is $C_1$-$C_6$alkyl. In some embodiments is a compound of Formula (IVb), or a pharmaceutically acceptable salt or solvate thereof, wherein $R_4$ and $R_5$ are hydrogen. In some embodiments is a compound of Formula (IVb), or a pharmaceutically acceptable salt or solvate thereof, wherein $R_4$ and $R_5$ are $C_1$-$C_6$alkyl.

In some embodiments is a compound of Formula (IVb), or a pharmaceutically acceptable salt or solvate thereof, wherein $R_3$ is hydrogen. In some embodiments is a compound of Formula (IVb), or a pharmaceutically acceptable salt or solvate thereof, wherein $R_3$ is $C_1$-$C_6$alkyl.

In some embodiments is a compound of Formula (IVb), or a pharmaceutically acceptable salt or solvate thereof, wherein $R_6$ is hydrogen. In some embodiments is a compound of Formula (IVb), or a pharmaceutically acceptable salt or solvate thereof, wherein $R_6$ is $C_1$-$C_6$alkyl.

In some embodiments, provided herein is a compound of Formula (IVc), or a pharmaceutically acceptable salt or solvate thereof:

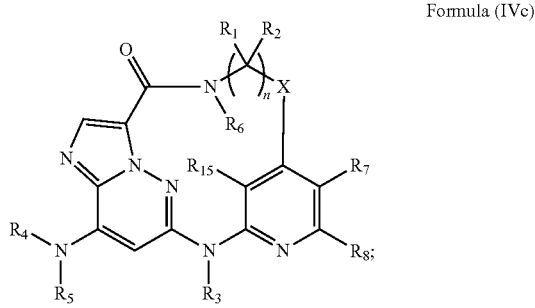

Formula (IVc)

wherein:
X is —O— or —C($R_9$)($R_{10}$)—;
each $R_1$ is independently selected from hydrogen and $C_1$-$C_6$alkyl;
each $R_2$ is independently selected from hydrogen and $C_1$-$C_6$alkyl;

$R_3$ is hydrogen or $C_1$-$C_6$alkyl;

$R_4$ and $R_5$ are independently selected from hydrogen, $C_1$-$C_6$alkyl, $C_1$-$C_6$heteroalkyl, $C_3$-$C_6$cycloalkyl, and $C_2$-$C_9$heterocycloalkyl;

$R_6$ is hydrogen or $C_1$-$C_6$alkyl;

$R_7$ and $R_8$ are independently selected from hydrogen, halogen, $C_1$-$C_6$alkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)N($R_{11})_2$, —$NR_{11}$C(=O)$R_{12}$, —$NR_{11}$S(=O)$_2R_{12}$, —S(=O)$_2R_{12}$, and —S(=O)$_2$N($R_{11})_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;

$R_9$ and $R_{10}$ are independently selected from hydrogen and $C_1$-$C_6$alkyl;

each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_4$, and —C(=O)N($R_{14})_2$;

each $R_{12}$ is independently selected from $C_1$-$C_6$alkyl and $C_1$-$C_6$heteroalkyl;

each $R_{14}$ is independently selected from hydrogen, $C_1$-$C_6$alkyl, and $C_1$-$C_6$haloalkyl;

$R_{15}$ is selected from hydrogen, halogen, $C_1$-$C_6$alkyl, $C_1$-$C_6$haloalkyl, $C_1$-$C_6$alkoxy, $C_1$-$C_6$heteroalkyl, —$OR_{11}$, —$N(R_{11})_2$, —CN, —C(=O)$R_{12}$, —C(=O)$OR_{11}$, —C(=O)N($R_{11})_2$, —$NR_{11}$C(=O)$R_{12}$, —$NR_{11}$S(=O)$_2R_{12}$, —S(=O)$_2R_{12}$, and —S(=O)$_2$N($R_{11})_2$; and n is 1, 2, 3, or 4.

In some embodiments is a compound of Formula (IVc), or a pharmaceutically acceptable salt or solvate thereof, wherein $R_{15}$ is hydrogen. In some embodiments is a compound of Formula (IVc), or a pharmaceutically acceptable salt or solvate thereof, wherein $R_{15}$ is halogen. In some embodiments is a compound of Formula (IVc), or a pharmaceutically acceptable salt or solvate thereof, wherein $R_{15}$ is $C_1$-$C_6$alkyl. In some embodiments is a compound of Formula (IVc), or a pharmaceutically acceptable salt or solvate thereof, wherein $R_{15}$ is $C_1$-$C_6$haloalkyl.

In some embodiments is a compound of Formula (IVc), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IVc), or a pharmaceutically acceptable salt or solvate thereof, wherein $R_7$ and $R_8$ are each hydrogen. In some embodiments is a compound of Formula (IVc), or a pharmaceutically acceptable salt or solvate thereof, wherein $R_7$ and $R_8$ are each halogen. In some embodiments is a compound of Formula (IVc), or a pharmaceutically acceptable salt or solvate thereof, wherein $R_7$ and $R_8$ are each $C_1$-$C_6$alkyl. In some embodiments is a compound of Formula (IVc), or a pharmaceutically acceptable salt or solvate thereof, wherein $R_7$ is hydrogen and $R_8$ is halogen. In some embodiments is a compound of Formula (IVc), or a pharmaceutically acceptable salt or solvate thereof, wherein $R_7$ is hydrogen and $R_8$ is $C_1$-$C_6$alkyl. In some embodiments is a compound of Formula (IVc), or a pharmaceutically acceptable salt or solvate thereof, wherein $R_7$ is hydrogen and $R_8$ is $C_1$-$C_6$haloalkyl. In some embodiments is a compound of Formula (IVc), or a pharmaceutically acceptable salt or solvate thereof, wherein $R_7$ is hydrogen and $R_8$ is $C_1$-$C_6$alkoxy. In some embodiments is a compound of Formula (IVc), or a pharmaceutically acceptable salt or solvate thereof, wherein $R_7$ is hydrogen and $R_8$ is —CN. In some embodiments is a compound of Formula (IVc), or a pharmaceutically acceptable salt or solvate thereof, wherein $R_7$ is halogen and $R_8$ is hydrogen. In some embodiments is a compound of Formula (IVc), or a pharmaceutically acceptable salt or solvate thereof, wherein $R_7$ is $C_1$-$C_6$alkyl and $R_8$ is hydrogen. In some embodiments is a compound of Formula (IVc), or a pharmaceutically acceptable salt or solvate thereof, wherein $R_7$ is $C_1$-$C_6$haloalkyl and $R_8$ is hydrogen. In some embodiments is a compound of Formula (IVc), or a pharmaceutically acceptable salt or solvate thereof, wherein $R_7$ is $C_1$-$C_6$alkoxy and $R_8$ is hydrogen. In some embodiments is a compound of Formula (IVc), or a pharmaceutically acceptable salt or solvate thereof, wherein $R_7$ is —CN and $R_8$ is hydrogen.

In some embodiments is a compound of Formula (IVc), or a pharmaceutically acceptable salt or solvate thereof, wherein X is —O—. In some embodiments is a compound of Formula (IVc), or a pharmaceutically acceptable salt or solvate thereof, wherein X is —O— and n is 2. In some embodiments is a compound of Formula (IVc), or a pharmaceutically acceptable salt or solvate thereof, wherein X is —O—, n is 2, and each $R_1$ and each $R_2$ are hydrogen. In some embodiments is a compound of Formula (IVc), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IVc), or a pharmaceutically acceptable salt or solvate thereof, wherein X is —O— and n is 3. In some embodiments is a compound of Formula (IVc), or a pharmaceutically acceptable salt or solvate thereof, wherein X is —O—, n is 3, and each $R_1$ and each $R_2$ are hydrogen. In some embodiments is a compound of Formula (IVc), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IVc), or a pharmaceutically acceptable salt or solvate thereof, wherein X is —C($R_9$)($R_{10}$)—. In some embodiments is a compound of Formula (IVc), or a pharmaceutically acceptable salt or solvate thereof, wherein X is —$CH_2$—. In some embodiments is a compound of Formula (IVc), or a pharmaceutically acceptable salt or solvate thereof, wherein X is —$CH_2$— and n is 1. In some embodiments is a compound of Formula (IVc), or a pharmaceutically acceptable salt or solvate thereof, wherein X is —$CH_2$—, n is 1, and $R_1$ and $R_2$ are hydrogen. In some embodiments is a compound of Formula (IVc), or a pharmaceutically acceptable salt or solvate thereof, wherein X is —$CH_2$— and n is 2. In some embodiments is a compound of Formula (IVc), or a pharmaceutically acceptable salt or solvate thereof, wherein X is —$CH_2$—, n is 2, and each $R_1$ and each $R_2$ are hydrogen. In some embodiments is a compound of Formula (IVc), or a pharmaceutically acceptable salt or solvate thereof, wherein X is —$CH_2$— and n is 3. In some embodiments is a compound of Formula (IVc), or a pharmaceutically acceptable salt or solvate thereof, wherein X is —$CH_2$—, n is 3, and each $R_1$ and each $R_2$ are hydrogen.

In some embodiments is a compound of Formula (IVc), or a pharmaceutically acceptable salt or solvate thereof, wherein $R_4$ and $R_5$ are independently selected from hydrogen and $C_1$-$C_6$alkyl. In some embodiments is a compound of Formula (IVc), or a pharmaceutically acceptable salt or solvate thereof, wherein $R_4$ is hydrogen and $R_5$ is $C_1$-$C_6$alkyl. In some embodiments is a compound of Formula (IVc), or a pharmaceutically acceptable salt or solvate thereof, wherein $R_4$ and $R_5$ are hydrogen. In some embodiments is a compound of Formula (IVc), or a pharmaceutically acceptable salt or solvate thereof, wherein $R_4$ and $R_5$ are $C_1$-$C_6$alkyl.

In some embodiments is a compound of Formula (IVc), or a pharmaceutically acceptable salt or solvate thereof, wherein $R_3$ is hydrogen. In some embodiments is a compound of Formula (IVc), or a pharmaceutically acceptable salt or solvate thereof, wherein $R_3$ is $C_1$-$C_6$alkyl.

In some embodiments is a compound of Formula (IVc), or a pharmaceutically acceptable salt or solvate thereof, wherein $R_6$ is hydrogen. In some embodiments is a compound of Formula (IVc), or a pharmaceutically acceptable salt or solvate thereof, wherein $R_6$ is $C_1$-$C_6$alkyl.

In some embodiments, provided herein is a compound of Formula (IVd), or a pharmaceutically acceptable salt or solvate thereof:

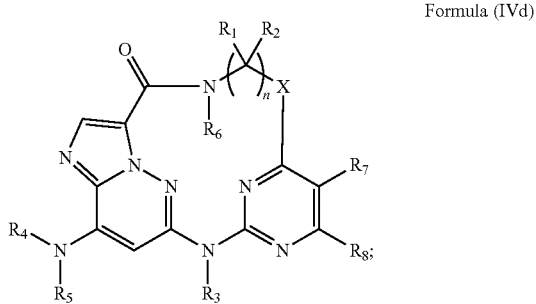

Formula (IVd)

wherein:
X is —O— or —C($R_9$)($R_{10}$)—;
each $R_1$ is independently selected from hydrogen and $C_1$-$C_6$alkyl;
each $R_2$ is independently selected from hydrogen and $C_1$-$C_6$alkyl;
$R_3$ is hydrogen or $C_1$-$C_6$alkyl;
$R_4$ and $R_5$ are independently selected from hydrogen, $C_1$-$C_6$alkyl, $C_1$-$C_6$heteroalkyl, $C_3$-$C_6$cycloalkyl, and $C_2$-$C_9$heterocycloalkyl;
$R_6$ is hydrogen or $C_1$-$C_6$alkyl;
$R_7$ and $R_8$ are independently selected from hydrogen, halogen, $C_1$-$C_6$alkyl, —$C_1$-$C_6$alkyl-OH, $C_1$-$C_6$haloalkyl, $C_1$-$C_6$alkoxy, $C_3$-$C_6$cycloalkyl, $C_2$-$C_9$heterocycloalkyl, $C_2$-$C_9$heteroaryl, $C_6$-$C_{10}$aryl, —$OR_{11}$, —$N(R_{11})_2$, —CN, —C(=O)$R_{12}$, —C(=O)$OR_{11}$, —C(=O)N($R_{11}$)$_2$, —$NR_{11}$C(=O)$R_{12}$, —$NR_{11}$S(=O)$_2$$R_{12}$, —S(=O)$_2$$R_{12}$, and —S(=O)$_2$N($R_{11}$)$_2$, wherein $C_3$-$C_6$cycloalkyl, $C_2$-$C_9$heterocycloalkyl, $C_2$-$C_9$heteroaryl, or $C_6$-$C_{10}$aryl are optionally substituted with 1, 2, or 3 groups selected from halogen, $C_1$-$C_6$alkyl, $C_1$-$C_6$haloalkyl, $C_1$-$C_6$alkoxy, and $C_1$-$C_6$haloalkoxy;
$R_9$ and $R_{10}$ are independently selected from hydrogen and $C_1$-$C_6$alkyl;
each $R_{11}$ is independently selected from hydrogen, $C_1$-$C_6$alkyl, $C_1$-$C_6$haloalkyl, $C_1$-$C_6$heteroalkyl, and phenyl, wherein phenyl is optionally substituted with 1, 2, or 3 groups selected from halogen, $C_1$-$C_6$alkyl, $C_1$-$C_6$haloalkyl, $C_1$-$C_6$alkoxy, $C_1$-$C_6$haloalkoxy, $C_2$-$C_9$heterocycloalkyl, $C_2$-$C_9$heteroaryl, —$OR_{14}$, —$N(R_{14})_2$, —C(=O)$OR_{14}$, and —C(=O)N($R_{14}$)$_2$;
each $R_{12}$ is independently selected from $C_1$-$C_6$alkyl and $C_1$-$C_6$heteroalkyl;
each $R_{14}$ is independently selected from hydrogen, $C_1$-$C_6$alkyl, and $C_1$-$C_6$haloalkyl; and
n is 1, 2, 3, or 4.

In some embodiments is a compound of Formula (IVd), or a pharmaceutically acceptable salt or solvate thereof, wherein $R_7$ and $R_8$ are independently selected from hydrogen, halogen, $C_1$-$C_6$alkyl, $C_1$-$C_6$haloalkyl, and $C_1$-$C_6$alkoxy. In some embodiments is a compound of Formula (IVd), or a pharmaceutically acceptable salt or solvate thereof, wherein $R_7$ and $R_8$ are each hydrogen. In some embodiments is a compound of Formula (IVd), or a pharmaceutically acceptable salt or solvate thereof, wherein $R_7$ and $R_8$ are each halogen. In some embodiments is a compound of Formula (IVd), or a pharmaceutically acceptable salt or solvate thereof, wherein $R_7$ and $R_8$ are each $C_1$-$C_6$alkyl. In some embodiments is a compound of Formula (IVd), or a pharmaceutically acceptable salt or solvate thereof, wherein $R_7$ is hydrogen and $R_8$ is halogen. In some embodiments is a compound of Formula (IVd), or a pharmaceutically acceptable salt or solvate thereof, wherein $R_7$ is hydrogen and $R_8$ is $C_1$-$C_6$alkyl. In some embodiments is a compound of Formula (IVd), or a pharmaceutically acceptable salt or solvate thereof, wherein $R_7$ is hydrogen and $R_8$ is $C_1$-$C_6$haloalkyl. In some embodiments is a compound of Formula (IVd), or a pharmaceutically acceptable salt or solvate thereof, wherein $R_7$ is hydrogen and $R_8$ is $C_1$-$C_6$alkoxy. In some embodiments is a compound of Formula (IVd), or a pharmaceutically acceptable salt or solvate thereof, wherein $R_7$ is hydrogen and $R_8$ is —CN. In some embodiments is a compound of Formula (IVd), or a pharmaceutically acceptable salt or solvate thereof, wherein $R_7$ is halogen and $R_8$ is hydrogen. In some embodiments is a compound of Formula (IVd), or a pharmaceutically acceptable salt or solvate thereof, wherein $R_7$ is $C_1$-$C_6$alkyl and $R_8$ is hydrogen. In some embodiments is a compound of Formula (IVd), or a pharmaceutically acceptable salt or solvate thereof, wherein $R_7$ is $C_1$-$C_6$haloalkyl and $R_8$ is hydrogen. In some embodiments is a compound of Formula (IVd), or a pharmaceutically acceptable salt or solvate thereof, wherein $R_7$ is $C_1$-$C_6$alkoxy and $R_8$ is hydrogen. In some embodiments is a compound of Formula (IVd), or a pharmaceutically acceptable salt or solvate thereof, wherein $R_7$ is —CN and $R_8$ is hydrogen.

In some embodiments is a compound of Formula (IVd), or a pharmaceutically acceptable salt or solvate thereof, wherein X is —O—. In some embodiments is a compound of Formula (IVd), or a pharmaceutically acceptable salt or solvate thereof, wherein X is —O— and n is 2. In some embodiments is a compound of Formula (IVd), or a pharmaceutically acceptable salt or solvate thereof, wherein X is —O—, n is 2, and each $R_1$ and each $R_2$ are hydrogen. In some embodiments is a compound of Formula (IVd), or a pharmaceutically acceptable salt or solvate thereof, wherein X is —O—, n is 2, each $R_1$ is hydrogen, and one $R_2$ is hydrogen and one $R_2$ is $C_1$-$C_6$alkyl. In some embodiments is a compound of Formula (IVd), or a pharmaceutically acceptable salt or solvate thereof, wherein X is —O— and n is 3. In some embodiments is a compound of Formula (IVd), or a pharmaceutically acceptable salt or solvate thereof, wherein X is —O—, n is 3, and each $R_1$ and each $R_2$ are hydrogen. In some embodiments is a compound of Formula (IVd), or a pharmaceutically acceptable salt or solvate thereof, wherein X is —O—, n is 3, one $R_1$ is $C_1$-$C_6$alkyl and one $R_2$ is $C_1$-$C_6$alkyl and the remaining $R_1$ and $R_2$ are each hydrogen.

In some embodiments is a compound of Formula (IVd), or a pharmaceutically acceptable salt or solvate thereof, wherein X is —C(R$_9$)(R$_{10}$)—. In some embodiments is a compound of Formula (IVd), or a pharmaceutically acceptable salt or solvate thereof, wherein X is —CH$_2$—. In some embodiments is a compound of Formula (IVd), or a pharmaceutically acceptable salt or solvate thereof, wherein X is —CH$_2$— and n is 1. In some embodiments is a compound of Formula (IVd), or a pharmaceutically acceptable salt or solvate thereof, wherein X is —CH$_2$—, n is 1, and R$_1$ and R$_2$ are hydrogen. In some embodiments is a compound of Formula (IVd), or a pharmaceutically acceptable salt or solvate thereof, wherein X is —CH$_2$— and n is 2. In some embodiments is a compound of Formula (IVd), or a pharmaceutically acceptable salt or solvate thereof, wherein X is —CH$_2$—, n is 2, and each R$_1$ and each R$_2$ are hydrogen. In some embodiments is a compound of Formula (IVd), or a pharmaceutically acceptable salt or solvate thereof, wherein X is —CH$_2$— and n is 3. In some embodiments is a compound of Formula (IVd), or a pharmaceutically acceptable salt or solvate thereof, wherein X is —CH$_2$—, n is 3, and each R$_1$ and each R$_2$ are hydrogen.

In some embodiments is a compound of Formula (IVd), or a pharmaceutically acceptable salt or solvate thereof, wherein R$_4$ and R$_5$ are independently selected from hydrogen and C$_1$-C$_6$alkyl. In some embodiments is a compound of Formula (IVd), or a pharmaceutically acceptable salt or solvate thereof, wherein R$_4$ is hydrogen and R$_5$ is C$_1$-C$_6$alkyl. In some embodiments is a compound of Formula (IVd), or a pharmaceutically acceptable salt or solvate thereof, wherein R$_4$ and R$_5$ are hydrogen. In some embodiments is a compound of Formula (IVd), or a pharmaceutically acceptable salt or solvate thereof, wherein R$_4$ and R$_5$ are C$_1$-C$_6$alkyl.

In some embodiments is a compound of Formula (IVd), or a pharmaceutically acceptable salt or solvate thereof, wherein R$_3$ is hydrogen. In some embodiments is a compound of Formula (IVd), or a pharmaceutically acceptable salt or solvate thereof, wherein R$_3$ is C$_1$-C$_6$alkyl.

In some embodiments is a compound of Formula (IVd), or a pharmaceutically acceptable salt or solvate thereof, wherein R$_6$ is hydrogen. In some embodiments is a compound of Formula (IVd), or a pharmaceutically acceptable salt or solvate thereof, wherein R$_6$ is C$_1$-C$_6$alkyl.

In some embodiments, provided herein is a compound selected from:

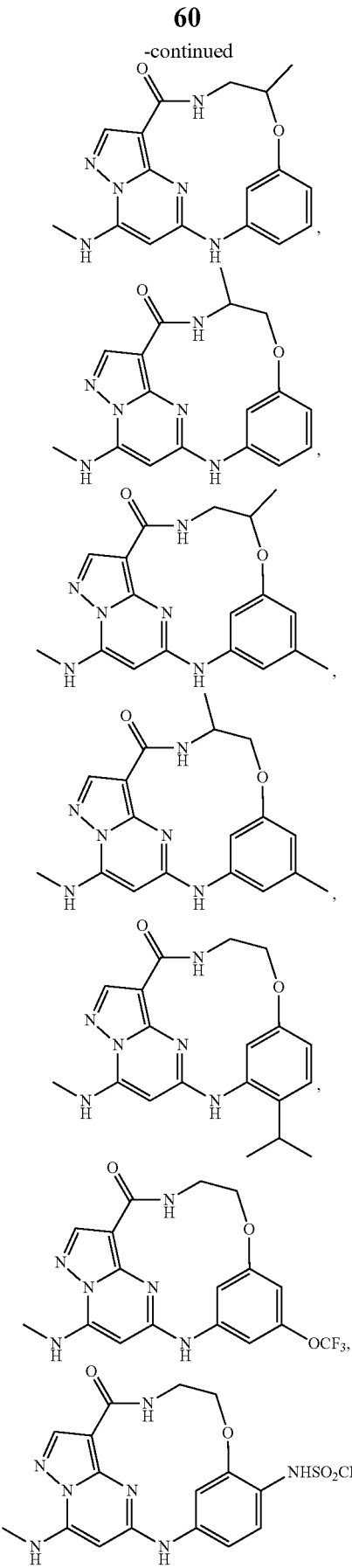

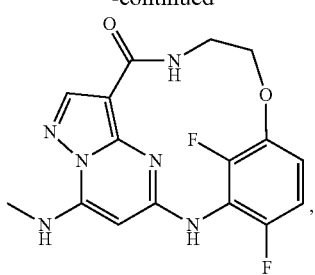,
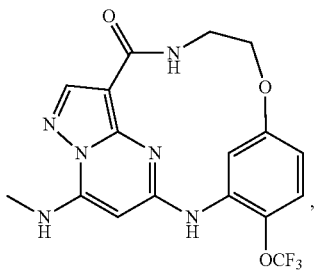,
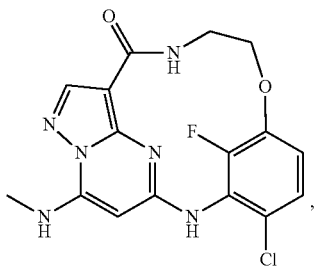,
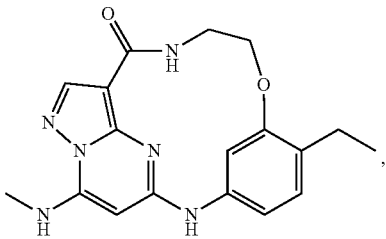,
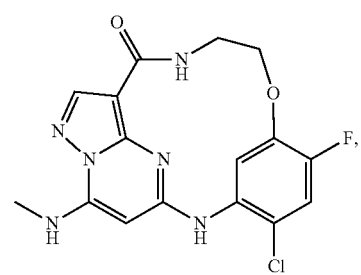,
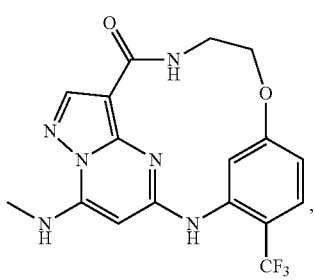,
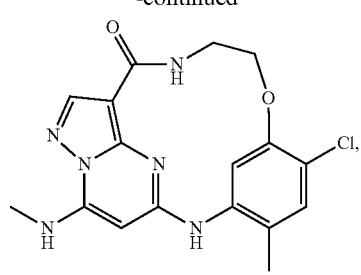
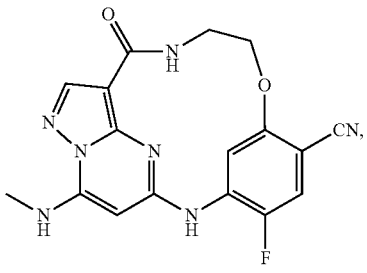,
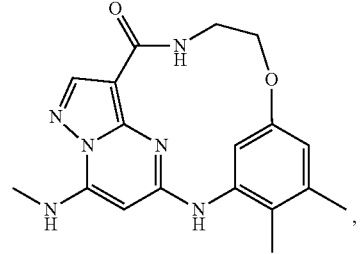,
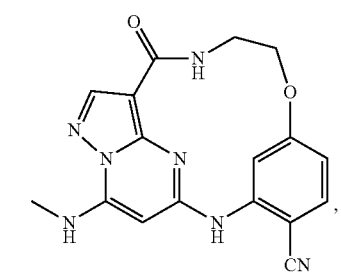,
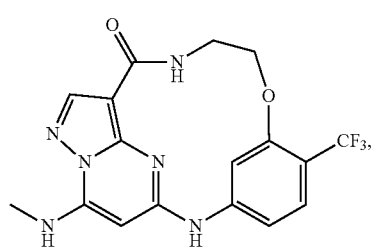,
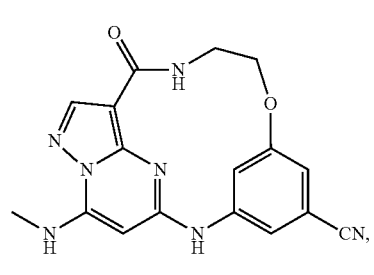,

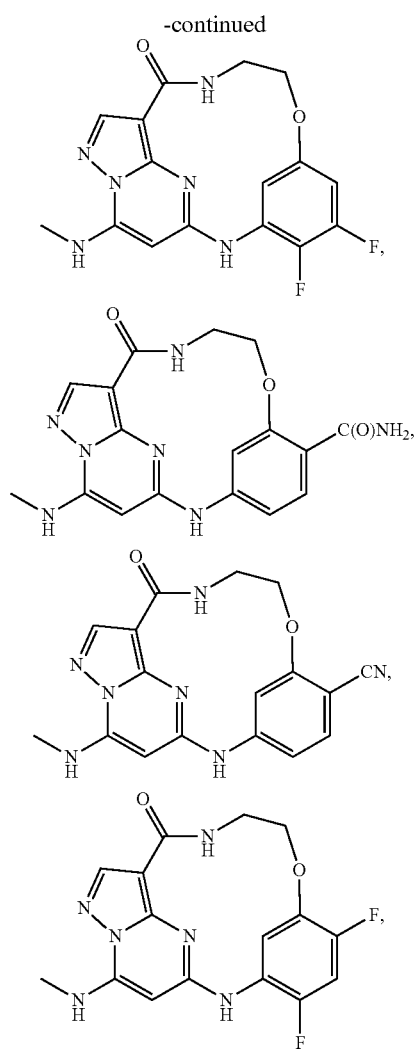
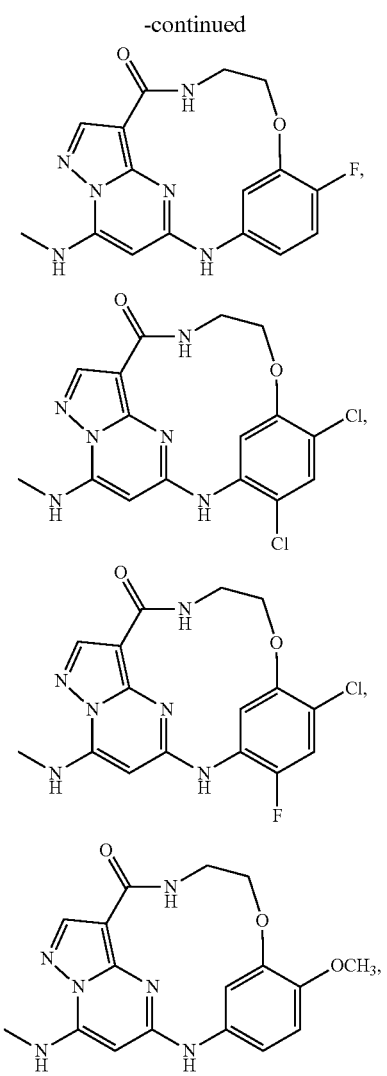

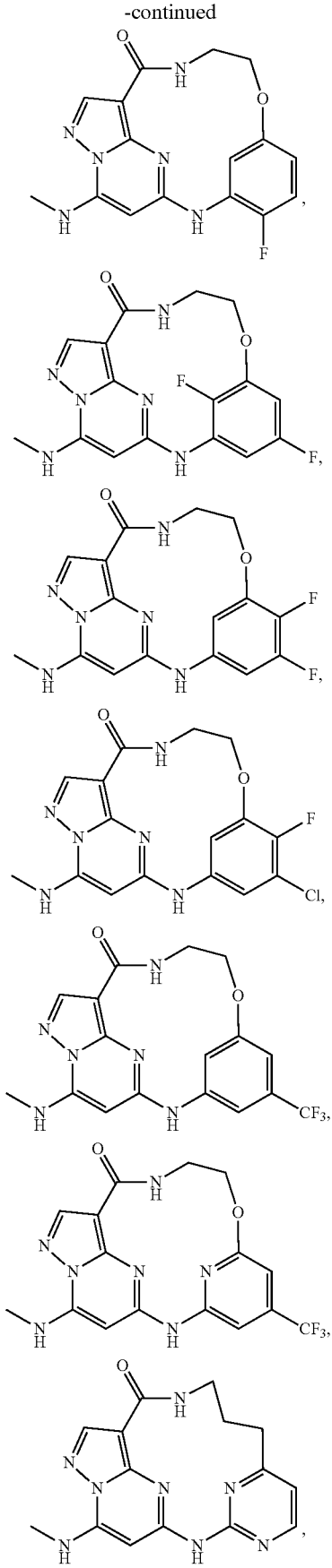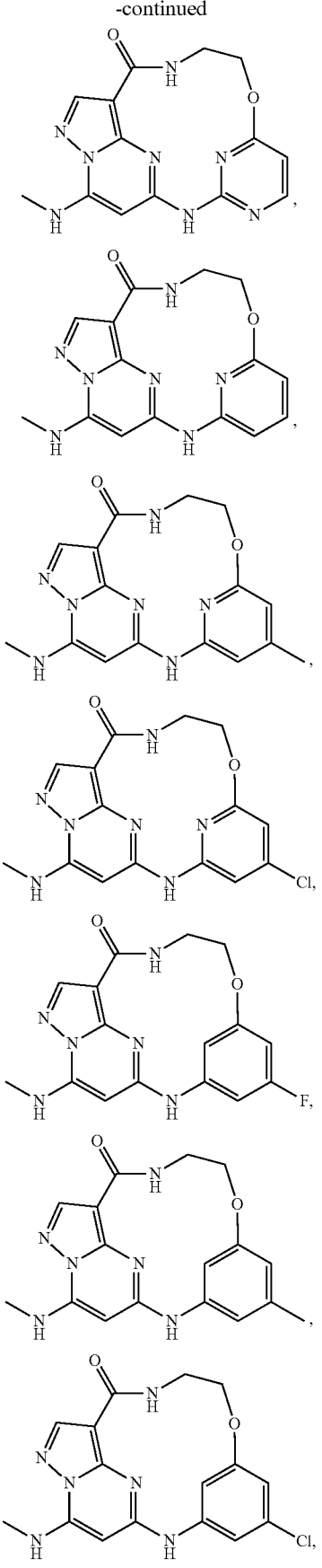

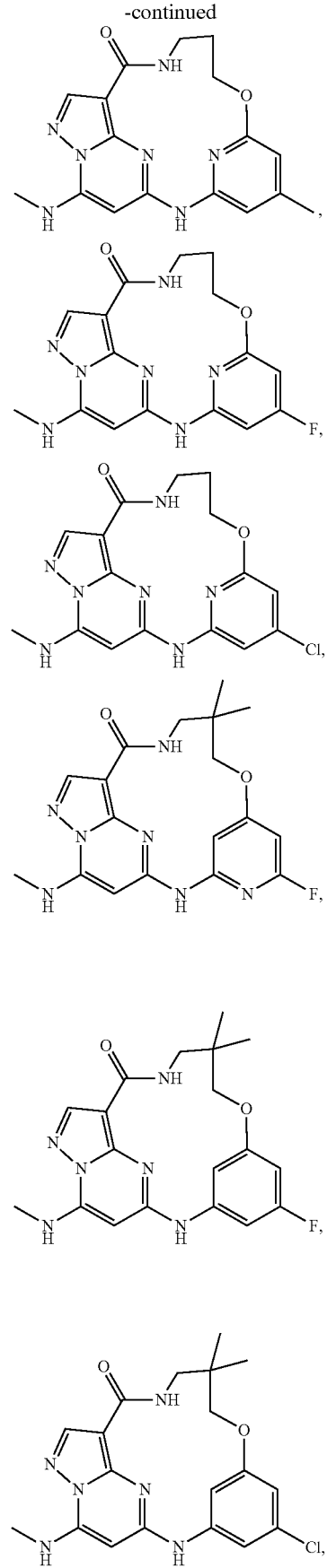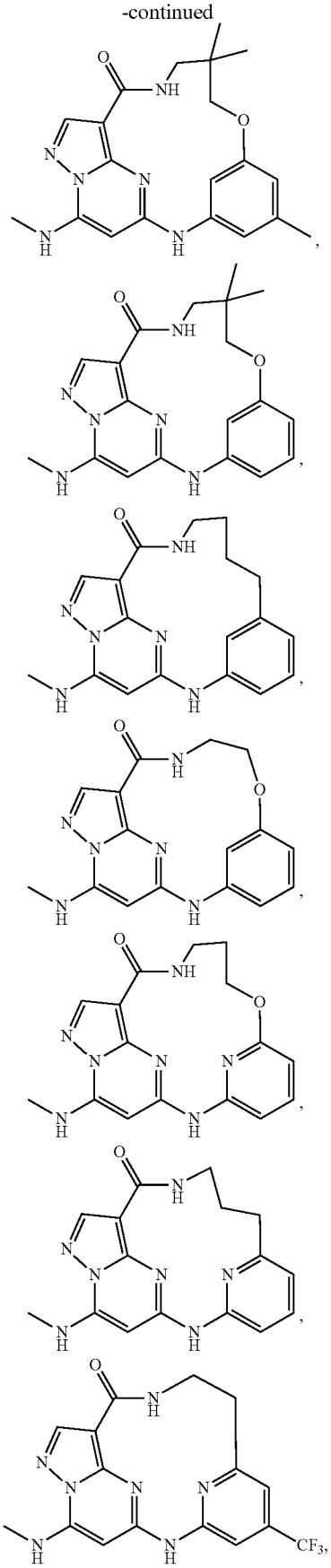

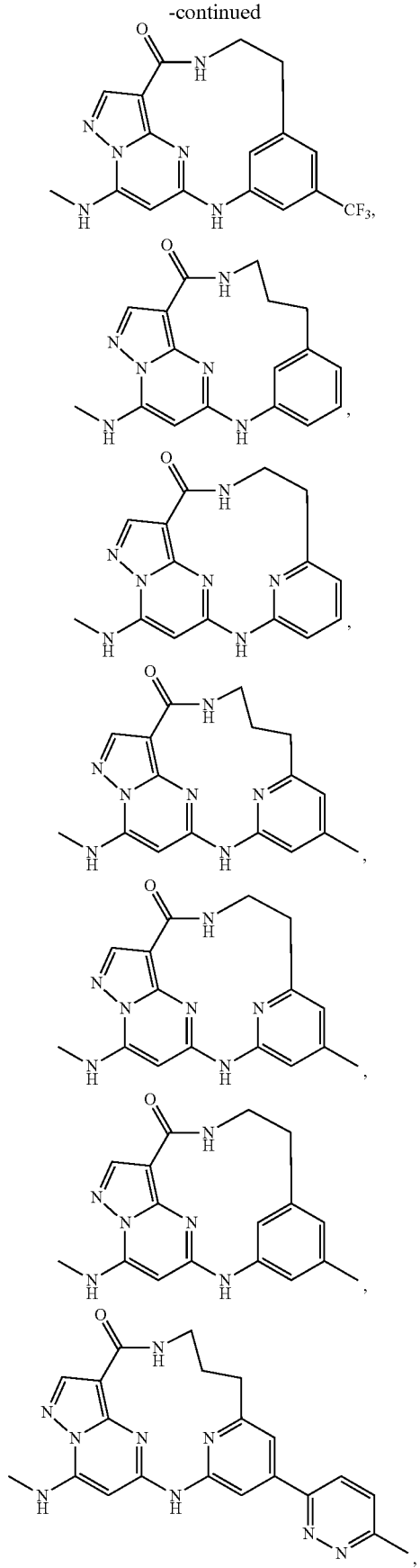
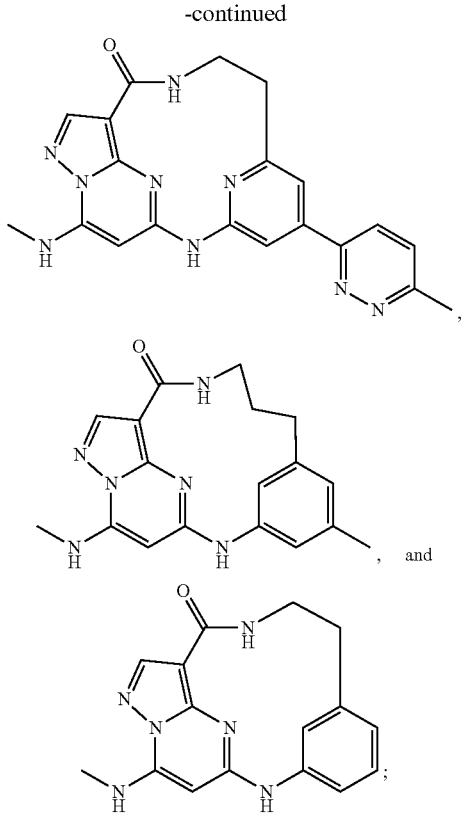
or a pharmaceutically acceptable salt or solvate thereof.
In some embodiments, provided herein is a compound selected from:
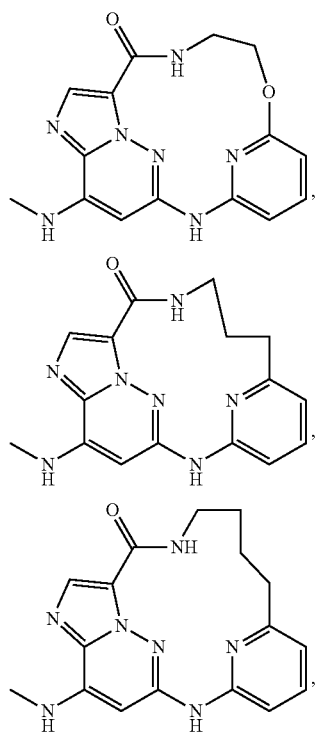

71
-continued
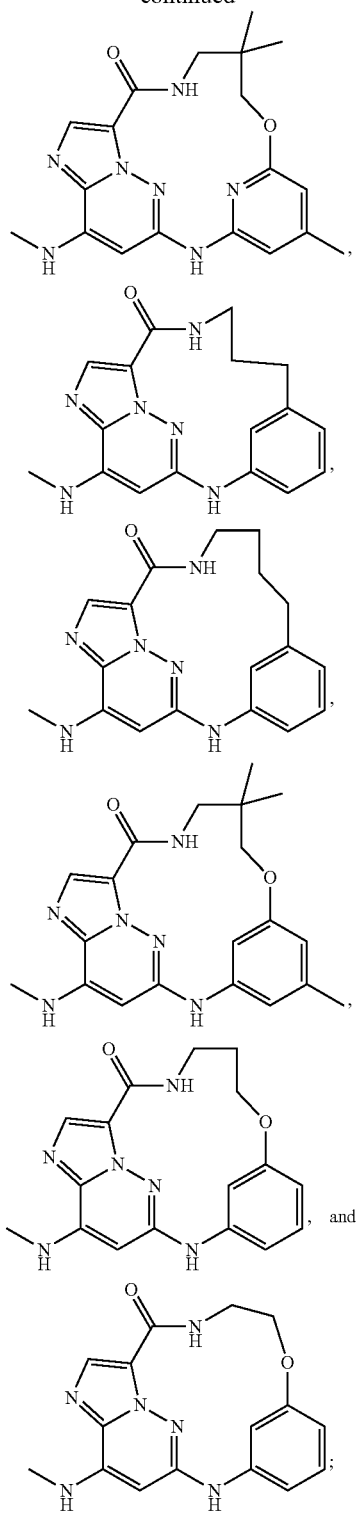
or a pharmaceutically acceptable salt or solvate thereof.
In some embodiments, provided herein is a compound selected from:
72
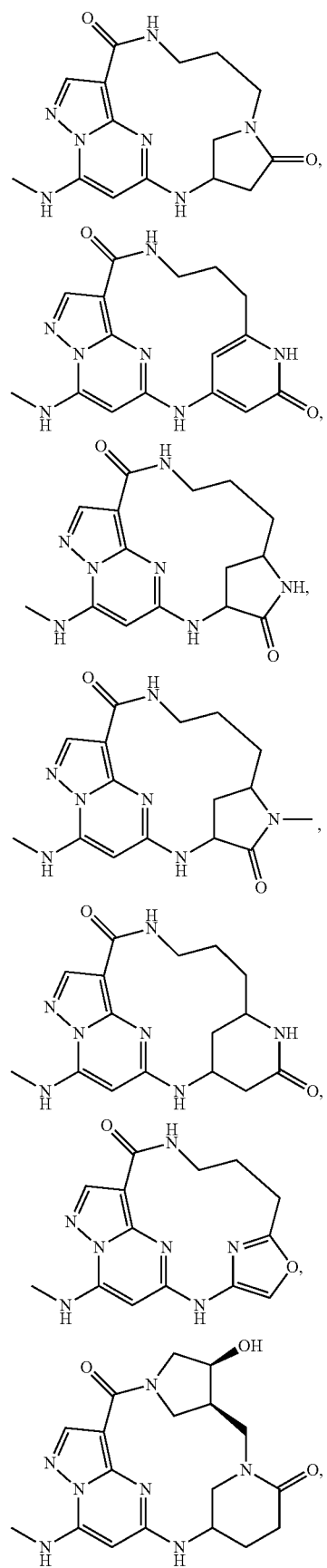

73
-continued
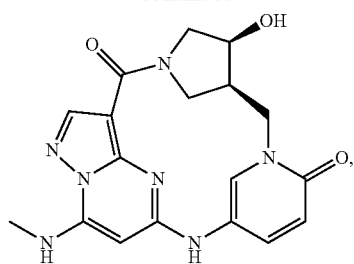
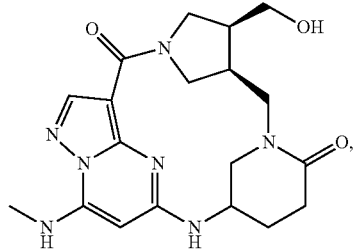
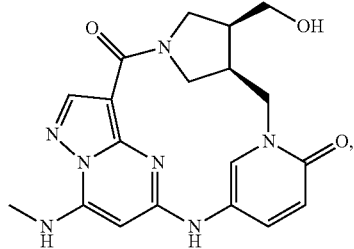
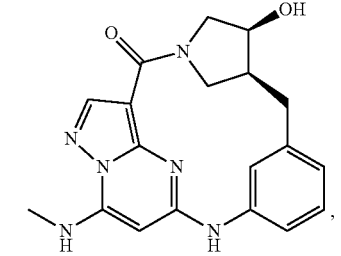
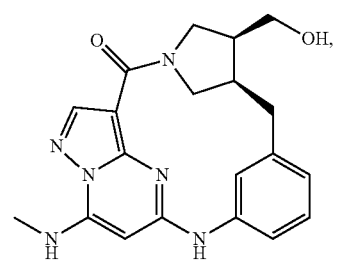
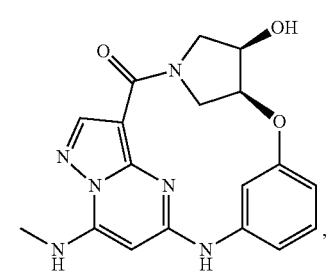
74
-continued
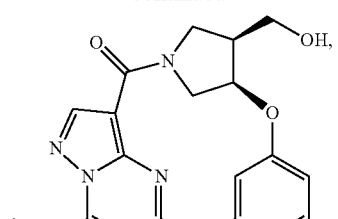
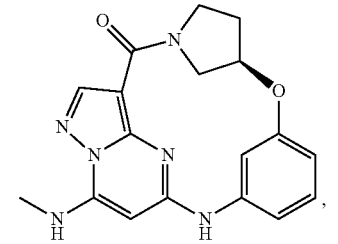
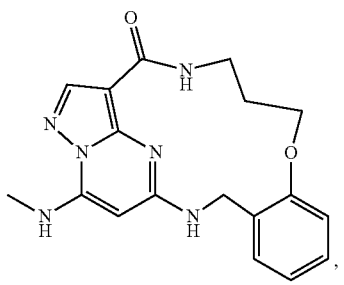
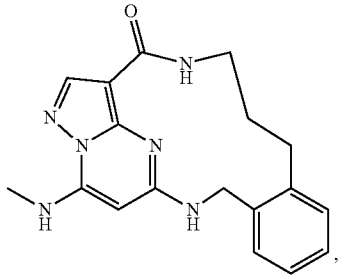
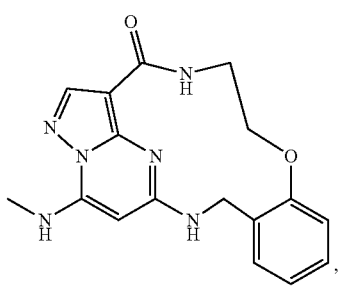
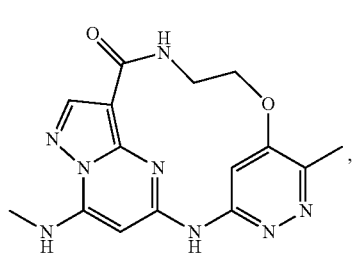

75
-continued
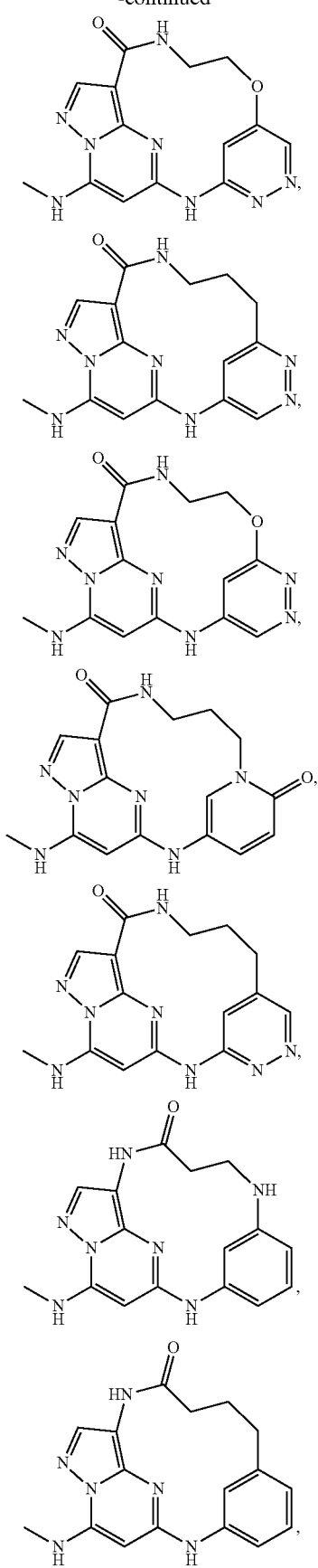
76
-continued
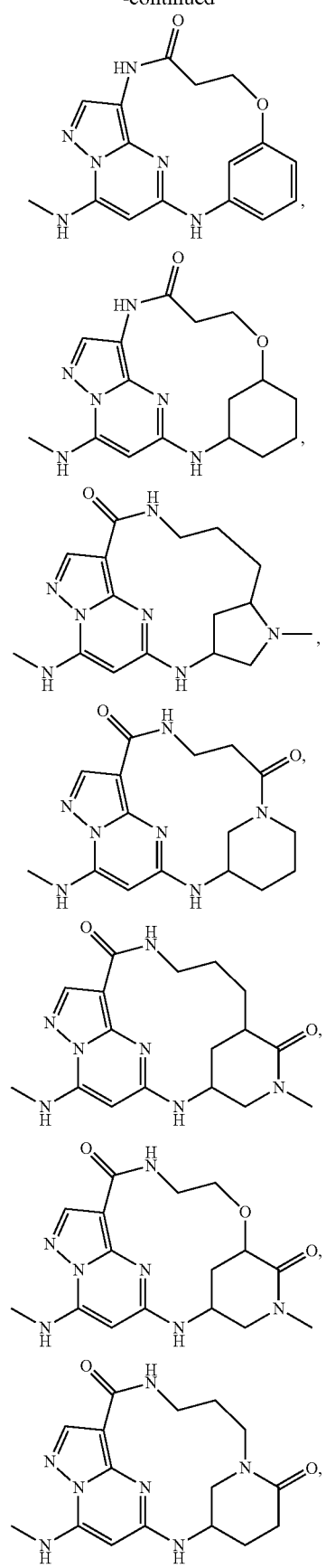

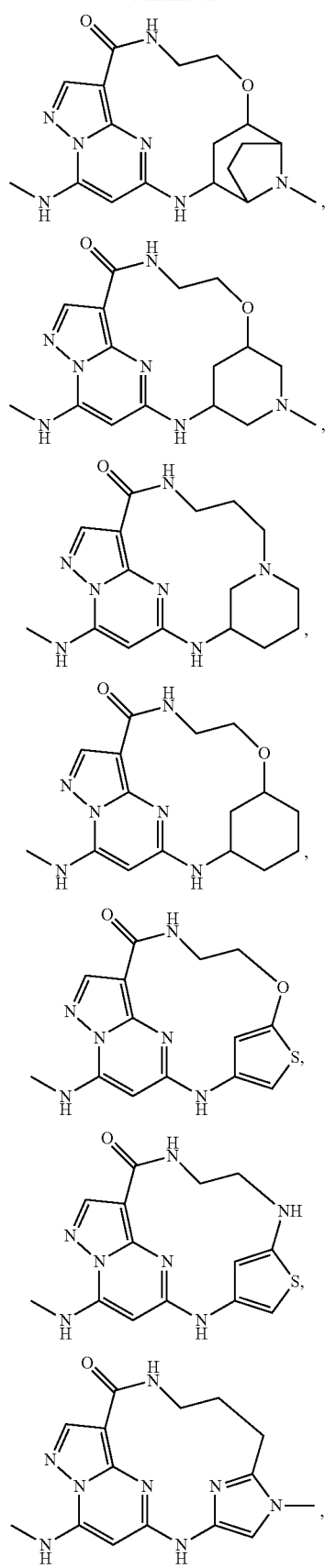
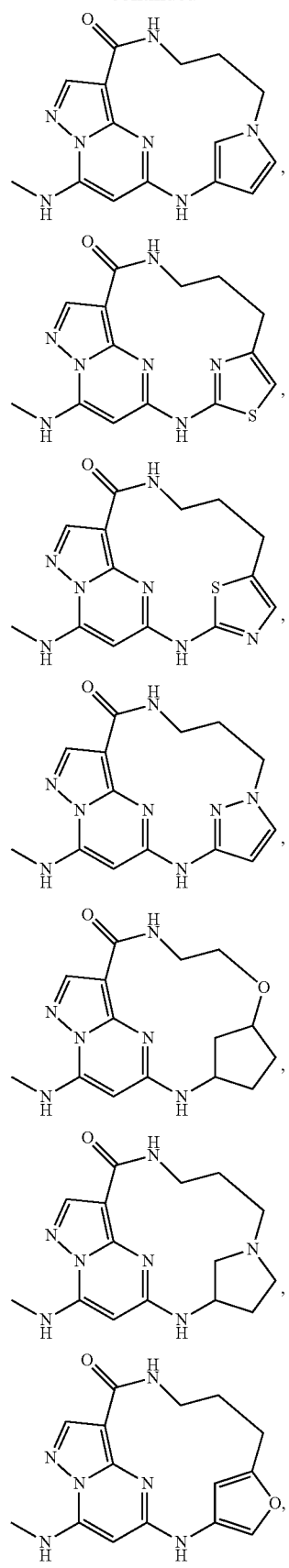

79
-continued
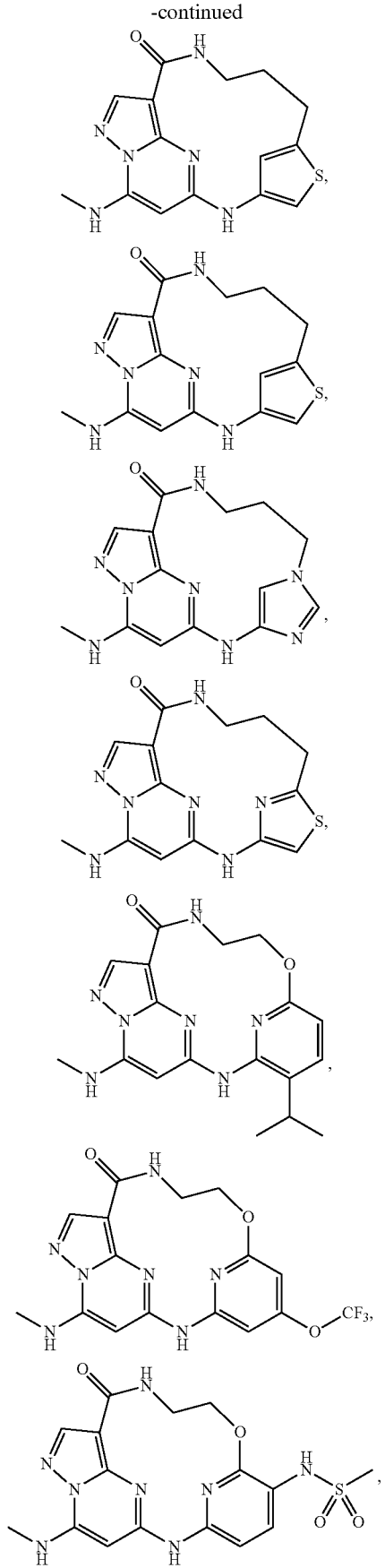
80
-continued
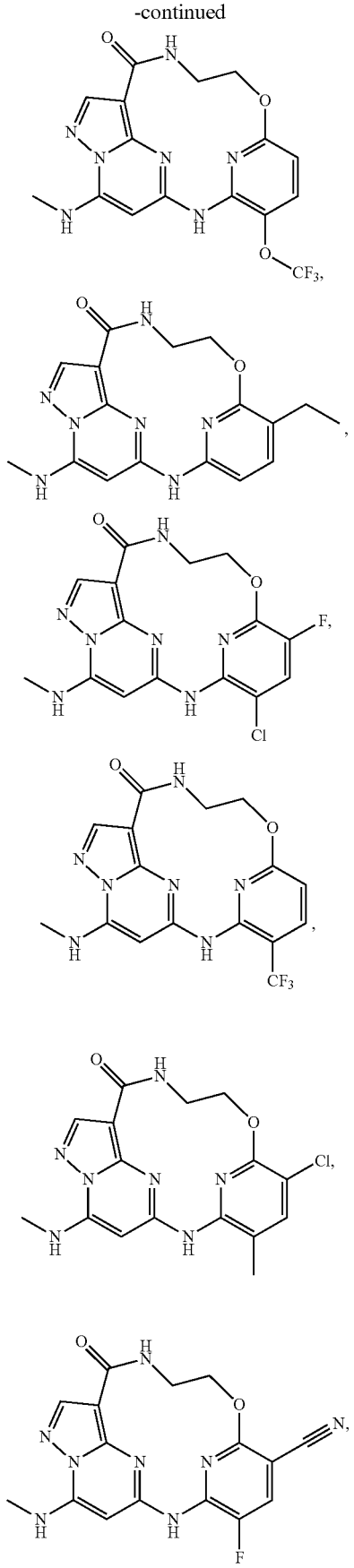

81
-continued
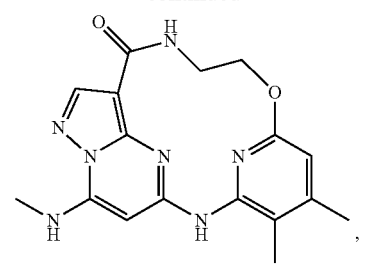
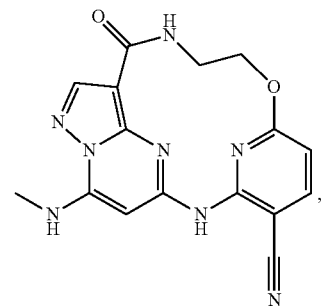
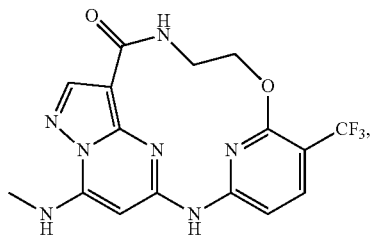
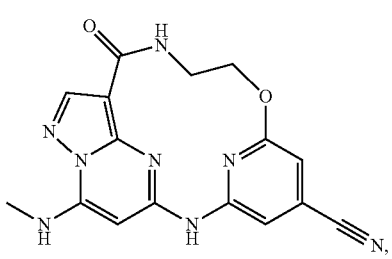
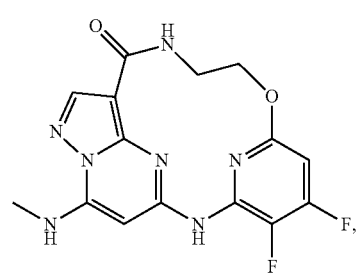
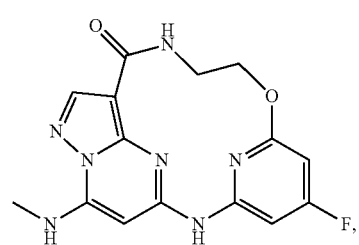
82
-continued
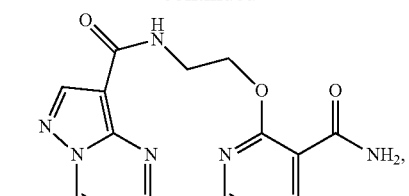
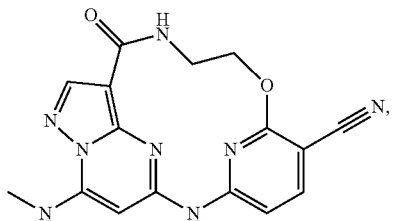
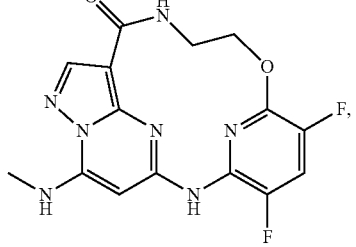
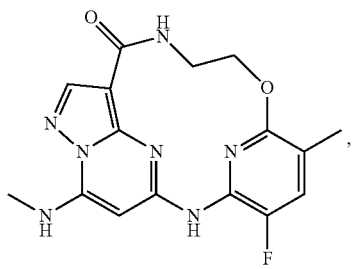
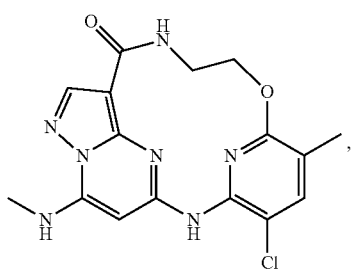
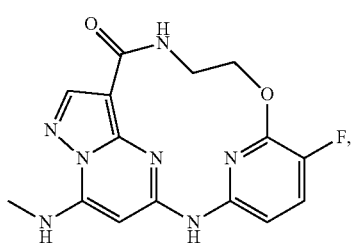

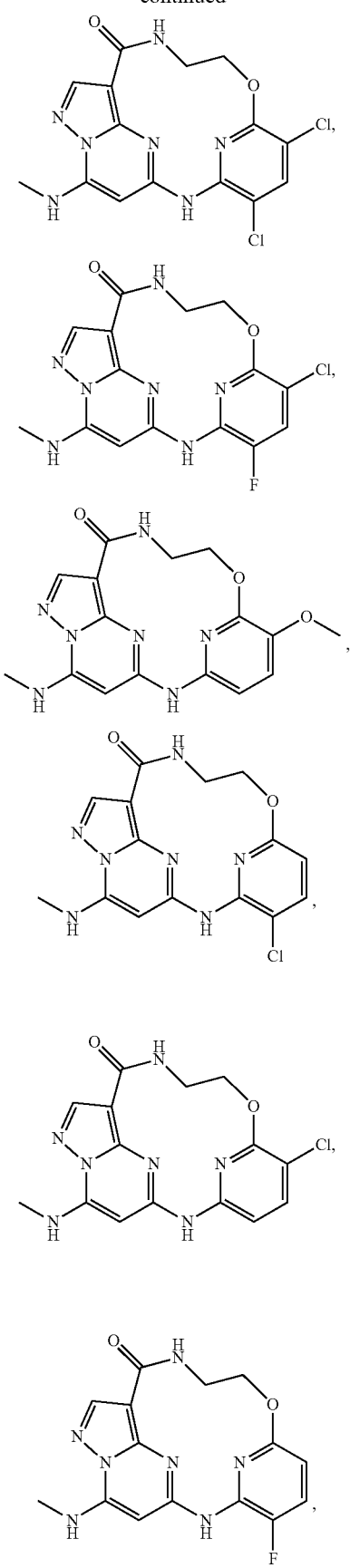
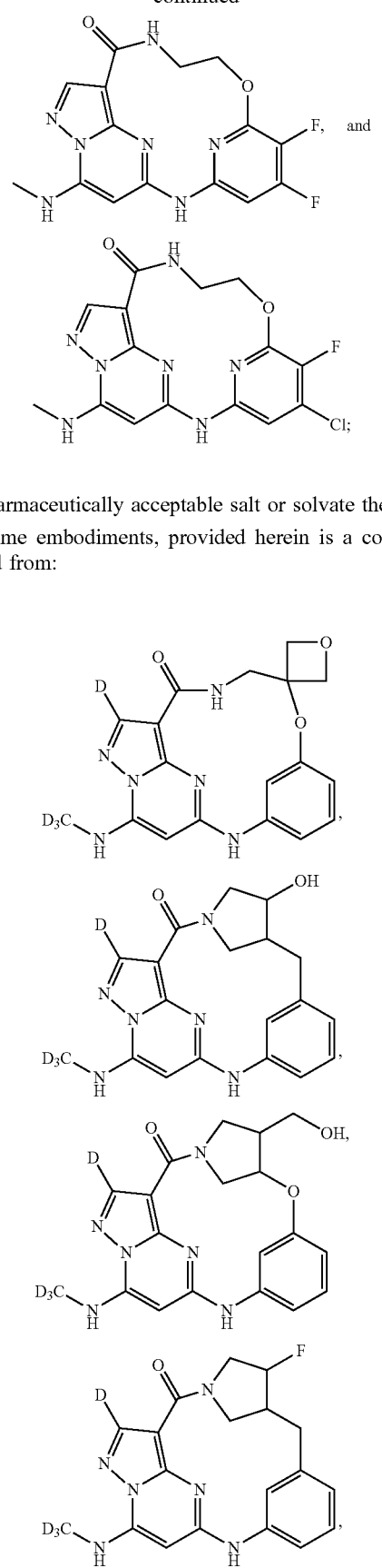
or a pharmaceutically acceptable salt or solvate thereof.
In some embodiments, provided herein is a compound selected from:

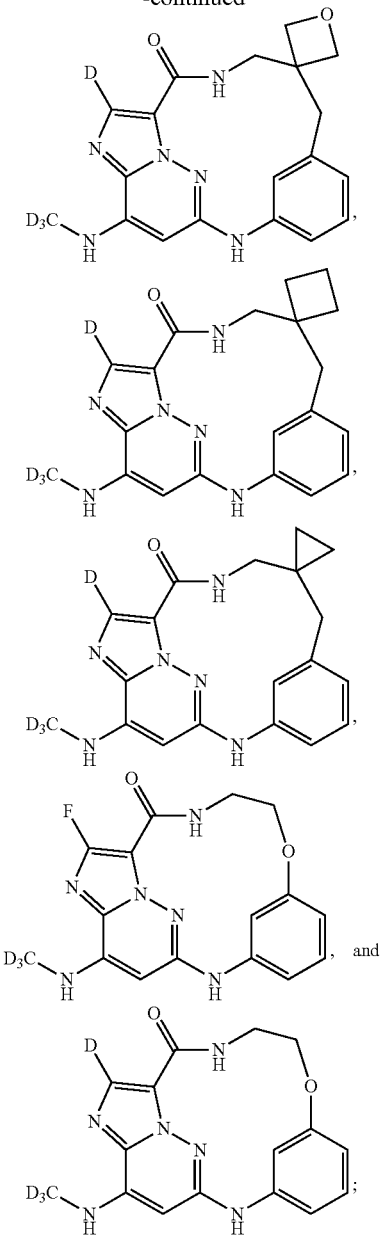
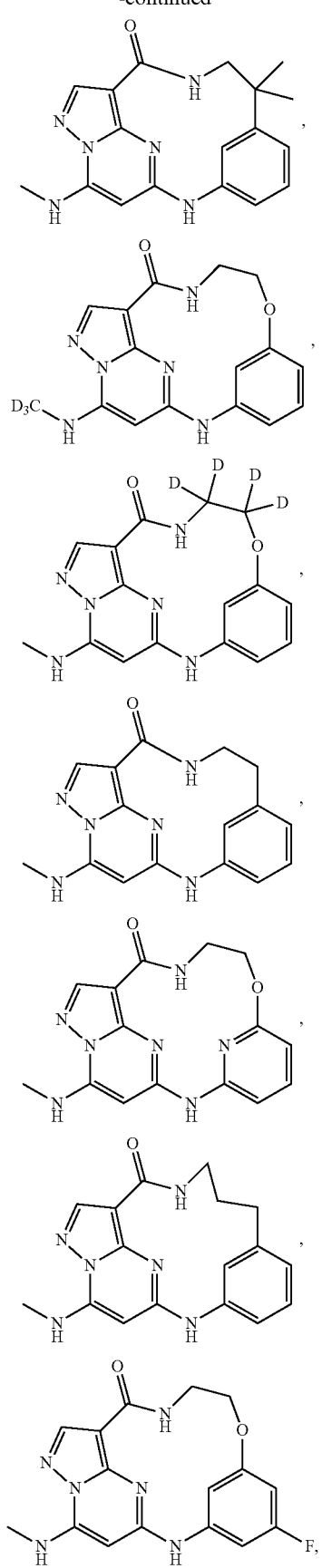
or a pharmaceutically acceptable salt or solvate thereof.
In some embodiments, provided herein is a compound selected from:
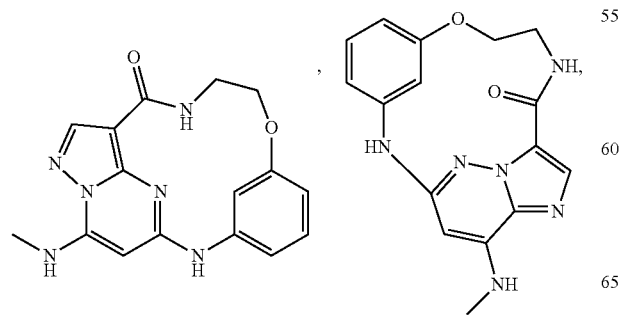

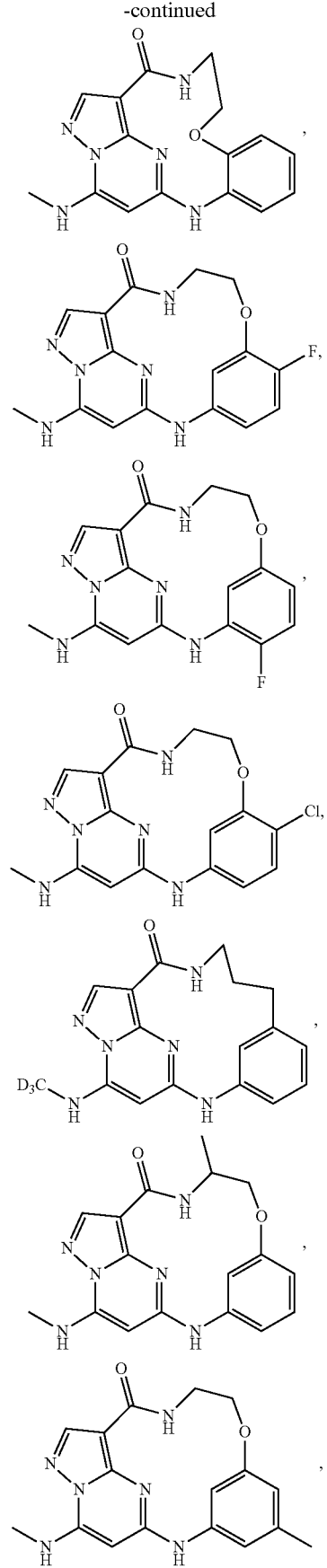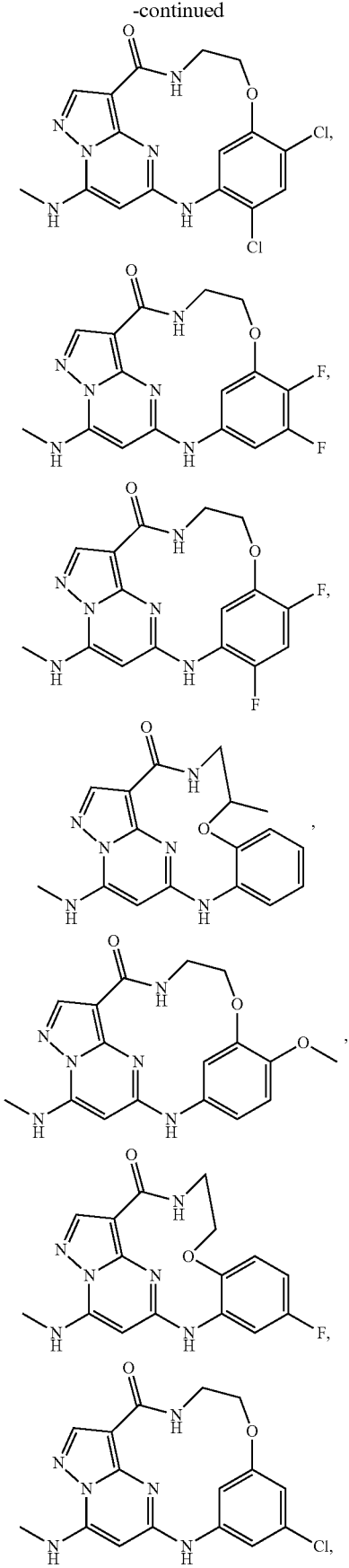

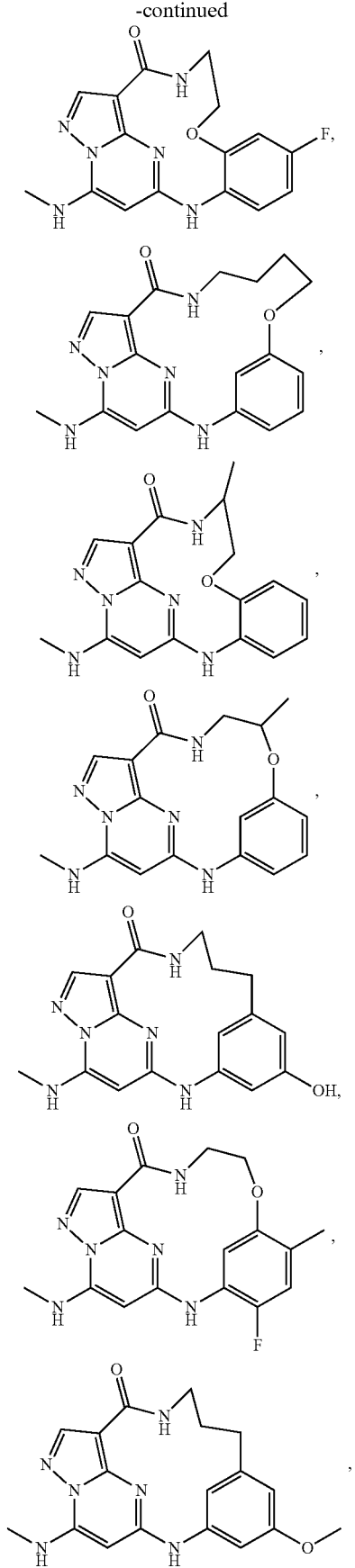
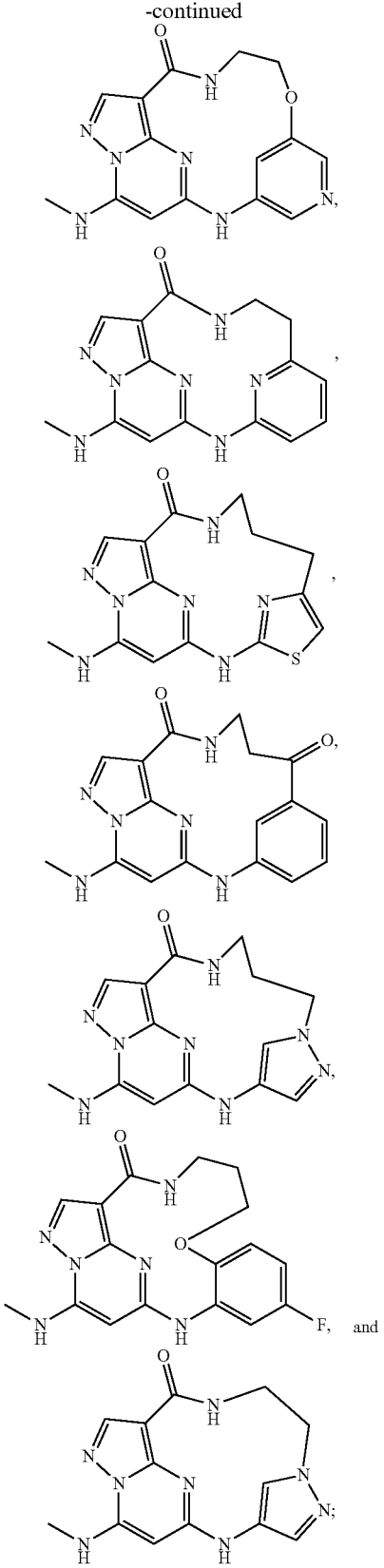
or a pharmaceutically acceptable salt or solvate thereof.
Any combination of the groups described above for the various variables is contemplated herein. Throughout the specification, groups and substituents thereof can be chosen by one skilled in the field to provide stable moieties and compounds.

In some embodiments, the therapeutic agent(s) (e.g. compound of Formula (I), (II), (III), (IIIa), (IIIb), (IIIc), (IIId), (IV), (IVa), (IVb), (IVc), or (IVd)) is present in the pharmaceutical composition as a pharmaceutically acceptable salt. In some embodiments, any compound described above is suitable for any method or composition described herein.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}$H, $^{3}$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^{3}$H and $^{11}$C are incorporated, are useful in drug and/or substrate tissue distribution assays. Tritiated, i. e., 3H and carbon-14, i.e., $^{14}$C, isotopes are particularly preferred for their ease of preparation and detectability. Further, substitution with heavy isotopes such as deuterium, i.e., $^{2}$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

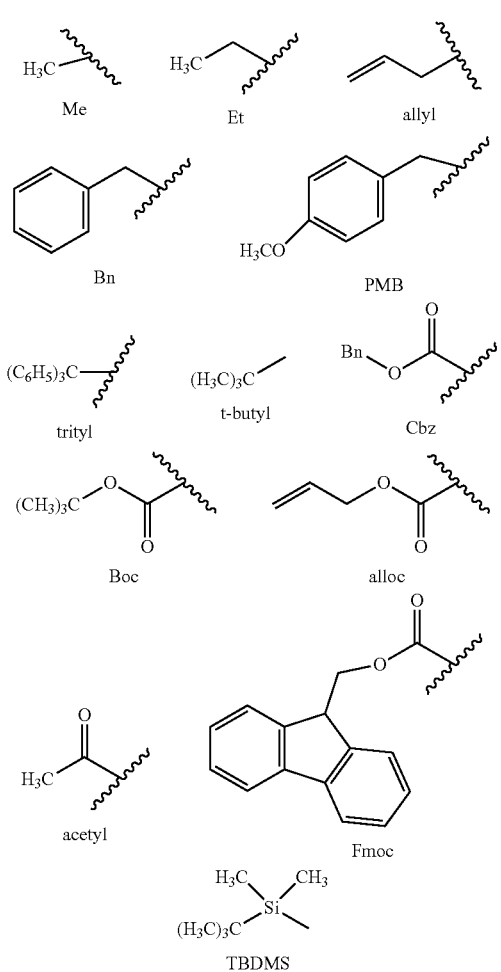

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Treatment and Prevention

In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof. In some embodiments is a method of treating an inflammatory disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof. In some embodiments is a method of treating an autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is selected from rheumatoid arthritis, multiple sclerosis, psoriasis, lupus, intestinal bowel disease, Crohn's disease, ulcerative colitis, ankylosing spondylitis, vitiligo, and atopic dermatitis. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is rheumatoid arthritis. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is multiple sclerosis. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is psoriasis. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is lupus. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is intestinal bowel disease. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is Crohn's disease. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is ulcerative colitis. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is ankylosing spondylitis. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is vitiligo. In some embodiments is a method of treating an inflammatory or autoimmune disease in a patient in need thereof, comprising administering to the patient a therapeutically effective amount of a compound Formula (I), (II), (III), (IIIa), (IIIb), (IIIc), (IIId), (IV), (IVa), (IVb), (IVc), or (IVd), or a pharmaceutically acceptable salt or solvate thereof, wherein the disease, disorder, or condition is atopic dermatitis.

Pharmaceutical Compositions and Methods of Administration

TYK2 pseudokinase ligands described herein are administered to subjects in a biologically compatible form suitable for administration to treat or prevent diseases, disorders or conditions. Administration of TYK2 pseudokinase ligands as described herein can be in any pharmacological form including a therapeutically effective amount of a TYK2 pseudokinase ligand alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments is a pharmaceutical composition comprising a pharmaceutically acceptable carrier and a compound of Formula (I), (II), (III), (IIIa), (IIIb), (IIIc), (IIId), (IV), (IVa), (IVb), (IVc), or (IVd), or a pharmaceutically acceptable salt or solvate thereof. In some embodiments is a pharmaceutical composition comprising a pharmaceutically acceptable carrier and a compound of Formula (I), or a pharmaceutically acceptable salt or solvate thereof. In some embodiments is a pharmaceutical composition comprising a pharmaceutically acceptable carrier and a compound of Formula (Ia), or a pharmaceutically acceptable salt or solvate thereof. In some embodiments is a pharmaceutical composition comprising a pharmaceutically acceptable carrier and a compound of Formula (Ib), or a pharmaceutically acceptable salt or solvate thereof. In some embodiments is a pharmaceutical composition comprising a pharmaceutically acceptable carrier and a compound of Formula (Ic), or a pharmaceutically acceptable salt or solvate thereof.

Another embodiment provides a pharmaceutical composition consisting essentially of a pharmaceutically acceptable carrier and a compound of Formula (I), (II), (III), (IIIa), (IIIb), (IIIc), (IIId), (IV), (IVa), (IVb), (IVc), or (IVd), or a pharmaceutically acceptable salt or solvate thereof. In some embodiments is a pharmaceutical composition consisting essentially of a pharmaceutically acceptable carrier and a compound of Formula (I), or a pharmaceutically acceptable salt or solvate thereof. In some embodiments is a pharmaceutical composition consisting essentially of a pharmaceutically acceptable carrier and a compound of Formula (Ia), or a pharmaceutically acceptable salt or solvate thereof. In some embodiments is a pharmaceutical composition consisting essentially of a pharmaceutically acceptable carrier and a compound of Formula (Ib), or a pharmaceutically acceptable salt or solvate thereof. In some embodiments is a pharmaceutical composition consisting essentially of a pharmaceutically acceptable carrier and a compound of Formula (Ic), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments, TYK2 pseudokinase ligands described herein are administered to subjects in a biologically compatible form suitable for topical administration to treat or prevent dermal diseases, disorders or conditions. By "biologically compatible form suitable for topical administration" is meant a form of the TYK2 pseudokinase ligand to be administered in which any toxic effects are outweighed by the therapeutic effects of the inhibitor. Administration of TYK2 pseudokinase ligands as described herein can be in any pharmacological form including a therapeutically effective amount of a TYK2 pseudokinase ligand alone or in combination with a pharmaceutically acceptable carrier.

Topical administration of a TYK2 pseudokinase ligand may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

In one embodiment, the topical composition may, for example, take the form of hydrogel based on polyacrylic acid or polyacrylamide; as an ointment, for example with polyethyleneglycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulphoxide derivatives such as dimethylsulfoxide (DMSO) or decylmethylsulfoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof, urea derivatives such as dodecylurea, 1,3-didodecylurea, and 1,3-diphenylurea; terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The carrier can also contain other pharmaceutically-acceptable excipients for modifying or maintaining the pH, osmolarity, viscosity, clarity, color, sterility, stability, rate of dissolution, or odor of the formulation. The anti-skin aging compositions can also further comprise antioxidants, sun screens, natural retinoids (e.g., retinol), and other additives commonly found in skin treatment compositions.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the TYK2 pseudokinase ligand and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the TYK2 pseudokinase ligand activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such TYK2 pseudokinase ligands can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. TYK2 pseudokinase ligands that exhibit large therapeutic indices are preferred. While TYK2 pseudokinase ligands that exhibit toxic side effects may be used, care should be taken to design a delivery system that targets such inhibitors to the site of affected tissue in order to minimize potential damage to uninfected cells and, thereby, reduce side effects.

The data obtained from the cell culture assays and animal studies can be used in formulating a range of dosage for use in humans. The dosage of such TYK2 pseudokinase ligands lies preferably within a range of circulating concentrations that include the $ED_{50}$ with little or no toxicity. The dosage may vary within this range depending upon the dosage form employed and the route of administration utilized. For any TYK2 pseudokinase ligand used in a method described herein, the therapeutically effective dose can be estimated initially from cell culture assays. A dose may be formulated in animal models to achieve a circulating plasma concentration range that includes the $IC_{50}$ (i.e., the concentration of TYK2 pseudokinase ligand that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are offered for purposes of illustration and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Standard abbreviations and acronyms as defined in *J. Org. Chem.* 2007 72(1): 23A-24A are used herein. Other abbreviations and acronyms used herein are as follows:

| | |
|---|---|
| AcOH | acetic acid |
| DMF | dimethylformamide |
| DMP | Dess-Martin periodinane |
| dppf | (diphenylphosphino)ferrocene |
| EtOAc | ethyl acetate |
| EtOH | ethanol |
| eq | equivalent |
| HBTU | N,N,N',N'-tetramethyl-O-(1H-benzotriazol-1-yl)uronium hexafluorophosphate |
| LC-MS | liquid chromatography-mass spectrometry |
| MeOH | methanol |
| TEA | triethylamine |
| rt | room temperature |

Example 1: Synthesis of ($1^3$E,$1^4$E)-$1^7$-(methylamino)-4-oxa-2,7-diaza-1(5,3)-pyrazolo[1,5-a]pyrimidina-3(1,3)-benzenacyclooctaphan-8-one (7)

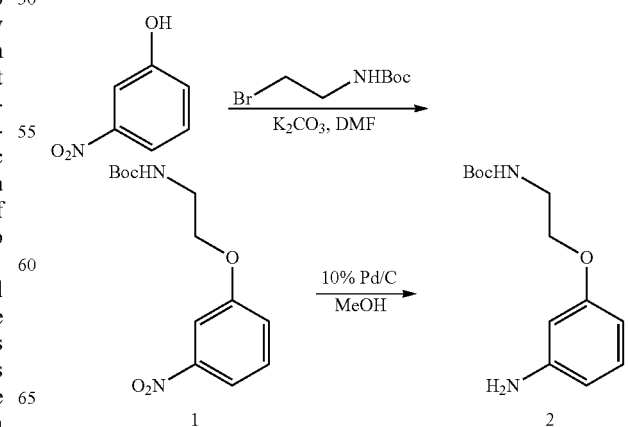

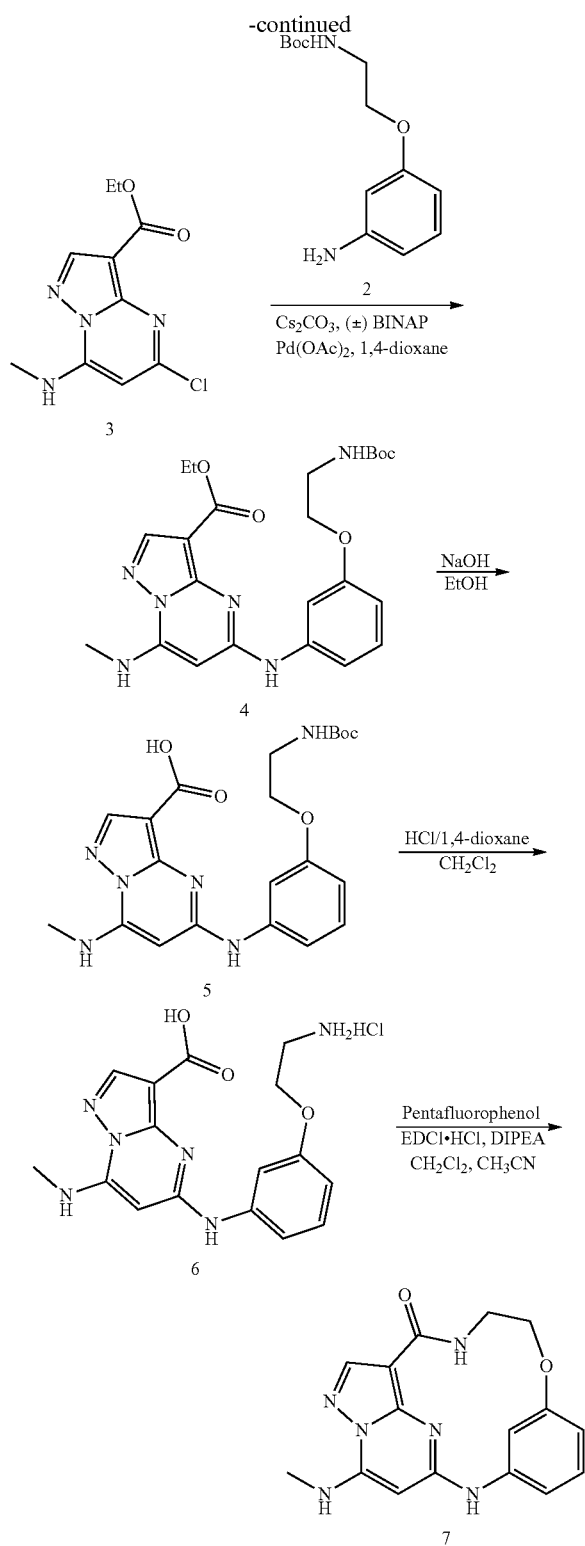

organic extracts were washed with brine (100 mL), dried over anhydrous Na$_2$SO$_4$, filtered, and concentrated under reduced pressure. The residue was purified by silica gel flash column chromatography to afford tert-butyl (2-(3-nitrophenoxy)ethyl)carbamate (1) (2.0 g, 20%) as a pale yellow semisolid. $^1$H NMR (400 MHz, CDCl$_3$): δ 7.84 (dd, J=8.1, 1.3 Hz, 1H), 7.73 (t, J=2.1 Hz, 1H), 7.44 (t, J=8.2 Hz, 1H), 7.23 (dd, J=8.3, 2.4 Hz, 1H), 4.96 (br s, 1H), 4.10 (t, J=5.2 Hz, 2H), 3.60-3.56 (m, 2H), 1.46 (s, 9H).

To a stirred solution of tert-butyl (2-(3-nitrophenoxy)ethyl)carbamate (1) (2.0 g, 7.09 mmol) in MeOH (30 mL) under inert atmosphere was added 10% Pd/C (600 mg, 50% wet) at room temperature. The reaction mixture was stirred at room temperature under hydrogen atmosphere for 4 h. The reaction mixture was filtered through a celite pad and washed with MeOH (100 mL). The filtrate was concentrated under reduced pressure to obtain tert-butyl (2-(3-aminophenoxy)ethyl)carbamate (2) (1.6 g, 90%) as a brown syrup. $^1$H NMR (400 MHz, DMSO-d$_6$): δ 6.97-6.92 (m, 1H), 6.88 (t, J=7.9 Hz, 1H), 6.17-6.10 (m, 2H), 6.06 (dd, J=8.1, 1.7 Hz, 1H), 5.01 (s, 2H), 3.82 (t, J=5.9 Hz, 2H), 3.28-3.11 (m, 2H), 1.38 (s, 9H).

To a stirred solution of ethyl 5-chloro-7-(methylamino)pyrazolo[1,5-a]pyrimidine-3-carboxylate (3) (750 mg, 2.95 mmol) in 1,4-dioxane (15 mL) under inert atmosphere were added tert-butyl (2-(3-aminophenoxy) ethyl) carbamate (2) (1.11 g, 4.42 mmol) and cesium carbonate (1.91 g, 5.90 mmol) at room temperature. The reaction mixture was purged under argon for 5 min. Then Pd(OAc)$_2$ (172 mg, 0.76 mmol) and (f) BINAP (734 mg, 1.18 mmol) were added to the reaction mixture at room temperature. The reaction mixture was stirred at 110° C. for 16 h in a sealed tube. The reaction mixture was filtered through celite and the filtrate was concentrated under reduced pressure. The crude was purified by silica gel flash column chromatography to afford ethyl 5-((3-(2-((tert-butoxycarbonyl)amino)ethoxy)phenyl)amino)-7-(methylamino)pyrazolo[1,5-a]pyrimidine-3-carboxylate (4) (800 mg, 58%) as a pale yellow solid. $^1$H NMR (400 MHz, DMSO-d$_6$): δ 9.44 (s, 1H), 8.24 (s, 1H), 7.82 (s, 1H), 7.80-7.76 (m, 1H), 7.47 (dd, J=8.1, 1.0 Hz, 1H), 7.15 (t, J=8.2 Hz, 1H), 6.94 (t, J=5.1 Hz, 1H), 6.53 (dd, J=8.2, 2.0 Hz, 1H), 5.58 (s, 1H), 4.29-4.24 (m, 2H), 4.00 (t, J=5.8 Hz, 2H), 3.32-3.28 (m, 2H), 2.90 (d, J=4.8 Hz, 3H), 1.38 (s, 9H), 1.35 (t, J=7.1 Hz, 3H).

To a stirred solution of ethyl 5-((3-(2-((tert-butoxycarbonyl)amino)ethoxy)phenyl)amino)-7-(methylamino)pyrazolo[1,5-a]pyrimidine-3-carboxylate (4) (700 mg, 1.48 mmol) in EtOH (32 mL) under inert atmosphere was added sodium hydroxide (5 mL, 2.0N in H$_2$O) at room temperature. The reaction mixture was stirred at 80° C. for 2 h. The reaction mixture was then acidified with 2.0N HCl solution and extracted with EtOAc (2×30 mL). The combined organic extracts were dried over anhydrous Na$_2$SO$_4$, filtered, and concentrated under reduced pressure to obtain 5-((3-(2-((tert-butoxycarbonyl)amino)ethoxy)phenyl)amino)-7-(methylamino)pyrazolo[1,5-a]pyrimidine-3-carboxylic acid (5) (650 g, 98%) as an off-white solid. $^1$H NMR (500 MHz, DMSO-d$_6$): δ 11.69 (br s, 1H), 9.45 (s, 1H), 8.21 (s, 1H), 8.08 (br s, 1H), 7.77 (d, J=4.6 Hz, 1H), 7.18-7.09 (m, 2H), 6.93-6.89 (m, 1H), 6.50 (d, J=7.5 Hz, 1H), 5.59 (s, 1H), 4.00 (t, J=5.5 Hz, 2H), 3.32-3.28 (m, 2H), 2.90 (d, J=4.6 Hz, 3H), 1.38 (s, 9H).

To a stirred solution of 3-nitrophenol (5.0 g, 35.97 mmol) in DMF (100 mL) under inert atmosphere were added potassium carbonate (7.44 g, 53.95 mmol) and tert-butyl (2-bromoethyl) carbamate (8.02 g, 35.97 mmol) at room temperature. The reaction mixture was stirred at 50° C. for 16 h. The reaction mixture was then diluted with water (100 mL) and extracted with EtOAc (2×100 mL). The combined To a stirred solution of 5-((3-(2-((tert-butoxycarbonyl)amino)ethoxy)phenyl)amino)-7-(methylamino)pyrazolo[1,5-a]pyrimidine-3-carboxylic acid (5) (750 mg, 1.70 mmol) in CH$_2$Cl$_2$ (21 mL) under inert atmosphere was added HCl (10 mL, 4.0Min 1, 4-dioxane) at 0° C. The reaction mixture was stirred at room temperature for 2 h. Volatiles were evaporated under reduced pressure. The residue was washed with ether (2×25 mL) and EtOAc (2×25 mL) to obtain 5-((3-(2-aminoethoxy)phenyl)amino)-7-(methylamino) pyrazolo[1,5-a]pyrimidine-3-carboxylic acid hydrochloride (6) (500 mg, 78%) as an off-white solid. $^1$H NMR (400 MHz, DMSO-$d_6$): δ 10.03 (br s, 1H), 8.33-8.22 (m, 4H), 8.14 (br s, 2H), 7.29-7.14 (m, 1H), 7.06 (d, J=7.9 Hz, 1H), 6.64 (d, J=7.1 Hz, 1H), 5.68 (s, 1H), 4.25 (t, J=5.0 Hz, 2H), 3.28-3.16 (m, 2H), 2.91 (s, 3H).

To a stirred solution 5-((3-(2-aminoethoxy)phenyl) amino)-7-(methylamino)pyrazolo[1,5-a]pyrimidine-3-carboxylic acid hydrochloride (6) (550 mg, 1.45 mmol) in CH$_2$Cl$_2$ (75 mL) under inert atmosphere were added EDCI·HCl (556 mg, 2.91 mmol) and pentafluorophenol (535 mg, 2.91 mmol) at 0° C. The reaction mixture was stirred at room temperature for 2 h. Volatiles were evaporated under reduced pressure. The residue was co-distilled with n-pentane (20 mL) and concentrated under reduced pressure. To a solution of the residue in CH$_3$CN (15.0 mL) at 70° C. was added diisopropyl ethyl amine (3 mL, 17.46 mmol) in CH$_3$CN (94 mL) dropwise at 70° C. The reaction mixture was stirred at 70° C. for 3 h. The reaction mixture was diluted with saturated ammonium chloride solution (100 mL) and extracted with EtOAc (2×100 mL). The combined organic extracts were washed with 1N HCl solution (30 mL), water (30 mL), brine (30 mL), dried over anhydrous Na$_2$SO$_4$, filtered, and concentrated under reduced pressure. The residue was purified by silica gel flash column chromatography to afford ($1^3$E,$1^4$E)-$1^7$-(methylamino)-4-oxa-2,7-diaza-1(5,3)-pyrazolo[1,5-a]pyrimidina-3(1,3)-benzenacyclooctaphan-8-one (7) (25 mg, 5%) as an off-white solid. $^1$H NMR (400 MHz, DMSO-$d_6$): δ 9.73 (t, J=4.6 Hz, 1H), 9.66 (s, 1H), 8.10 (s, 1H), 8.01-7.93 (m, 2H), 7.18 (t, J=8.0 Hz, 1H), 6.66-6.57 (m, 2H), 5.42 (s, 1H), 4.52-4.38 (m, 2H), 3.61 (br s, 2H), 2.93 (d, J=4.8 Hz, 3H); LCMS: 99.28%; 325.2 (M+H)$^+$.

Example 2: Synthesis of (E)-$1^8$-(methylamino)-4-oxa-2,7-diaza-1(6,3)-imidazo[1,2-b]pyridazina-3(1,3)-benzenacyclooctaphan-8-one (12)

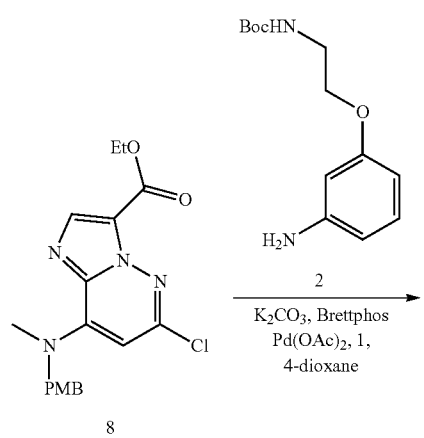

To a stirred solution of ethyl 6-chloro-8-((4-methoxybenzyl)(methyl)amino)imidazo[1,2-b]pyridazine-3-carboxylate (8) (1.2 g, 3.20 mmol) in 1,4-dioxane (24 mL) under inert atmosphere were added tert-butyl (2-(3-aminophenoxy) ethyl) carbamate (2) (970 mg, 3.85 mmol) and potassium carbonate (885 mg, 6.41 mmol) at room temperature. The reaction mixture was purged under argon for 5 min. Then Pd(OAc)$_2$ (144 mg, 0.64 mmol) and brettphos (344 mg, 0.64 mmol) were added to the reaction mixture at room temperature. The reaction mixture was stirred at 110° C. for 2 h in a sealed tube. The reaction mixture was diluted with water (100 mL) and extracted with EtOAc (2×100 mL). The combined organic extracts were washed with water (100 mL), dried over anhydrous Na$_2$SO$_4$, filtered, and concentrated under reduced pressure. The residue was purified by silica gel flash column chromatography to afford ethyl 6-((3-(2-((tert-butoxycarbonyl)amino)ethoxy)phenyl)amino)-8-((4-methoxybenzyl)(methyl)amino)imidazo[1,2-b]pyridazine-3-carboxylate (9) (1.5 g, 2.54 mmol, 79%) as a pale yellow solid. $^1$H NMR (400 MHz, DMSO-d$_6$): δ 9.07 (s, 1H), 8.02 (s, 1H), 7.79 (s, 1H), 7.26 (d, J=8.2 Hz, 1H), 7.18-7.12 (m, 3H), 6.95-6.92 (m, 1H), 6.87 (d, J=8.7 Hz, 2H), 6.48 (dd, J=7.9, 1.8 Hz, 1H), 5.97 (s, 1H), 5.39 (s, 2H), 4.43-4.38 (m, 2H), 4.04 (t, J=5.7 Hz, 2H), 3.71 (s, 3H), 3.35-3.27 (m, 2H), 3.06 (s, 3H), 1.42-1.31 (m, 12H).

To a stirred solution of ethyl 6-((3-(2-((tert-butoxycarbonyl)amino)ethoxy)phenyl)amino)-8-((4-methoxybenzyl)(methyl)amino)imidazo[1,2-b]pyridazine-3-carboxylate (9) (1.5 g, 2.54 mmol) in EtOH (45 mL) under inert atmosphere was added sodium hydroxide (7.5 mL, 2.0N in water) at 0° C. The reaction mixture was stirred at 80° C. for 90 min. The reaction mixture was then acidified with 2 N HCl solution and concentrated under reduced pressure. The residue was extracted with EtOAc (2×100 mL). The combined organic extracts were dried over anhydrous Na$_2$SO$_4$, filtered, and concentrated under reduced pressure to obtain 6-((3-(2-((tert-butoxycarbonyl)amino)ethoxy)phenyl)amino)-8-((4-methoxybenzyl)(methyl)amino)imidazo[1,2-b]pyridazine-3-carboxylic acid (10) (1.2 g, 2.13 mmol, 84%) as an off-white solid. $^1$H NMR (400 MHz, DMSO-d$_6$): δ 12.74 (br s, 1H), 9.06 (s, 1H), 7.99 (s, 1H), 7.68 (s, 1H), 7.24-7.08 (m, 4H), 6.92 (t, J=4.8 Hz, 1H), 6.88 (d, J=8.68 Hz, 2H), 6.48 (dd, J=8.1, 1.6 Hz, 1H), 5.95 (s, 1H), 5.39 (s, 2H), 4.02 (t, J=5.6 Hz, 2H), 3.71 (s, 3H), 3.32-3.30 (m, 2H), 3.07 (s, 3H), 1.38 (s, 9H).

To a stirred solution of 6-((3-(2-((tert-butoxycarbonyl)amino)ethoxy)phenyl)amino)-8-((4-methoxybenzyl)(methyl)amino)imidazo[1,2-b]pyridazine-3-carboxylic acid (10) (1.0 g, 1.77 mmol) in CH$_2$Cl$_2$ (20 mL) under inert atmosphere was added HCl (10 mL, 4.0M in 1, 4-dioxane) at 0° C. The reaction mixture was stirred at room temperature for 16 h. Volatiles were evaporated under reduced pressure. The residue was washed with ether (2×25 mL) and EtOAc (2×25 mL) to obtain 6-((3-(2-aminoethoxy)phenyl)amino)-8-(methylamino)imidazo[1,2-b]pyridazine-3-carboxylic acid (11) (650 mg, crude) as an off-white solid. $^1$H NMR (400 MHz, DMSO-d$_6$): δ 9.44 (s, 1H), 8.22-8.18 (m, 4H), 7.98 (s, 1H), 7.70-7.65 (m, 1H), 7.30-7.13 (m, 2H), 6.55 (d, J=7.8 Hz, 1H), 6.05 (s, 1H), 4.27 (t, J=4.8 Hz, 2H), 3.25-3.18 (m, 2H), 2.89 (s, 3H).

To a stirred solution 6-((3-(2-aminoethoxy)phenyl)amino)-8-(methylamino)imidazo[1,2-b]pyridazine-3-carboxylic acid (11) (550 mg, 1.60 mmol) in CH$_2$Cl$_2$:DMF (4:1) (55 mL) under inert atmosphere were added FDDP (803 mg, 2.09 mmol) and diisopropyl ethyl amine (2.24 mL, 12.86 mmol) at room temperature. The reaction mixture was stirred at 70° C. for 1 h. The reaction mixture was quenched with 2.0M sodium carbonate solution (150 mL) and extracted with EtOAc (2×100 mL). The combined organic extracts were washed with water (100 mL), brine (50 mL), dried over anhydrous Na$_2$SO$_4$, filtered, and concentrated under reduced pressure. The crude was purified by silica gel flash column chromatography to afford (E)-18-(methylamino)-4-oxa-2,7-diaza-1(6,3)-imidazo[1,2-b]pyridazina-3(1,3)-benzenacyclooctaphan-8-one (12) (14 mg, 3%) as an off-white solid. $^1$H NMR (400 MHz, DMSO-d$_6$): δ 10.36 (t, J=4.8 Hz, 1H), 9.21 (s, 1H), 7.87 (s, 1H), 7.78 (s, 1H), 7.58 (d, J=4.9 Hz, 1H), 7.18 (t, J=8.1 Hz, 1H), 6.63 (d, J=7.6 Hz, 1H), 6.58 (dd, J=8.3, 2.0 Hz, 1H), 5.70 (s, 1H), 4.57-4.43 (m, 2H), 3.71-3.67 (m, 2H), 2.89 (d, J=4.8 Hz, 3H); LCMS: 94.74%; 325.3 (M+H)$^+$.

Compounds 13-47 were prepared by similar procedures as described in the preceding Examples.

| Compound | Structure | Name | MS [M + H]$^+$ |
|---|---|---|---|
| 13 | 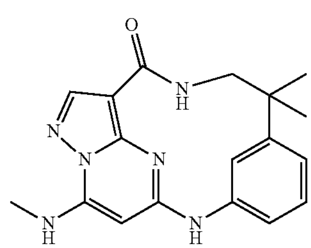 | (1$^3$E,1$^4$E)-4,4-dimethyl-1$^7$-(methylamino)-2,6-diaza-1(5,3)-pyrazolo[1,5-a]pyrimidina-3(1,3)-benzenacycloheptaphan-7-one | 337.3 |
| 14 | 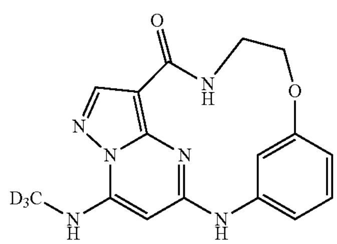 [SMILES: [2H]C([2H])([2H])Nc1cc2nc3c(cnn13)C(=O)NCCOc1cccc(c1)N2] | (1$^3$E,1$^4$E)-1$^7$-((methyl-d$_3$)amino)-4-oxa-2,7-diaza-1(5,3)-pyrazolo[1,5-a]pyrimidina-3(1,3)-benzenacyclooctaphan-8-one | 328.4 |

-continued

| Compound | Structure | Name | MS [M + H]+ |
|---|---|---|---|
| 15 | 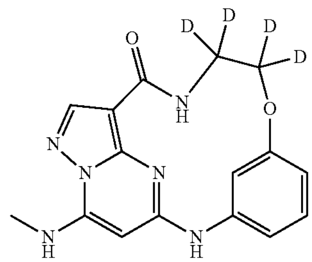 [SMILES: [2H]C1([2H])NC(=O)c2cnn3c(NC)cc(nc23)Nc2cccc(c2)OC1([2H])[2H]] | (1³E,1⁴E)-1⁷-(methylamino)-4-oxa-2,7-diaza-1(5,3)-pyrazolo[1,5-a]pyrimidina-3(1,3)-benzenacyclooctaphn-8-one-5,5,6,6-d4 | 329.3 |
| 16 | 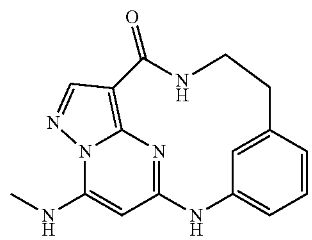 [SMILES: CNc1cc2nc3c(cnn13)C(=O)NCCc1cccc(c1)N2] | (1³E,1⁴E)-1⁷-(methylamino)-2,6-diaza-1(5,3)-pyrazolo[1,5-a]pyrimidina-3(1,3)-benzenacycloheptaphan-7-one | 309.0 |
| 17 | 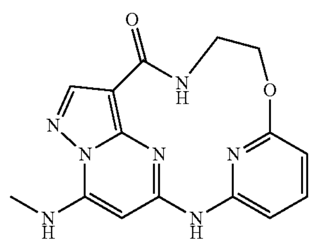 [SMILES: CNc1cc2nc3c(cnn13)C(=O)NCCOc1cccc(n1)N2] | (1³E,1⁴E)-1⁷-(methylamino)-4-oxa-2,7-diaza-1(5,3)-pyrazolo[1,5-a]pyrimidina-3(2,6)-pyridinacyclooctaphan-8-one | 326.4 |
| 18 | 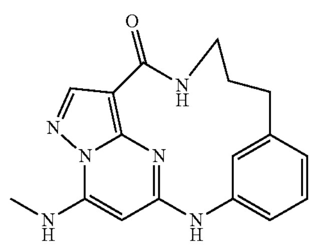 [SMILES: CNc1cc2nc3c(cnn13)C(=O)NCCCc1cccc(c1)N2] | (1³E,1⁴E)-1⁷-(methylamino)-2,7-diaza-1(5,3)-pyrazolo[1,5-a]pyrimidina-3(1,3)-benzenacyclooctaphan-8-one | 323.6 |
| 19 | 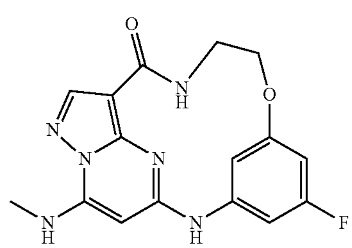 [SMILES: CNc1cc2nc3c(cnn13)C(=O)NCCOc1cc(F)cc(c1)N2] | (1³E,1⁴E)-3⁵-fluoro-1⁷-(methylamino)-4-oxa-2,7-diaza-1(5,3)-pyrazolo[1,5-a]pyrimidina-3(1,3)-benzenacyclooctaphan-8-one | 343.2 |
| 20 | 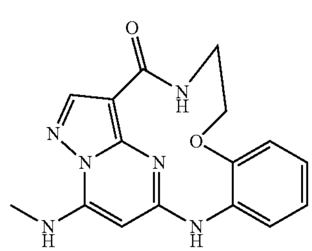 [SMILES: CNc1cc2nc3c(cnn13)C(=O)NCCOc1ccccc1N2] | (1³E,1⁴E)-1⁷-(methylamino)-4-oxa-2,7-diaza-1(5,3)-pyrazolo[1,5-a]pyrimidina-3(1,2)-benzenacyclooctaphan-8-one | 324.5 |

-continued

| Compound | Structure | Name | MS [M + H]⁺ |
|---|---|---|---|
| 21 | 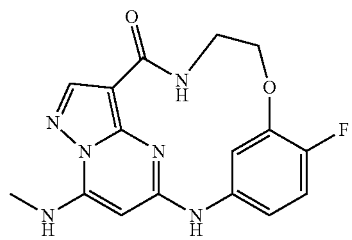 [SMILES: CNc1cc2nc3c(cnn13)C(=O)NCCOc1cc(ccc1F)N2] | (1³E,1⁴E)-3⁴-fluoro-1⁷-(methylamino)-4-oxa-2,7-diaza-1(5,3)-pyrazolo[1,5-a]pyrimidina-3(1,3)-benzenacyclooctaphan-8-one | 343.3 |
| 22 | 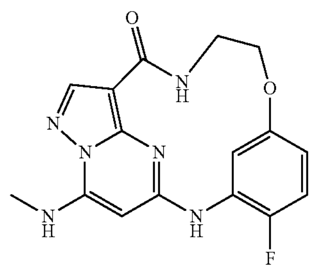 [SMILES: CNc1cc2nc3c(cnn13)C(=O)NCCOc1ccc(F)c(c1)N2] | (1³E,1⁴E)-3⁶-fluoro-1⁷-(methylamino)-4-oxa-2,7-diaza-1(5,3)-pyrazolo[1,5-a]pyrimidina-3(1,3)-benzenacyclooctaphan-8-one | 343.2 |
| 23 | 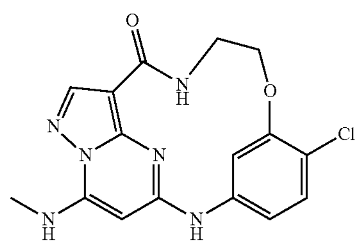 [SMILES: CNc1cc2nc3c(cnn13)C(=O)NCCOc1cc(ccc1Cl)N2] | (1³E,1⁴E)-3⁴-chloro-1⁷-(methylamino)-4-oxa-2,7-diaza-1(5,3)-pyrazolo[1,5-a]pyrimidina-3(1,3)-benzenacyclooctaphan-8-one | 359.3 |
| 24 | 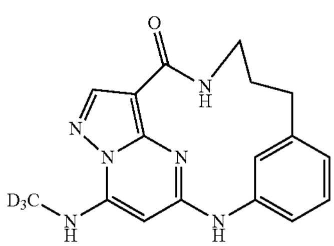 [SMILES: [2H]C([2H])([2H])Nc1cc2nc3c(cnn13)C(=O)NCCCc1cccc(c1)N2] | (1³E,1⁴E)-1⁷-((methyl-d3)amino)-2,7-diaza-1(5,3)-pyrazolo[1,5-a]pyrimidina-3(1,3)-benzenacyclooctaphan-8-one | 326.3 |
| 25 | 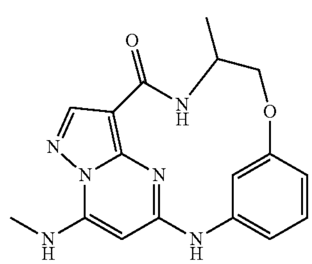 [SMILES: CNc1cc2nc3c(cnn13)C(=O)NC(C)COc1cccc(c1)N2] | (1³E,1⁴E)-6-methyl-1⁷-(methylamino)-4-oxa-2,7-diaza-1(5,3)-pyrazolo[1,5-a]pyrimidina-3(1,3)-benzenacyclooctaphan-8-one | 339.5 |
| 26 | 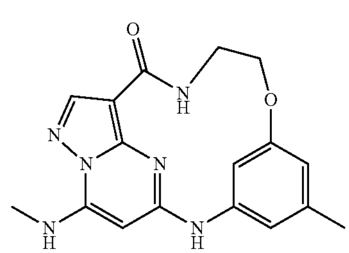 | (1³E,1⁴E)-3⁵-methyl-1⁷-(methylamino)-4-oxa-2,7-diaza-1(5,3)-pyrazolo[1,5-a]pyrimidina-3(1,3)-benzenacyclooctaphan-8-one | 339.3 |

-continued

| Compound | Structure | Name | MS [M + H]+ |
|---|---|---|---|
| 27 | 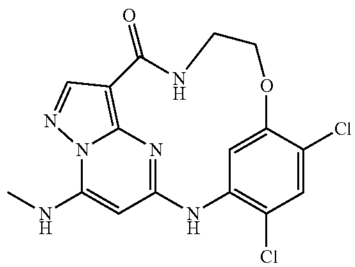 [SMILES: CNc1cc2nc3c(cnn13)C(=O)NCCOc1cc(c(Cl)cc1Cl)N2] | (1³E,1⁴E)-3⁴,3⁶-dichloro-1⁷-(methylamino)-4-oxa-2,7-diaza-1(5,3)-pyrazolo[1,5-a]pyrimidina-3(1,3)-benzenacyclooctaphan-8-one | 394.3 |
| 28 | 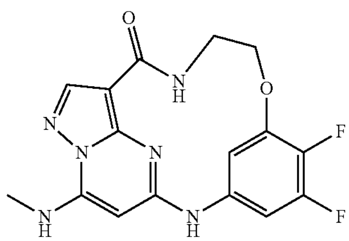 [SMILES: CNc1cc2nc3c(cnn13)C(=O)NCCOc1cc(cc(F)c1F)N2] | (1³E,1⁴E)-3⁴,3⁵-difluoro-1⁷-(methylamino)-4-oxa-2,7-diaza-1(5,3)-pyrazolo[1,5-a]pyrimidina-3(1,3)-benzenacyclooctaphan-8-one | 361.3 |
| 29 | 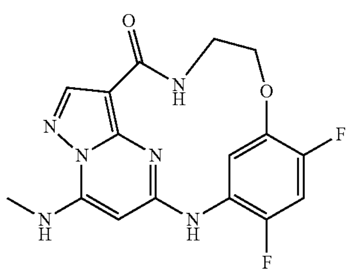 [SMILES: CNc1cc2nc3c(cnn13)C(=O)NCCOc1cc(c(F)cc1F)N2] | (1⁵E,1⁴E)-3⁴,3⁶-difluoro-1⁷-(methylamino)-4-oxa-2,7-diaza-1(5,3)-pyrazolo[1,5-a]pyrimidina-3(1,3)-benzenacyclooctaphan-8-one | 361.2 |
| 30 | 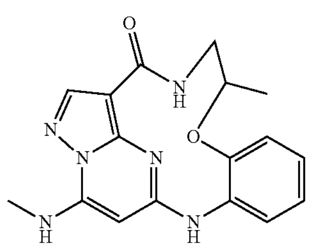 [SMILES: CNc1cc2nc3c(cnn13)C(=O)NCC(C)Oc1ccccc1N2] | (1³E,1⁴E)-5-methyl-1⁷-(methylamino)-4-oxa-2,7-diaza-1(5,3)-pyrazolo[1,5-a]pyrimidina-3(1,2)-benzenacyclooctaphan-8-one | 339.5 |
| 31 | 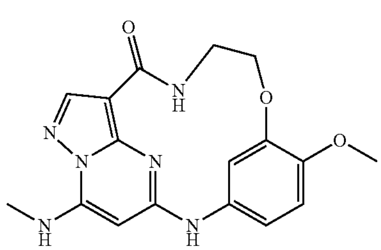 | (1³E,1⁴E)-3⁴-methoxy-1⁷-(methylamino)-4-oxa-2,7-diaza-1(5,3)-pyrazolo[1,5-a]pyrimidina-3(1,3)-benzenacyclooctaphan-8-one | 355.4 |
| 32 | 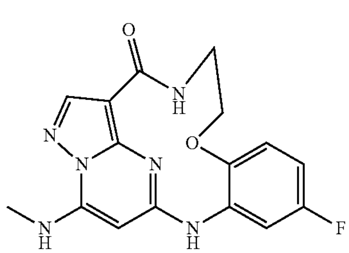 [SMILES: CNc1cc2nc3c(cnn13)C(=O)NCCOc1ccc(F)cc1N2] | (1³E,1⁴E)-3⁵-fluoro-1⁷-(methylamino)-4-oxa-2,7-diaza-1(5,3)-pyrazolo[1,5-a]pyrimidina-3(1,2)-benzenacyclooctaphan-8-one | 343.3 |

-continued

| Compound | Structure | Name | MS [M + H]+ |
|---|---|---|---|
| 33 | 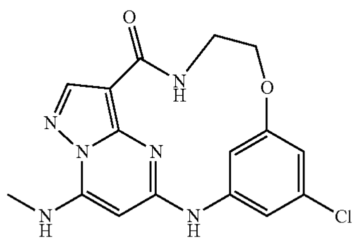 [SMILES: CNc1cc2nc3c(cnn13)C(=O)NCCOc1cc(Cl)cc(c1)N2] | (1³E,1⁴E)-3⁵-chloro-1⁷-(methylamino)-4-oxa-2,7-diaza-1(5,3)-pyrazolo[1,5-a]pyrimidina-3(1,3)-benzenacyclooctaphan-8-one | 359.8 |
| 34 | 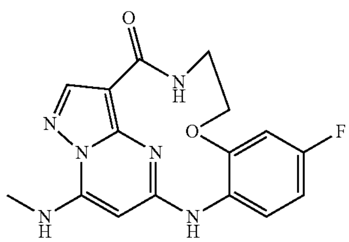 [SMILES: CNc1cc2nc3c(cnn13)C(=O)NCCOc1cc(F)ccc1N2] | (1³E,1⁴E)-3⁴-fluoro-1⁷-(methylamino)-4-oxa-2,7-diaza-1(5,3)-pyrazolo[1,5-a]pyrimidina-3(1,2)-benzenacyclooctaphan-8-one | 342.4 |
| 35 | 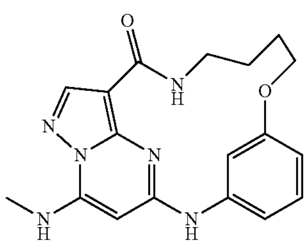 [SMILES: CNc1cc2nc3c(cnn13)C(=O)NCCCCOc1cccc(c1)N2] | (1³E,1⁴E)-1⁷-(methylamino)-4-oxa-2,9-diaza-1(5,3)-pyrazolo[1,5-a]pyrimidina-3(1,3)-benzenacyclodecaphan-10-one | 353.1 |
| 36 | 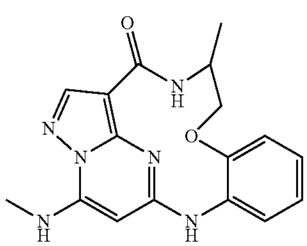 [SMILES: CNc1cc2nc3c(cnn13)C(=O)NC(C)COc1ccccc1N2] | (1³E,1⁴E)-6-methyl-1⁷-(methylamino)-4-oxa-2,7-diaza-1(5,3)-pyrazolo[1,5-a]pyrimidina-3(1,2)-benzenacyclooctaphan-8-one | 339.5 |
| 37 | 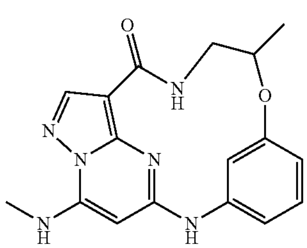 [SMILES: CNc1cc2nc3c(cnn13)C(=O)NCC(C)Oc1cccc(c1)N2] | (1³E,1⁴E)-5-methyl-1⁷-(methylamino)-4-oxa-2,7-diaza-1(5,3)-pyrazolo[1,5-a]pyrimidina-3(1,3)-benzenacyclooctaphan-8-one | 339.5 |
| 38 | 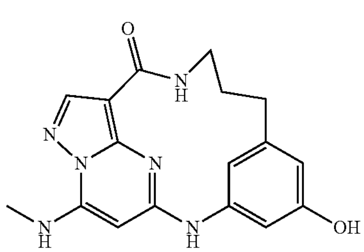 [SMILES: CNc1cc2nc3c(cnn13)C(=O)NCCCc1cc(O)cc(c1)N2] | (1³E,1⁴E)-3⁵-hydroxy-1⁷-(methylamino)-2,7-diaza-1(5,3)-pyrazolo[1,5-a]pyrimidina-3(1,3)-benzenacyclooctaphan-8-one | 339.3 |

-continued

| Compound | Structure | Name | MS [M + H]+ |
|---|---|---|---|
| 39 | 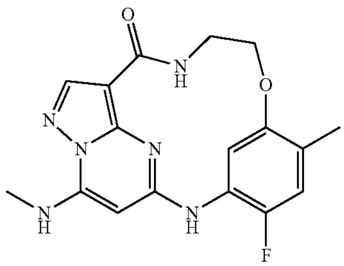 | ($1^3$E,$1^4$E)-$3^6$-fluoro-34-methyl-$1^7$-(methylamino)-4-oxa-2,7-diaza-1(5,3)-pyrazolo[1,5-a]pyrimidina-3(1,3)-benzenacyclooctaphan-8-one | 357.2 |
| 40 | 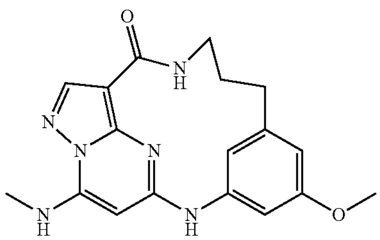 | ($1^3$E,$1^4$E)-$3^5$-methoxy-$1^7$-(methylamino)-2,7-diaza-1(5,3)-pyrazolo[1,5-a]pyrimidina-3(1,3)-benzenacyclooctaphan-8-one | 353.4 |
| 41 | 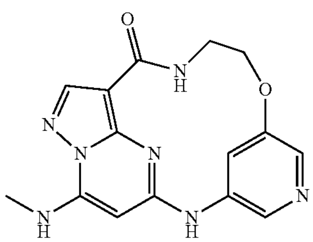 [SMILES: CNc1cc2nc3c(cnn13)C(=O)NCCOc1cncc(c1)N2] | ($1^3$E,$1^4$E)-$1^7$-(methylamino)-4-oxa-2,7-diaza-1(5,3)-pyrazolo[1,5-a]pyrimidina-3(3,5)-pyridinacyclooctaphan-8-one | 326.6 |
| 42 | 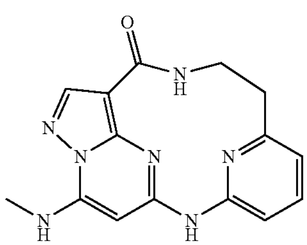 [SMILES: CNc1cc2nc3c(cnn13)C(=O)NCCc1cccc(n1)N2] | ($1^3$E,$1^4$E)-$1^7$-(methylamino)-2,6-diaza-1(5,3)-pyrazolo[1,5-a]pyrimidina-3(2,6)-pyridinacycloheptaphan-7-one | 310.2 |
| 43 | 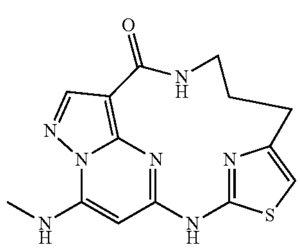 [SMILES: CNc1cc2nc3c(cnn13)C(=O)NCCCc1csc(n1)N2] | ($1^2$Z,$3^3$E,$3^4$E)-$3^7$-(methylamino)-2,5-diaza-1(2,4)-thiazola-3(5,3)-pyrazolo[1,5-a]pyrimidinacyclooctaphan-4-one | 330.2 |
| 44 | 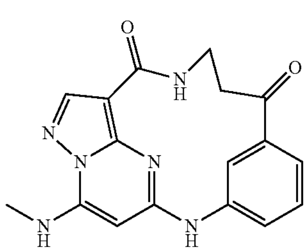 [SMILES: CNc1cc2nc3c(cnn13)C(=O)NCCC(=O)c1cccc(c1)N2] | ($1^3$E,$1^4$E)-$1^7$-(methylamino)-2,7-diaza-1(5,3)-pyrazolo[1,5-a]pyrimidina-3(1,3)-benzenacyclooctaphane-4,8-dione | 337.0 |

| Compound | Name | MS [M + H]+ |
|---|---|---|
| 45 | (1³E,1⁴E,3⁴E)-1⁷-(methylamino)-31H-2,7-diaza-1(5,3)-pyrazolo[1,5-a]pyrimidina-3(4,1)-pyrazolacyclooctaphan-8-one | 313.2 |
| 46 | (1³E,1⁴E)-3⁵-fluoro-1⁷-(methylamino)-4-oxa-2,8-diaza-1(5,3)-pyrazolo[1,5-a]pyrimidina-3(1,2)-benzenacyclononaphan-9-one | 357.4 |
| 47 | (1³E,1⁴E,3⁴E)-1⁷-(methylamino)-31H-2,6-diaza-1(5,3)-pyrazolo[1,5-a]pyrimidina-3(4,1)-pyrazolacycloheptaphan-7-one | 299.2 |

Example 3: JAK/TYK2 Assay 10 mM test compound stock or 1 mM control compound stock (tofocitinib, ruxolitinib or staurosporine) in DMSO was diluted to 0.4 mM in DMSO. A 3-fold series dilution was then performed in DMSO to generate 10 different compound concentrations. The assay was carried out in 384-well white plate. 0.5 uL of 40× compound DMSO solution at different concentrations was mixed with 10 uL 2× enzyme prepared in reaction buffer (20 mM HEPES, 10 mM $MgCl_2$, 0.01% Tween, 1 mM DTT, pH 7.5). 10 uL 2× substrate mixture prepared in reaction buffer was then added to start the reaction. A short spin was done to settle down all solutions to the bottom of the plate. Final concentrations of test compound in the reaction mixture were 10000, 3333, 1111, 370, 123, 41.2, 13.7, 4.57, 1.52 and 0.51 nM. Concentrations of control compound were ten times less. Enzymatic reaction was conducted at 25° C. for 1-2 hours. 10 uL of Kinase Glo Reagents was added to stop the reaction and generate the luminescent signal which was measured using Envision. Luminescence signal was inversely related to kinase activity. Reaction mixture which doesn't contain enzyme served as negative control. The mixture without any compound was the positive control. Final concentration of enzymes and substrates and incubation time are summarized in the table below.

| | [enz] | [ATP] | [sub] | time |
|---|---|---|---|---|
| JAK1 | 7.5 nM | 2 uM | 30 uM (IRS-1) | 1 hr |
| JAK2 | 0.8 nM | 2 uM | 4 uM (pEY) | 1 hr |
| JAK3 | 1.5 nM | 2 uM | 4 uM (pEY) | 1 hr |
| TYK2 | 9 nM | 2 uM | 30 uM (IRS-1) | 1 hr |

Example 4: Co-Stimulation Assay in Lysed Whole Blood; JAK2: GM-CSF Stimulated STAT5 Phosphorylation and JAK1/TYK2 Stimulated STAT1 Phosphorylation Assay Human Blood Lysis Using Abcam's RBC Lysis Buffer Dilute RBC lysis buffer to 1× in distilled water. Add 2 mL blood to 38 mL of 1×RBC-lysis buffer. Incubate for 15 mins at RT, in dark. Spin at 300 g, 5 mins, to collect the pellet. Re-lyse if necessary. Re-suspend pellet in 5 mL of cRPMI.

Compound and Cytokine Treatment

Aliquot 80 μL of lysed human blood in to wells of 96 deep-well plate. Add 10 μl of (10× conc.) of different concentrations of compounds to all wells except controls (unstained and unstimulated) and mix it with the help of 100 uL multichannel. Add 10 uL of RPMI media in controls. For dilution of compounds and dilution range please refer Appendix. Incubate on water bath or $CO_2$ incubator for 1 hour at 37° C. Add 10 μL of (10× conc.) of cytokine mix (GM-CSF and IFNa) (final conc. 10 ng/mL of GM-CSF and 100 ng/mL of IFNa) to each well except unstimulated and unstained controls and incubate further for 20 minutes on water bath at 37° C.

RBC Lysis and Fixation

Add 900 µL of prewarmed 1× Fix/Lyse solution (Appendix) and mix it properly using 1000 µl multichannel, incubate further on water bath at 37° C. for 10 minutes (which includes time of addition). Centrifuge at 800× g for 5 minutes at 40° C.; remove 900 uL of supernatant and add 900 µL of 1×PBS. Centrifuge at 800× g for 5 minutes at 40° C., remove 900 µL of supernatant. Wash one more time with 900 µL of PBS (optional) and resuspend pellets in 100 uL of PBS.

Permeabilization

Disrupt the pellet by gentle tapping and resuspend in 1000 µL of BD Phosflow Perm Buffer III and incubate plate on ice for 30 minutes. Centrifuge plate at 800× g for 5 minutes at 40° C. Wash two more times with 1000 µL of BD Pharmingen Stain Buffer.

Antibody Treatment

Disrupt the pellet by gentle tapping. Resuspend pellets in 100 uL of Stain Buffer and add 5 µL of pSTAT5_AF488 Ab and 5 uL of pSTAT1_PE in all wells except unstained control and mix properly using 200 µl multichannel, incubate overnight at 40° C. Add 900 µL of wash buffer and centrifuge at 1800 rpm for 3 minutes at 40° C. Wash one more time with 1000 µL of BD Pharmingen Stain Buffer. Finally resuspend the pellet in 300 uL of BD Pharmingen Stain Buffer. Transfer the cells to 96-well v-bottom plate and acquire the cells in Beckman Coulter CytExpert. Acquiring cells in Flow Cytometer: Keep the threshold value to 250 and cell concentration should not exceed 100-500 cells/µL. Acquire at least 5,000-10,000 cells.

APPENDIX

Preparation of Reagents

RPMI 1640 Complete Medium: RPMI 1640 media+10% FBS.

Cytokine dilution: 1) GM-CSF Stock at 100 ug/mL. Prepare an intermediate dilution of 1 ug/mL by adding 2 uL of stock into 198 uL of cRPMI. Further dilute to 100 ng/mL by adding 100 uL of the intermediate stock to 900 uL of cRPMI. 2) IFNa Stock at 200 ug/mL. Dilute IFNa stock 1:200 by adding 5 uL of stock into the 1000 uL of 100 ng/mL GM-CSF working stock as above to give a combined working stock of 1000 ng/mL of IFNa and 100 ng/mL GM-CSF (lox). Keep it on ice until used.

Lyse/Fix buffer preparation: Dilute 5× Lyse/Fix buffer to 1× using MQ water and keep at 37° C. until used.

BD Phosflow perm buffer III: Keep on ice/fridge.

Compound Dilution

| Sample | Final concentration, nM | 10× concentration, nM | Dilution |
|---|---|---|---|
| 1 | 10,000 | 100,000 | 2 µL of 10 mM compound + 198 µL of cRPMI media |
| 2 | 3333.3 | 33,333 | 60 µL of A + 120 µL of cRPMI media |
| 3 | 1111.1 | 11,111 | 60 uL of B + 120 µL of cRPMI media |
| 4 | 370.4 | 3,704 | 60 µL of C + 120 µL of cRPMI media |
| 5 | 123.5 | 1,235 | 60 µL of D + 120 µL of cRPMI media |
| 6 | 41.2 | 412 | 60 µL of E + 120 µL of cRPMI media |
| 7 | 13.7 | 137 | 60 µL of F + 120 µL of cRPMI media |
| 8 | 4.6 | 46 | 60 µL of G + 120 µL of cRPMI media |
| 9 | 0 | 0 | 2 µL of DMSO + 198 µL of cRPMI media |

IC50 values are shown in the table below.

| Compound | IFN-a/Jak1Tyk2 IC50 |
|---|---|
| 7 | A |
| 12 | B |
| 13 | A |
| 14 | A |
| 15 | A |
| 16 | A |
| 17 | A |
| 18 | B |
| 19 | B |
| 20 | B |
| 21 | B |
| 22 | B |
| 23 | B |
| 24 | B |
| 25 | B |
| 26 | B |
| 27 | B |
| 28 | B |
| 29 | B |
| 30 | B |
| 31 | B |
| 32 | B |
| 33 | B |
| 34 | B |
| 35 | B |
| 36 | B |
| 37 | C |
| 38 | C |
| 39 | C |
| 40 | C |
| 41 | C |
| 42 | C |
| 43 | C |
| 44 | C |
| 45 | C |
| 46 | C |
| 47 | C |

A: $IC_{50} \leq 500$ nM; B: $IC_{50} \geq 100$ nM and $<1$ uM; C: $IC_{50} \geq 1$ uM and $\leq 10$ uM The examples and embodiments described herein are for illustrative purposes only and in some embodiments, various modifications or changes are to be included within the purview of disclosure and scope of the appended claims.

What is claimed is:

1. A compound having the structure of Formula (III):

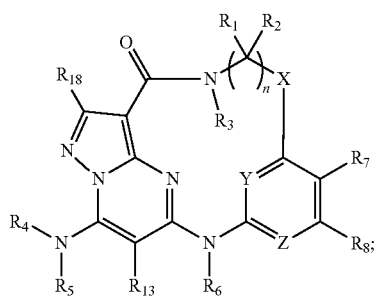

Formula (III)

wherein:
X is —O— or —C(R$_9$)(R$_{10}$)—;
Y is =N— or =C(R$_{15}$)—;
Z is =N— or =C(R$_{16}$)—;
each R$_1$ is independently selected from hydrogen, deuterium, C$_1$-C$_6$alkyl, and C$_1$-C$_6$deuteroalkyl;
each R$_2$ is independently selected from hydrogen, deuterium, C$_1$-C$_6$alkyl, and C$_1$-C$_6$deuteroalkyl;
R$_3$ is hydrogen or C$_1$-C$_6$alkyl;
R$_4$ is selected from hydrogen, deuterium, C$_1$-C$_6$alkyl, C$_1$-C$_6$deuteroalkyl, C$_1$-C$_6$heteroalkyl, C$_3$-C$_6$cycloalkyl, and C$_2$-C$_9$heterocycloalkyl;
R$_5$ is selected from hydrogen, deuterium, C$_1$-C$_6$alkyl, C$_1$-C$_6$deuteroalkyl, C$_1$-C$_6$heteroalkyl, C$_3$-C$_6$cycloalkyl, and C$_2$-C$_9$heterocycloalkyl;
R$_{13}$ is hydrogen, deuterium, C$_1$-C$_6$alkyl, or C$_1$-C$_6$deuteroalkyl; or R$_5$ and R$_{13}$ together with the atoms to which they are attached are combined to form a 5- or 6-membered heterocycloalkyl ring or a 5- or 6-membered heteroaryl ring, wherein the 5- or 6-membered heterocycloalkyl ring or 5- or 6-membered heteroaryl ring is optionally substituted with 1, 2, or 3 groups selected from halogen, C$_1$-C$_6$alkyl, C$_1$-C$_6$haloalkyl, C$_1$-C$_6$alkoxy, and C$_1$-C$_6$haloalkoxy;
R$_6$ is hydrogen or C$_1$-C$_6$alkyl;
R$_7$ and R$_8$ are independently selected from hydrogen, deuterium, halogen, C$_1$-C$_6$alkyl, C$_2$-C$_6$deuteroalkyl, —C$_1$-C$_6$alkyl-OH, C$_1$-C$_6$haloalkyl, C$_1$-C$_6$alkoxy, C$_3$-C$_6$cycloalkyl, C$_2$-C$_9$heterocycloalkyl, C$_2$-C$_9$heteroaryl, C$_6$-C$_{10}$aryl, —OR$_{11}$, —N(R$_{11}$)$_2$, —CN, —C(=O)R$_{12}$, —C(=O)OR$_{11}$, —C(=O)N(R$_{11}$)$_2$, —NR$_{11}$C(=O)R$_{12}$, —NR$_{11}$S(=O)$_2$R$_{12}$, —S(=O)$_2$R$_{12}$, and —S(=O)$_2$N(R$_{11}$)$_2$, wherein C$_3$-C$_6$cycloalkyl, C$_2$-C$_9$heterocycloalkyl, C$_2$-C$_9$heteroaryl, or C$_6$-C$_{10}$aryl are optionally substituted with 1, 2, or 3 groups selected from halogen, C$_1$-C$_6$alkyl, C$_1$-C$_6$haloalkyl, C$_1$-C$_6$alkoxy, and C$_1$-C$_6$haloalkoxy;
R$_9$ and R$_{10}$ are independently selected from hydrogen, deuterium, C$_1$-C$_6$alkyl, and C$_1$-C$_6$deuteroalkyl;
each R$_{11}$ is independently selected from hydrogen, C$_1$-C$_6$alkyl, C$_1$-C$_6$haloalkyl, C$_1$-C$_6$heteroalkyl, and phenyl, wherein phenyl is optionally substituted with 1, 2, or 3 groups selected from halogen, C$_1$-C$_6$alkyl, C$_1$-C$_6$haloalkyl, C$_1$-C$_6$alkoxy, C$_1$-C$_6$haloalkoxy, C$_2$-C$_9$heterocycloalkyl, C$_2$-C$_9$heteroaryl, —OR$_{14}$, —N(R$_{14}$)$_2$, —C(=O)OR$_{14}$, and —C(=O)N(R$_{14}$)$_2$;
each R$_{12}$ is independently selected from C$_1$-C$_6$alkyl and C$_1$-C$_6$heteroalkyl;
each R$_{14}$ is independently selected from hydrogen, C$_1$-C$_6$alkyl, and C$_1$-C$_6$haloalkyl;
R$_{15}$ and R$_{16}$ are independently selected from hydrogen, deuterium, halogen, C$_1$-C$_6$alkyl, C$_1$-C$_6$deuteroalkyl, C$_1$-C$_6$haloalkyl, C$_1$-C$_6$alkoxy, C$_1$-C$_6$heteroalkyl, —OR$_{11}$, —N(R$_{11}$)$_2$, —CN, —C(=O)R$_{12}$, —C(=O)OR$_{11}$, —C(=O)N(R$_{11}$)$_2$, —NR$_{11}$C(=O)R$_{12}$, —NR$_{11}$S(=O)$_2$R$_{12}$, —S(=O)$_2$R$_{12}$, and —S(=O)$_2$N(R$_{11}$)$_2$;
R$_{18}$ is hydrogen, deuterium, halogen, C$_1$-C$_6$alkyl, or C$_1$-C$_6$deuteroalkyl; and
n is 1, 2, 3, or 4;
or a pharmaceutically acceptable salt or solvate thereof.

2. The compound of claim 1, or a pharmaceutically acceptable salt or solvate thereof, wherein Y is =C(R$_{15}$)— and Z is =C(R$_{16}$)—.

3. The compound of claim 2, or a pharmaceutically acceptable salt or solvate thereof, wherein R$_{16}$ is selected from hydrogen, halogen, and C$_1$-C$_6$alkyl.

4. The compound of claim 3, or a pharmaceutically acceptable salt or solvate thereof, wherein R$_{15}$ is selected from hydrogen, halogen, and C$_1$-C$_6$alkyl.

5. The compound of claim 4, or a pharmaceutically acceptable salt or solvate thereof, wherein R$_7$ and R$_8$ are independently selected from hydrogen, halogen, and C$_1$-C$_6$alkyl.

6. The compound of claim 5, or a pharmaceutically acceptable salt or solvate thereof, wherein X is —O—.

7. The compound of claim 5, or a pharmaceutically acceptable salt or solvate thereof, wherein X is —C(R$_9$)(R$_{10}$)—.

8. The compound of claim 7, or a pharmaceutically acceptable salt or solvate thereof, wherein R$_9$ and R$_{10}$ are hydrogen.

9. The compound of claim 5, or a pharmaceutically acceptable salt or solvate thereof, wherein R$_4$ is hydrogen and R$_5$ is C$_1$-C$_6$alkyl.

10. The compound of claim 9, or a pharmaceutically acceptable salt or solvate thereof, wherein R$_3$ is hydrogen.

11. The compound of claim 10, or a pharmaceutically acceptable salt or solvate thereof, wherein n is 1.

12. The compound of claim 10, or a pharmaceutically acceptable salt or solvate thereof, wherein n is 2.

13. The compound of claim 10, or a pharmaceutically acceptable salt or solvate thereof, wherein n is 3.

14. The compound of claim 10, or a pharmaceutically acceptable salt or solvate thereof, wherein each R$_1$ is hydrogen.

15. The compound of claim 14, or a pharmaceutically acceptable salt or solvate thereof, wherein each R$_2$ is hydrogen.

16. The compound of claim 10, or a pharmaceutically acceptable salt or solvate thereof, wherein R$_{18}$ is hydrogen.

17. A compound selected from:

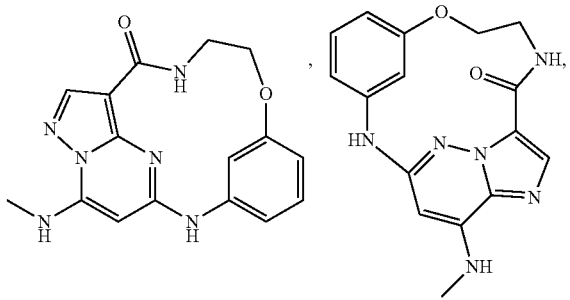

-continued
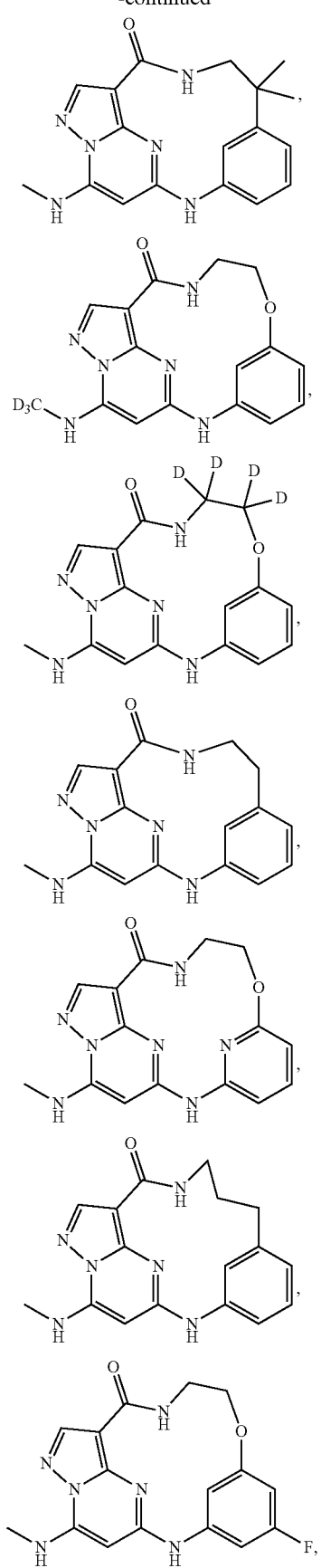
-continued
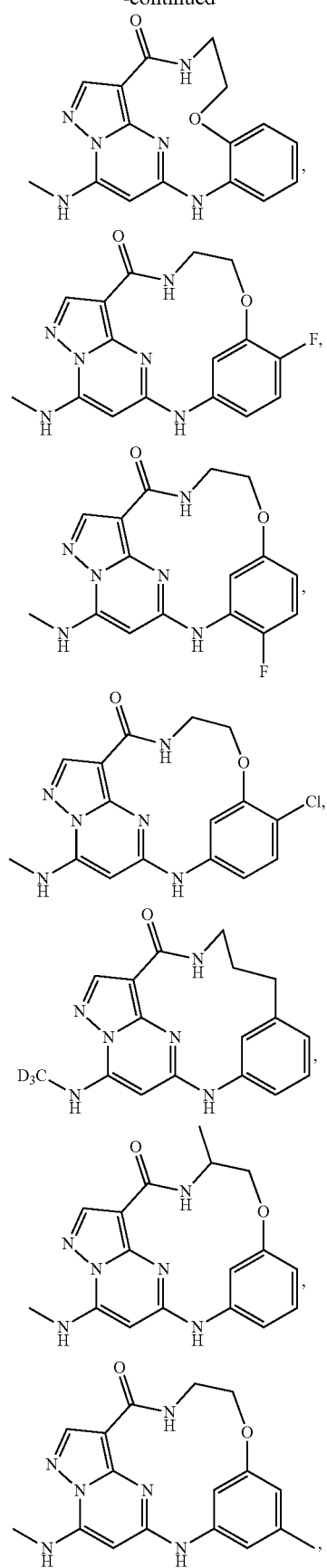

127
-continued
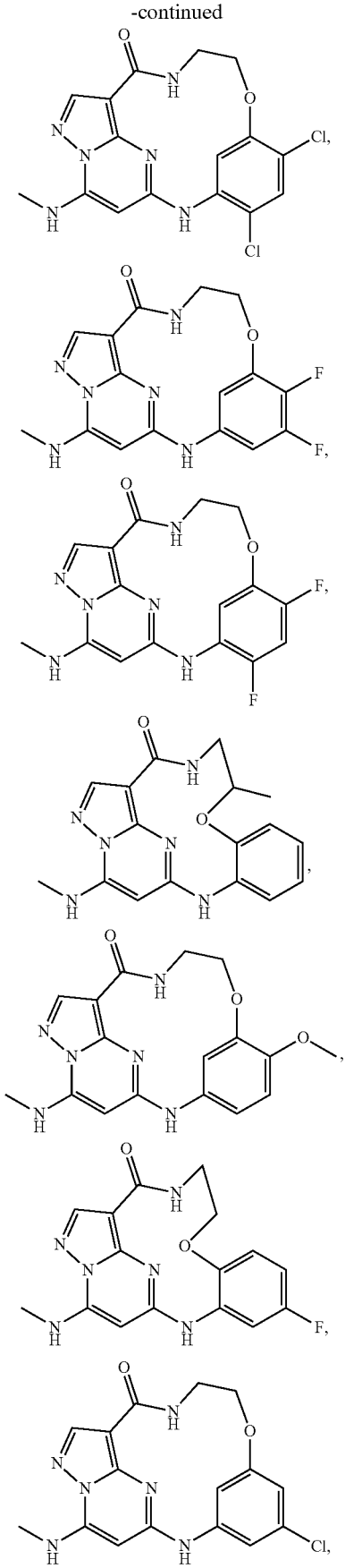
128
-continued
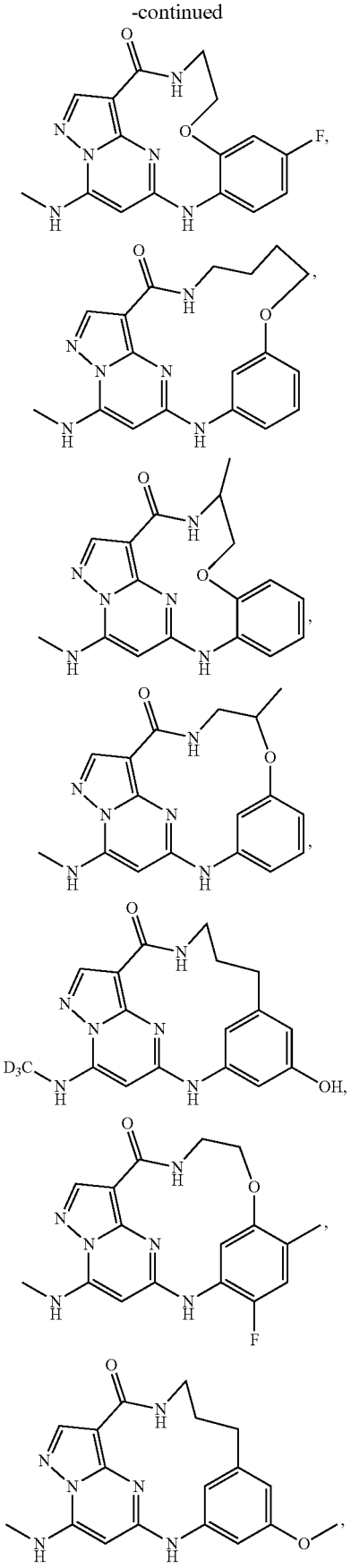

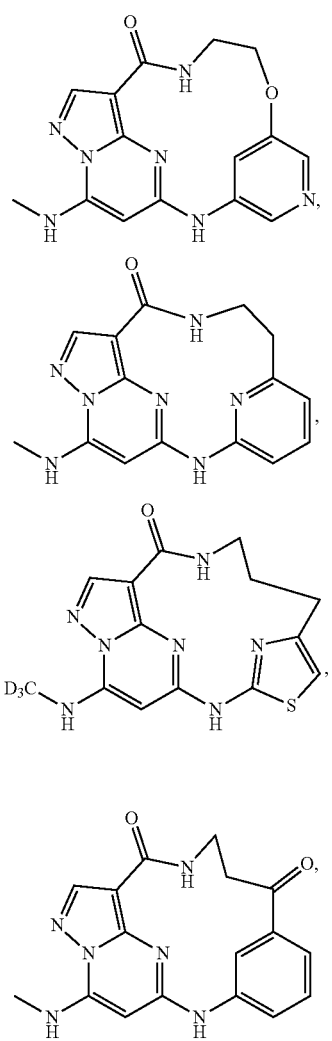

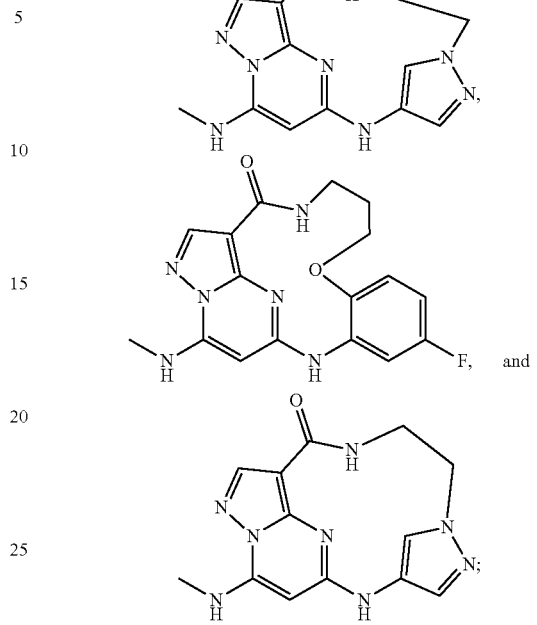

or a pharmaceutically acceptable salt or solvate thereof.

18. A pharmaceutical composition comprising a compound of claim 1, or a pharmaceutically acceptable salt or solvate thereof, and a pharmaceutically acceptable excipient.

19. A method of treating rheumatoid arthritis, multiple sclerosis, psoriasis, lupus, intestinal bowel disease, Crohn's disease, ulcerative colitis, ankylosing spondylitis, vitiligo, and atopic dermatitis in a patient in need thereof, comprising administering to the patient a therapeutically effective amount of a compound of claim 1, or a pharmaceutically acceptable salt or solvate thereof, wherein said treating is for therapeutic benefit.

* * * * *